United States Patent
Soares da Silva

(10) Patent No.: US 10,590,422 B2
(45) Date of Patent: Mar. 17, 2020

(54) ANTICANCER THERAPEUTIC INTERVENTION

(71) Applicant: PHYZAT BIOPHARMACEUTICALS, LDA., Oporto (PT)

(72) Inventor: Patricio Soares da Silva, Oporto (PT)

(73) Assignee: PHYZAT BIOPHARMACEUTICALS, LDA., Oporto (PT)

( * ) Notice: Subject to any disclaimer, the term of this patent is extended or adjusted under 35 U.S.C. 154(b) by 0 days.

(21) Appl. No.: 15/622,859

(22) Filed: Jun. 14, 2017

(65) Prior Publication Data

US 2017/0362598 A1 Dec. 21, 2017

(51) Int. Cl.
*C12N 15/113* (2010.01)

(52) U.S. Cl.
CPC ...... *C12N 15/1138* (2013.01); *C12N 2310/14* (2013.01); *C12N 2310/50* (2013.01); *C12N 2320/31* (2013.01)

(58) Field of Classification Search
None
See application file for complete search history.

(56) References Cited

U.S. PATENT DOCUMENTS

| | | | | |
|---|---|---|---|---|
| 2004/0265230 A1* | 12/2004 | Martinez | .......... | G01N 33/57419 424/1.49 |
| 2005/0255487 A1* | 11/2005 | Khvorova | ............ | A61K 31/713 435/6.11 |
| 2016/0161494 A1 | 6/2016 | Ruben et al. | | |

FOREIGN PATENT DOCUMENTS

WO 2008026946 A2 3/2008

OTHER PUBLICATIONS

International Search Report and Written Opinion dated Dec. 8, 2017 for corresponding International Application No. PCT/EP2017/064649.
Chang-Hyun Kim et al: "The RNA Interference of Amino Acid Transporter LAT1 Inhibits the Growth of KB Human Oral Cancer Cells", Anticancer Research, Jul. 1, 2016, vol. 26, p. 2943-2948.
Minhui Xu et al: "Up-Regulation of LAT1 During Antiandrogen Therapy Contributes to Progression in Prostate Cancer Cells", Journal of Urology, May 2016, vol. 195, No. 5, pp. 1588-1597.
Mayumi Ohkawa et al: "Oncogenicity of L-Type Amino-Acid Transporter 1 (LAT1) revealed by Targeted Gene Disruption in Chicken DT40 Cells: LAT1 is a Promising Molecular Target for Human Cancer Therapy", Biochemical and Biophysical Research Communications, Mar. 2011, vol. 406, No. 4, pp. 649-655.
Justin K Tomblin et al: "Aryl Hydrocarbon Receptor (AHR) Regulation of L-Type Amino Acid Transporter 1 (LAT-1) Expression in MCF-7 and MDA-MB-231 Breast Cancer Cells", Biochemical Pharmacology, Mar. 2, 2016, vol. 106, pp. 94-103.
Ryan S. Youland et al: "The Role of LAT1 in F-DOPA Uptake in Malignant Gliomas", Journal of Neuro-Oncology, Oct. 20, 2012, vol. 111, No. 1, pp. 11-18.
Zhongxing Liang et al: "Potential Biomarker of L-Type Amino Acid Transporter 1 in Breast Cancer Progression", Journal of Nuclear Medicine and Molecular Imaging, Nov. 24, 2010, vol. 45, No. 2, pp. 93-102.
Barel M, Meibom K, Dubail I, Botella J, Charbit A (2012). Francisella tularensis regulates the expression of the amino acid transporter SLC1A5 in infected THP-1 human monocytes. Cell Microbiol 14: 1769-1783.
Betsunoh H, Fukuda T, Anzai N, Nishihara D, Mizuno T, Yuki H, et al. (2013). Increased expression of system large amino acid transporter (LAT)-1 mRNA is associated with invasive potential and unfavorable prognosis of human clear cell renal cell carcinoma. BMC Cancer 13: 509-519.
Biology EoNC (2003). Whither RNAi ? Nature Cell Biology 5: 489-490.
Broer S, Broer A, Hamprecht B (1997). Expression of the surface antigen 4F2hc affects system-L-like neutral-amino-acid-transport activity in mammalian cells. Biochem J 324 535-541.
Brummelkamp TR, Bernards R, Agami R (2002). A system for stable expression of short interfering RNAs in mammalian cells. Science 296: 550-553.
Bryan CF, Perez JC, Julie ES, Sofia BC, Barrie PB (2004). Inducible antisense RNA targeting amino acid transporter ATB0/ASCT2 elicits apoptosis in human hepatoma cells. American Journal of Physiology—Gastrointestinal and Liver Physiology.
Chuntao T, Shixin L, Qingxia F, Weijie Z, Shunchang J, Xiao Z, et al. (2015). Prognostic Significance of Tumor-infiltrating CD8 + or CD3 + T Lymphocytes and Interleukin-2 Expression in Radically Resected Non-small Cell Lung Cancer. Chinese Medical Journal 128: 105-110.
Davis ME (2009). The first targeted delivery of siRNA in humans via a self-assembling, cyclodextrin polymer-based nanoparticle: from concept to clinic. Mol Pharm 6: 659-668.
Denoyer D, Kirby L, Waldeck K, Roselt P, Neels OC, Bourdier T, et al. (2012). Preclinical characterization of 18F-D-FPHCys, a new amino acid-based PET tracer. Eur J Nucl Med Mol Imaging 39: 703-712.
Dickens D, Webb SD, Antonyuk S, Giannoudis A, Owen A, Radisch S, et al. (2013). Transport of gabapentin by LAT1 (SLC7A5). Biochem Pharmacol 85: 1672-1683.

(Continued)

Primary Examiner — Richard A Schnizer
(74) *Attorney, Agent, or Firm* — Tarolli, Sundheim, Covell & Tummino LLP

(57) ABSTRACT

The present invention is directed to a method of treating cancer using interfering RNA duplexes to mediate gene silencing. The present invention is also directed to interfering RNA duplexes and vectors encoding such interfering RNA duplexes.

9 Claims, 32 Drawing Sheets

Specification includes a Sequence Listing.

(56) References Cited

OTHER PUBLICATIONS

Ebara T, Kaira K, Saito J, Shioya M, Asao T, Takahashi T, et al. (2010). L-type amino-acid transporter 1 expression predicts the response to preoperative hyperthermo-chemoradiotherapy for advanced rectal cancer. Anticancer Res 30: 4223-4227.

Elbashir SM, Harborth J, Lendeckel W, Yalcin A, Weber K, Tuschl T (2001). Duplexes of 21-nucleotide RNAs mediate RNA interference in cultured mammalian cells. Nature 411: 494-498.

Eltz S, Comperat E, Cussenot O, Roupret M (2008). Molecular and histological markers in urothelial carcinomas of the upper urinary tract. BJU Int 102: 532-535.

Emer C, Helen I, Deirdre W, Mark W, Kate D, Laura SM, et al. (2013). Prognostic Significance of Deregulated Dicer Expression in Breast Cancer. PLoS One 8: e83724.

Feral CC, Nishiya N, Fenczik CA, Stuhlmann H, Slepak M, Ginsberg MH (2005). CD98hc (SLC3A2) mediates integrin signalling. Proc Natl Acad Sci USA 102: 355-360.

Fire A, Xu S, Montgomery MK, Kostas SA, Driver SE, Mello CC (1998). Potent and specific genetic interference by double-stranded RNA in Caenorhabditis elegans. Nature 391: 806-811.

Fuchs BC, Bode BP (2005). Amino acid transporters ASCT2 and LAT1 in cancer: partners in crime? Semin Cancer Biol 15: 254-266.

Fuchs BC, Perez JC, Suetterlin JE, Chaudhry SB, Bode BP (2004). Inducible antisense RNA targeting amino acid transporter ATB0/ASCT2 elicits apoptosis in human hepatoma cells. Am J Physiol Gastrointest Liver Physiol 286: G467-478.

Fukumoto S, Hanazono K, Komatsu T, Iwano H, Kadosawa T, Uchide T (2013). L-type amino acid transporter 1 (LAT1) expression in canine mammary gland tumors. J Vet Med Sci 75: 431-437.

Furuya M, Horiguchi J, Nakajima H, Kanai Y, Oyama T (2012). Correlation of L-type amino acid transporter 1 and CD98 expression with triple negative breast cancer prognosis. Cancer Sci 103: 382-389.

Gaccioli F, Aye IL, Roos S, Lager S, Ramirez VI, Kanai Y, et al. (2015). Expression and functional characterisation of System L amino acid transporters in the human term placenta. Reprod Biol Endocrinol 13: 57.

Ge NJ, Shi ZY, Yu XH, Huang XJ, Wu YS, Chen YY, et al. (2015). Genetic Variants in ASCT2 Gene are Associated with the Prognosis of Transarterial Chemoembolisation-Treated Early-Stage Hepatocelluar Carcinoma. Asian Pac J Cancer Prev 16: 4103-4107.

Habermeier A, Graf J, Sandhofer BF, Boissel JP, Roesch F, Closs EI (2015). System L amino acid transporter LAT1 accumulates O-(2-fluoroethyl)-L-tyrosine (FET). Amino Acids 47: 335-344.

Hannon GJ (2002). RNA interference. Nature 418: 244-251.

Harborth J, Elbashir SM, Bechert K, Tuschl T, Weber K (2001). Identification of essential genes in cultured mammalian cells using small interfering RNAs. J Cell Sci 114: 4557-4565.

Hassanein M, Hoeksema MD, Shiota M, Qian J, Harris BK, Chen H, et al. (2013). SLC1A5 mediates glutamine transport required for lung cancer cell growth and survival. Clin Cancer Res 19: 560-570.

Hassanein M, Qian J, Hoeksema MD, Wang J, Jacobovitz M, Ji X, et al. (2015). Targeting SLC1a5-mediated glutamine dependence in non-small cell lung cancer. Int J Cancer 137: 1587-1597.

Hayashi K, Jutabha P, Endou H, Anzai N (2012). c-Myc is crucial for the expression of LAT1 in MIA Paca-2 human pancreatic cancer cells. Oncology reports 28: 862-866.

Hayashi K, Jutabha P, Endou H, Sagara H, Anzai N (2013). LAT1 is a critical transporter of essential amino acids for immune reactions in activated human T cells. J Immunol 191: 4080-4085.

Honjo H, Kaira K, Miyazaki T, Yokobori T, Kanai Y, Nagamori S, et al. (2016). Clinicopathological significance of LAT1 and ASCT2 in patients with surgically resected esophageal squamous cell carcinoma. J Surg Oncol 113: 381-389.

Isoda A, Kaira K, Iwashina M, Oriuchi N, Tominaga H, Nagamori S, et al. (2014). Expression of L-type amino acid transporter 1 (LAT1) as a prognostic and therapeutic indicator in multiple myeloma. Cancer Sci 105: 1496-1502.

Jacque J-M, Triques K, Stevenson M (2002). Modulation of HIV-1 replication by RNA interference. Nature 418: 435-438.

Kaira K, Arakawa K, Shimizu K, Oriuchi N, Nagamori S, Kanai Y, et al. (2015a). Relationship between CD147 and expression of amino acid transporters (LAT1 and ASCT2) in patients with pancreatic cancer Am J Transl Res 7: 356-363.

Kaira K, Nakagawa K, Ohde Y, Okumura T, Takahashi T, Murakami H, et al. (2012a). Depolarized MUC1 expression is closely associated with hypoxic markers and poor outcome in resected non-small cell lung cancer. Int J Surg Pathol 20: 223-232.

Kaira K, Toyoda M, Shino M, Sakakura K, Takahashi K, Tominaga H, et al. (2013). Clinicopathological significance of L-type amino acid transporter 1 (LAT1) expression in patients with adenoid cystic carcinoma. Pathol Oncol Res 19: 649-656.

Kaira K, Oriuchi N, Imai H, Shimizu K, Yanagitani N, Sunaga N, et al. (2009b). Prognostic significance of L-type amino acid transporter 1 (LAT1) and 4F2 heavy chain (CD98) expression in early stage squamous cell carcinoma of the lung. Cancer Sci 100: 248-254.

Kaira K, Takahashi T, Murakami H, Shukuya T, Kenmotsu H, Naito T, et al. (2011a). Relationship between LAT1 expression and response to platinum-based chemotherapy in non-small cell lung cancer patients with postoperative recurrence. Anticancer Res 31: 3775-3782.

Kaira K, Oriuchi N, Imai H, Shimizu K, Yanagitani N, Sunaga N, et al. (2008a). l-type amino acid transporter 1 and CD98 expression in primary and metastatic sites of human neoplasms. Cancer Sci 99: 2380-2386.

Kaira K, Oriuchi N, Imai H, Shimizu K, Yanagitani N, Sunaga N, et al. (2010b). Prognostic significance of L-type amino acid transporter 1 (LAT1) and 4F2 heavy chain (CD98) expression in surgically resectable stage III non-small cell lung cancer Exp Ther Med 1: 799-808.

Kaira K, Oriuchi N, Shimizu K, Ishikita T, Higuchi T, Imai H, et al. (2009d). Correlation of angiogenesis with 18F-FMT and 18F-FDG uptake in non-small cell lung cancer. Cancer Sci 100: 753-758.

Kaira K, Oriuchi N, Takahashi T, Nakagawa K, Ohde Y, Okumura T, et al. (2011b). LAT1 expression is closely associated with hypoxic markers and mTOR in resected non-small cell lung cancer. Am J Transl Res 3: 468-478.

Kaira K, Oriuchi N, Takahashi T, Nakagawa K, Ohde Y, Okumura T, et al. (2011c). L-type amino acid transporter 1 (LAT1) expression in malignant pleural mesothelioma. Anticancer Res 31: 4075-4082.

Kaira K, Oriuchi N, Otani Y, Shimizu K, Tanaka S, Imai H, et al. (2007). Fluorine-18-alpha-methyltyrosine positron emission tomography for diagnosis and staging of lung cancer: a clinicopathologic study. Clin Cancer Res 13: 6369-6378.

Kaira K, Sunose Y, Arakawa K, Ogawa T, Sunaga N, Shimizu K, et al. (2012b). Prognostic significance of L-type amino-acid transporter 1 expression in surgically resected pancreatic cancer. Br J Cancer 107: 632-638.

Kanai Y, Endou H (2001). Heterodimeric amino acid transporters: molecular biology and pathological and pharmacological relevance. Curr Drug Metab 2: 339-354.

Kanai Y, Segawa H, Miyamoto K, Uchino H, Takeda E, Endou H (1998). Expression cloning and characterization of a transporter for large neutral amino acids activated by the heavy chain of 4F2 antigen (CD98). J Biol Chem 273: 23629-23632.

Kaneko S, Ando A, Okuda-Ashitaka E, Maeda M, Furuta K, Suzuki M, et al. (2007). Ornithine transport via cationic amino acid transporter-1 is involved in ornithine cytotoxicity in retinal pigment epithelial cells. Invest Ophthalmol Vis Sci 48: 464-471.

Kaoru K, Toshiaki K, Tomohiko Y, Yuichi T, Takahiro H, Koji N, et al. (2011). Positive Relationship between L-type Amino Acid Transporter 1 Expression and Liver Metastasis in T3 Colorectal Cancer. The Showa University Journal of Medical Sciences 23: 145-151.

Keyaerts M, Lahoutte T, Neyns B, Caveliers V, Vanhove C, Everaert H, et al. (2007). 123I-2-iodo-tyrosine, a new tumour imaging agent: human biodistribution, dosimetry and initial clinical evaluation in glioma patients. Eur J Nucl Med Mol Imaging 34: 994-1002.

(56) References Cited

OTHER PUBLICATIONS

Kim CH, Park KJ, Park JR, Kanai Y, Endou H, Park JC, et al. (2006a). The RNA interference of amino acid transporter LAT1 inhibits the growth of KB human oral cancer cells. Anticancer Res 26: 2943-2948.

Wang Q, Bailey CG, Ng C, Tiffen J, Thoeng A, Minhas V, et al. (2011). Androgen receptor and nutrient signaling pathways coordinate the demand for increased amino acid transport during prostate cancer progression. Cancer Res 71: 7525-7536.

Wang Q, Beaumont KA, Otte NJ, Font J, Bailey CG, van Geldermalsen M, et al. (2014). Targeting glutamine transport to suppress melanoma cell growth. Int J Cancer 135: 1060-1071.

Wang Q, Hardie RA, Hoy AJ, van Geldermalsen M, Gao D, Fazli L, et al. (2015). Targeting ASCT2-mediated glutamine uptake blocks prostate cancer growth and tumour development. J Pathol.

Watanabe J, Yokoyama Y, Futagami M, Mizunuma H, Yoshioka H, Washiya K, et al. (2014). L-type amino acid transporter 1 expression increases in well-differentiated but decreases in poorly differentiated endometrial endometrioid adenocarcinoma and shows an inverse correlation with p53 expression. Int J Gynecol Cancer 24: 559-663.

Wei L, Tominaga H, Ohgaki R, Wiriyasermkul P, Hagiwara K, Okuda S, et al. (2016). Specific transport of 3-fluoro-I-alpha-methyl-tyrosine by LAT1 explains its specificity to malignant tumors in imaging. Cancer Sci 107: 347-352.

Wieland H, Ullrich S, Lang F, Neumeister B (2005). Intracellular multiplication of Legionella pneumophila depends on host cell amino acid transporter SLC1A5. Mol Microbiol 55: 1528-1537.

Witte D, Ali N, Carlson N, Younes M (2002). Overexpression of the neutral amino acid transporter ASCT2 in human colorectal adenocarcinoma. Anticancer Res 22: 2555-2557.

Wongthai P, Hagiwara K, Miyoshi Y, Wiriyasermkul P, Wei L, Ohgaki R, et al. (2015). Boronophenylalanine, a boron delivery agent for boron neutron capture therapy, is transported by ATB0,+, LAT1 and LAT2. Cancer Sci 106: 279-286.

Xia H, Mao Q, Paulson HL, Davidson BL (2002). siRNA-mediated gene silencing in vitro and in vivo. Nat Biotechnol 20: 1006-1010.

Xu M, Sakamoto S, Matsushima J, Kimura T, Ueda T, Mizokami A, et al. (2016). Up-Regulation of LAT1 during Antiandrogen Therapy Contributes to Progression in Prostate Cancer Cells. J Urol 195: 1588-1597.

Yagita H, Masuko T, Hashimoto Y (1986). Inhibition of tumor cell growth in vitro by murine monoclonal antibodies that recognize a proliferation-associated cell surface antigen system in rats and humans. Cancer Res 46: 1478-1484.

Yanagida O, Kanai Y, Chairoungdua A, Kim DK, Segawa H, Nii T, et al. (2001). Human L-type amino acid transporter 1 (LAT1): characterization of function and expression in tumor cell lines. Biochim Biophys Acta 1514: 291-302.

Yanagisawa N, Hana K, Nakada N, Ichinoe M, Koizumi W, Endou H, et al. (2014). High expression of L-type amino acid transporter 1 as a prognostic marker in bile duct adenocarcinomas. Cancer Med 3: 1246-1255.

Yanagisawa N, Satoh T, Hana K, Ichinoe M, Nakada N, Endou H, et al. (2015). L-amino acid transporter 1 may be a prognostic marker for local progression of prostatic cancer under expectant management. Cancer Biomark 15: 365-374.

Yin Z, Jiang H, Syversen T, Rocha JB, Farina M, Aschner M (2008). The methylmercury-L-cysteine conjugate is a substrate for the L-type large neutral amino acid transporter. J Neurochem 107: 1083-1090.

Youland RS, Kitange GJ, Peterson TE, Pafundi DH, Ramiscal JA, Pokorny JL, et al. (2013). The role of LAT1 in (18) F-DOPA uptake in malignant gliomas. J Neurooncol 111: 11-18.

Yu JY, DeRuiter SL, Turner DL (2002). RNA interference by expression of short-interfering RNAs and hairpin RNAs in mammalian cells. Proc. Natl. Acad. Sci. USA 99: 6047-6052.

Zhou X, Zheng W, Nagana Gowda GA, Raftery D, Donkin SS, Bequette B, et al. (2016). 1,25-Dihydroxyvitamin D inhibits glutamine metabolism in Harvey-ras transformed MCF10A human breast epithelial cell. J Steroid Biochem Mol Biol 163: 147-156.

Baggetto, L. G. "Deviant energetic metabolism of glycolytic cancer cells." Biochimie 74.11 (1992): 959-974.

Christensen, Halvor N. "Role of amino acid transport and countertransport in nutrition and metabolism." Physiological reviews 70.1 (1990): 43-77.

Corbet, Cyril, et al. "Delivery of siRNA targeting tumor metabolism using non-covalent PEGylated chitosan nanoparticles: identification of an optimal combination of ligand structure, linker and grafting method." Journal of Controlled Release 223 (2016): 53-63.

Furugen, Ayako, et al. "Involvement of I-type amino acid transporter 1 in the transport of gabapentin into human placental choriocarcinoma cells." Reproductive Toxicology 67 (2017): 48-55.

Ichinoe, Masaaki, et al. "L-Type amino acid transporter 1 (LAT1) expression in lymph node metastasis of gastric carcinoma: Its correlation with size of metastatic lesion and Ki-67 labeling." Pathology-Research and Practice 211.7 (2015): 533-538.

Ichinoe, Masaaki, et al. "High expression of L-type amino-acid transporter 1 (LAT1) in gastric carcinomas: Comparison with non-cancerous lesions." Pathology international 61.5 (2011): 281-289.

Imai, Hisao, et al. "L-type amino acid transporter 1 expression is a prognostic marker in patients with surgically resected stage I non-small cell lung cancer." Histopathology 54.7 (2009): 804-813.

Kaira, Kyoichi, et al. "CD98 is a promising prognostic biomarker in biliary tract cancer." Hepatobiliary & Pancreatic Diseases International 13.6 (2014): 654-657.

Kaira, Kyoichi, et al. "Clinicopathological significance of ASC amino acid transporter-2 expression in pancreatic ductal carcinoma." Histopathology 66.2 (2015): 234-243.

Kaira, Kyoichi, et al. "L-type amino acid transporter 1 (LAT1) is frequently expressed in thymic carcinomas but is absent in thymomas." Journal of surgical oncology 99.7 (2009): 433-438.

Kaira, K, et al. "Prognostic significance of L-type amino acid transporter 1 expression in resectable stage I-III nonsmall cell lung cancer." British journal of cancer 98.4 (2008): 742.

Kaira, Kyoichi, et al. "CD98 expression is associated with poor prognosis in resected non-small-cell lung cancer with lymph node metastases." Annals of surgical oncology 16.12 (2009): 3473-3481.

Kaira, Kyoichi, et al. "Comparison of L-type amino acid transporter 1 expression and L-[3-18F]-a-methyl tyrosine uptake in outcome of non-small cell lung cancer." Nuclear medicine and biology 37.8 (2010): 911-916.

Kaira, Kyoichi, et al. "Expression of L-type amino acid transporter 1 (LAT1) in neuroendocrine tumors of the lung." Pathology-Research and Practice 204.8 (2008): 553-561.

Lee, Na-Young, et al. "The alteration of serine transporter activity in a cell line model of amyotrophic lateral sclerosis (ALS)." Biochemical and biophysical research communications 483.1 (2017): 135-141.

Namikawa, Masashi, et al. "Expression of amino acid transporters (LAT1, ASCT2 and xCT) as clinical significance in hepatocellular carcinoma." Hepatology Research 45.9 (2015): 1014-1022.

Medina, Miguel Ángel, Javier Márquez, and Ignacio Núñez. "Interchange of amino acids between tumor and host." Biochemical medicine and metabolic biology 48.1 (1992): 1-7.

Ohkame H, Masuda H, Ishii Y, Kanai Y (2001). Expression of L-type amino acid transporter 1 (LAT1) and 4F2 heavy chain (4F2hc) in liver tumor lesions of rat models. J Surg Oncol 78: 265-271; discussion 271-262.

Ohkawa, Mayumi, et al. "Oncogenicity of L-type amino-acid transporter 1 (LAT1) revealed by targeted gene disruption in chicken DT40 cells: LAT1 is a promising molecular target for human cancer therapy." Biochemical and biophysical research communications 406.4 (2011): 649-655.

Sakata, Takeshi, et al. "L-type amino-acid transporter 1 as a novel biomarker for high-grade malignancy in prostate cancer" Pathology international 59.1 (2009): 7-18.

Staka, Elisabeth, et al. "Mercury toxicokinetics of the healthy human term placenta involve amino acid transporters and ABC transporters." Toxicology 340 (2016): 34-42.

Takeuchi, Katsuyuki, et al. "LAT1 expression in non-small-cell lung carcinomas: analyses by semiquantitative reverse transcription-PCR (237 cases) and immunohistochemistry (295 cases)." Lung Cancer 68.1 (2010): 58-65.

(56) References Cited

OTHER PUBLICATIONS

Toyoda, Miroru, et al. "CD98 as a novel prognostic indicator for patients with stage III/IV hypopharyngeal squamous cell carcinoma." Head & neck 37.11 (2015): 1569-1574.
Luo, Xia, et al. "LAT1 regulates growth of uterine leiomyoma smooth muscle cells." Reproductive Sciences 17.9 (2010): 791-797.
Yamauchi, Kohichi, et al. "System L amino acid transporter inhibitor enhances anti-tumor activity of cisplatin in a head and neck squamous cell carcinoma cell line." Cancer letters 276.1 (2009): 95-101.
Yanagisawa, Nobuyuki, et al. "High expression of L-type amino acid transporter 1 (LAT1) predicts poor prognosis in pancreatic ductal adenocarcinomas." Journal of clinical pathology 65.11 (2012): 1019-1023.
Yoon, Jung Hoon, et al. "Amino acid transport system L is differently expressed in human normal oral keratinocytes and human oral cancer cells." Cancer letters 222.2 (2005): 237-245.
Kim CS, Cho SH, Chun HS, Lee SY, Endou H, Kanai Y, et al. (2008). BCH, an inhibitor of system L amino acid transporters, induces apoptosis in cancer cells. Biological & pharmaceutical bulletin 31: 1096-1100.
Kim DK, Ahn SG, Park JC, Kanai Y, Endou H, Yoon JH (2004a). Expression of L-type amino acid transporter 1 (LAT1) and 4F2 heavy chain (4F2hc) in oral squamous cell carcinoma and its precusor lesions. Anticancer Res 24: 1671-1675.
Kim HM, Lee YK, Koo JS (2016). Expression of glutamine metabolism-related proteins in thyroid cancer. Oncotarget.
Kim HM, Kim do H, Jung WH, Koo JS (2014). Metabolic phenotypes in primary unknown metastatic carcinoma. J Transl Med 12: 2.
Kim KD, Ahn SG, Park JC, Kanai Y, Endou H, Yoon JH (2004b). Expression of L-type amino acid transporter 1 (LAT1) and 4F2 heavy chain (4F2hc) in oral squamous cell carcinoma and its precusor lesions. Anticancer Res 24: 1671-1675.
Kim KD, Kanai Y, Choi HW, Tangtrongsup S, Chairoungdua A, Babu E, et al. (2002). Characterization of the system L amino acid transporter in T24 human bladder carcinoma cells. Biochim Biophys Acta 1565: 112-121.
Kim S, Jung WH, Koo JS (2013). The expression of glutamine-metabolism related proteins in breast phyllodes tumors. Tumour Biol 34: 2683-2689.
Kim SG, Kim HH, Kim HK, Kim CH, Chun HS, Kanai Y, et al. (2006b). Differential expression and functional characterization of system L amino acid transporters in human normal osteoblast cells and osteogenic sarcoma cells. Anticancer Res 26: 1989-1996.
Koo JS, Yoon JS (2015). Expression of metabolism-related proteins in lacrimal gland adenoid cystic carcinoma. Am J Clin Pathol 143: 584-592.
Kudo Y, Boyd CA (2004). RNA interference-induced reduction in CD98 expression suppresses cell fusion during syncytialization of human placental BeWo cells. FEBS Lett 577 473-477.
Kuhne A, Tzvetkov MV, Hagos Y, Lage H, Burckhardt G, Brockmoller J (2009). Influx and efflux transport as determinants of melphalan cytotoxicity: Resistance to melphalan in MDR1 overexpressing tumor cell lines. Biochem Pharmacol 78: 45-53.
Kuhne A, Kaiser R, Schirmer M, Heider U, Muhlke S, Niere W, et al. (2007). Genetic polymorphisms in the amino acid transporters LAT1 and LAT2 in relation to the pharmacokinetics and side effects of melphalan. Pharmacogenetics and genomics 17: 505-517.
Kyoichi K (2010). Prognostic significance of L-type amino acid transporter 1 (LAT1) and 4F2 heavy chain (CD98) expression in surgically resectable stage III non-small cell lung cancer. Experimental and Therapeutic Medicine 1: 799-808.
Lee NS, Dohjima T, Bauer G, Li H, Li M-J, Ehsani A, et al. (2002). Expression of small interfering RNAs targeted against HIV-1 rev transcripts in human cells. Nature Biotechnology 20: 500-505.
Li J, Qiang J, Chen SF, Wang X, Fu J, Chen Y (2013). The impact of L-type amino acid transporter 1 (LAT1) in human hepatocellular carcinoma. Tumour Biol 34: 2977-2981.

Li R, Younes M, Frolov A, Wheeler TM, Scardino P, Ohori M, et al. (2003). Expression of neutral amino acid transporter ASCT2 in human prostate. Anticancer Res 23: 3413-3418.
Li S, Whorton AR (2005). Identification of stereoselective transporters for S-nitroso-L-cysteine: role of LAT1 and LAT2 in biological activity of S-nitrosothiols. J Biol Chem 280: 20102-20110.
Liang Z, Cho HT, Williams L, Zhu A, Liang K, Huang K, et al. (2011). Potential Biomarker of L-type Amino Acid Transporter 1 in Breast Cancer Progression. Nucl Med Mol Imaging 45: 93-102.
Liu W, Chen H, Wong N, Haynes W, Baker CM, Wang X (2017). Pseudohypoxia induced by miR-126 deactivation promotes migration and therapeutic resistance in renal cell carcinoma. Cancer Lett 394: 65-75.
Liu, Y, Yang L, An H, Chang Y, Zhang W, Zhu Y, et al. (2015). High expression of Solute Carrier Family 1, member 5 (SLC1A5) is associated with poor prognosis in clear-cell renal cell carcinoma. Sci Rep 5: 16954.
Mazurek S, Eigenbrodt (2003). The tumor metabolome. Anticancer Res 23: 1149-1154.
Medina MA, Sanchez-Jimenez F, Marquez J, Rodriguez Quesada A, Nunez de Castro I (1992b). Relevance of glutamine metabolism to tumor cell growth. Mol Cell Biochem 113 1-15.
Miko E, Margitai Z, Czimmerer Z, Varkonyi I, Derso B, Lanyi A, et al. (2011). miR-126 inhibits proliferation of small cell lung cancer cells by targeting SLC7A5. FEBS Lett 585: 1191-1196.
Miyagishi M, Taira K (2002). U6 promoter-driven siRNAs with four uridine 3' overhangs efficiently suppress targeted gene expression in mammalian cells. Nature Biotechnology 19: 497-500.
Nakanishi K, Ogata S, Matsuo H, Kanai Y, Endou H, Hiroi S, et al. (2007). Expression of LAT1 predicts risk of progression of transitional cell carcinoma of the upper urinary tract. Virchows Arch 451: 681-690.
Nawashiro H, Otani N, Shinomiya N, Fukui S, Ooigawa H, Shima K, et al. (2006). L-type amino acid transporter 1 as a potential molecular target in human astrocytic tumors. Int J Cancer 119: 484-492.
Nicklin P, Bergman P, Zhang B, Triantafellow E, Wang H, Nyfeler B, et al. (2009). Bidirectional transport of amino acids regulates mTOR and autophagy. Cell 136: 521-534.
Nikkuni O, Kaira K, Toyoda M, Shino M, Sakakura K, Takahashi K, et al. (2015). Expression of Amino Acid Transporters (LAT1 and ASCT2) in Patients with Stage III/IV Laryngeal Squamous Cell Carcinoma. Pathol Oncol Res 21: 1175-1181.
Nobusawa A, Kim M, Kaira K, Miyashita G, Negishi A, Oriuchi N, et al. (2013). Diagnostic usefulness of (1)(8)F-FAMT PET and L-type amino acid transporter 1 (LAT1) expression in oral squamous cell carcinoma. Eur J Nucl Med Mol Imaging 40: 1692-1700.
Okubo S, Zhen HN, Kawai N, Nishiyama Y, Haba R, Tamiya T (2010). Correlation of L-methyl-11C-methionine (MET) uptake with L-type amino acid transporter 1 in human gliomas. J Neurooncol 99: 217-225.
Okudaira H, Shikano N, Nishii R, Miyagi T, Yoshimoto M, Kobayashi M, et al. (2011). Putative transport mechanism and intracellular fate of trans-1-amino-3-18F-fluorocyclobutanecarboxylic acid in human prostate cancer. J Nucl Med 52: 822-829.
Paddison PJ, Caudy AA, Bernstein E, Hannon GJ, Conklin DSS (2002). hort hairpin RNAs (shRNAs) induce sequence-specific silencing in mammalian cells. Genes Dev 16: 948-958.
Paul CP, Good PD, Winer I, Engelke DR (2002). Effective Expression of Small Interfering RNA in human cells. Nature Biotechnology 19: 505-508.
Pinho MJ, Serrao MP, Jose PA, Soares-da-Silva P (2007a). Overexpression of non-functional LAT1/4F2hc in renal proximal tubular epithelial cells from the spontaneous hypertensive rat. Cell Physiol Biochem 20: 535-548.
Pinho MJ, Pinto V, Serrao MP, Jose PA, Soares-da-Silva P (2007b). Underexpression of the Na+-dependent neutral amino acid transporter ASCT2 in the spontaneously hypertensive rat kidney. Am J Physiol Regul Integr Comp Physiol 293: R538-R547.
Polet F, Martherus R, Corbet C, Pinto A, Feron O (2016). Inhibition of glucose metabolism prevents glycosylation of the glutamine transporter ASCT2 and promotes compensatory LAT1 upregulation in leukemia cells. Oncotarget 7: 46371-46383.

(56) References Cited

OTHER PUBLICATIONS

Ren P, Yue M, Xiao D, Xiu R, Gan L, Liu H, et al. (2015). ATF4 and N-Myc coordinate glutamine metabolism in MYCN-amplified neuroblastoma cells through ASCT2 activation. J Pathol 235: 90-100.

Sang J, Lim YP, Panzica M, Finch P, Thompson NL (1995). TA1, a highly conserved oncofetal complementary DNA from rat hepatoma, encodes an integral membrane protein associated with liver development, carcinogenesis, and cell activation. Cancer Res 55: 1152-1159.

Segawa A, Nagamori S, Kanai Y, Masawa N, Oyama T (2013). L-type amino acid transporter 1 expression is highly correlated with Gleason score in prostate cancer. Mol Clin Oncol 1: 274-280.

Shennan DB, Thomson J (2008). Inhibition of system L (LAT1/CD98hc) reduces the growth of cultured human breast cancer cells. Oncology reports 20: 885-889.

Shennan DB, Thomson J, Gow IF, Travers MT, Barber MC (2004). L-leucine transport in human breast cancer cells (MCF-7 and MDA-MB-231): kinetics, regulation by estrogen and molecular identity of the transporter. Biochim Biophys Acta 1664: 206-216.

Shimizu K, Kaira K, Tomizawa Y, Sunaga N, Kawashima O, Oriuchi N, et al. (2014). ASC amino-acid transporter 2 (ASCT2) as a novel prognostic marker in non-small cell lung cancer. Br J Cancer 110: 2030-2039.

Stockhammer F, Plotkin M, Amthauer H, van Landeghem FK, Woiciechowsky C (2008). Correlation of F-18-fluoro-ethyl-tyrosin uptake with vascular and cell density in non-contrast-enhancing gliomas. J Neurooncol 88: 205-210.

Storey BT, Fugere C, Lesieur-Brooks A, Vaslet C, Thompson NL (2005). Adenoviral modulation of the tumor-associated system L amino acid transporter, LAT1, alters amino acid transport, cell growth and 4F2/CD98 expressionwith cell-type specific effects in cultured hepatic cells. Int J Cancer 117: 387-397.

Sui G, Soohoo C, Affar EB, Gay F, Shi Y, Forrester WC, et al. (2002). A DNA vector-based RNAi technology to suppress gene expression in mammalian cells. Proc Natl Acad Sci USA 99: 5515-5520.

Suzuki S, Kaira K, Ohshima Y, Ishioka NS, Sohda M, Yokobori T, et al. (2014). Biological significance of fluorine-18-alpha-methyltyrosine (FAMT) uptake on PET in patients with oesophageal cancer. Br J Cancer 110: 1985-1991.

Tamai S, Masuda H, Ishii Y, Suzuki S, Kanai Y, Endou H (2001). Expression of L-type amino acid transporter 1 in a rat model of liver metastasis: positive correlation with tumor size. Cancer Detect Prev 25: 439-445.

Tomblin JK, Arthur S, Primerano DA, Chaudhry AR, Fan J, Denvir J, et al. (2016). Aryl hydrocarbon receptor (AHR) regulation of L-Type Amino Acid Transporter 1 (LAT-1) expression in MCF-7 and MDA-MB-231 breast cancer cells. Biochem Pharmacol 106: 94-103.

Toyoda M, Kaira K, Ohshima Y, Ishioka NS, Shino M, Sakakura K, et al. (2014a). Prognostic significance of amino-acid transporter expression (LAT1, ASCT2, and xCT) in surgically resected tongue cancer. Br J Cancer 110: 2506-2513.

Toyoda M, Kaira K, Shino M, Sakakura K, Takahashi K, Takayasu Y, et al. (2014b). CD98 as a novel prognostic indicator for patients with stage III/IV hypopharyngeal squamous cell carcinoma. Head Neck: 1-6.

* cited by examiner

Figure 1
A
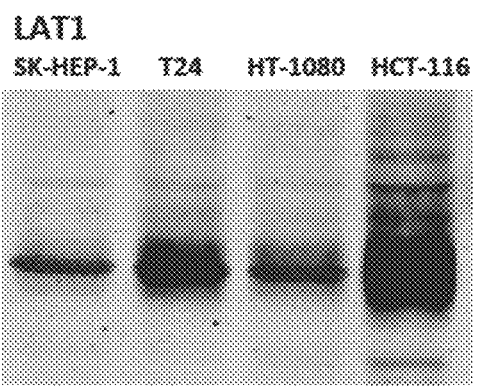
B
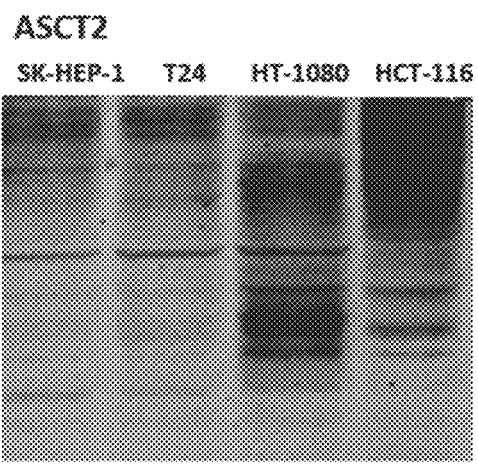

Figure 6

SEQ ID NOS 58/162/411
```
5'  CTTCGCCACCTACCTGCTCAA   (5' DNA sense)          SEQ ID NO: 58
    |||||||||||||||||||||
5'  CUUCGCCACCUACCUGCUCAA   (5' sense siRNA)        SEQ ID NO: 162
    |||||||||||||||||||||
3'  GAAGCGGUGGAUGGACGAGUU   (3' antisense siRNA)    SEQ ID NO: 411
```

SEQ ID NOS 58/387/388
```
5'      CTTCGCCACCTACCTGCTCAA       (5' DNA sense)          SEQ ID NO: 58
        |||||||||||||||||||||
5'      CUUCGCCACCUACCUGCUCAAdTdT   (5' sense siRNA)        SEQ ID NO: 387
        |||||||||||||||||||||
3' dTdTGAAGCGGUGGAUGGACGAGUU        (3' antisense siRNA)    SEQ ID NO: 388
```

SEQ ID NOS 58/389/390
```
5'  CTTCGCCACCTACCTGCTCAA       (5' DNA sense)          SEQ ID NO: 58
      |||||||||||||||||||
5'    UCGCCACCUACCUGCUCAAdTdT   (5' sense siRNA)        SEQ ID NO: 389
      |||||||||||||||||||
3'dTdTAGCGGUGGAUGGACGAGUU       (3' antisense siRNA)    SEQ ID NO: 390
```

SEQ ID NOS 58/389/412
```
5'  CTTCGCCACCTACCTGCTCAA       (5' DNA sense)          SEQ ID NO: 58
      |||||||||||||||||||
5'    UCGCCACCUACCUGCUCAAdTdT   (5' sense siRNA)        SEQ ID NO: 389
      |||||||||||||||||||
3'  GUAGCGGUGGAUGGACGAGUU       (3' antisense siRNA)    SEQ ID NO: 412
```

SEQ ID NOS 61/165/396
```
5'  CGTGAACTGCTACAGCGTGAA   (5' DNA sense)       SEQ ID NO: 61
    |||||||||||||||||||||
5'  CGUGAACUGCUACAGCGUGAA   (5' sense)           SEQ ID NO: 165
    |||||||||||||||||||||
3'  GCACUUGACGAUGUCUCACUU   (3' antisense)       SEQ ID NO: 396
```

SEQ ID NOS 61/391/392
```
5'      CGTGAACTGCTACAGCGTGAA       (5' DNA sense)    SEQ ID NO: 61
        |||||||||||||||||||||
5'      CGUGAACUGCUACAGCGUGAAdTdT   (5' sense)        SEQ ID NO: 391
        |||||||||||||||||||||
3' dTdTGCACUUGACGAUGUCUCACUU        (3' antisense)    SEQ ID NO: 392
```

SEQ ID NOS 61/393/394
```
5'  CGTGAACTGCTACAGCGTGAA       (5' DNA sense)    SEQ ID NO: 61
      |||||||||||||||||||
5'    UGAACUGCUACAGCGUGAAdTdT   (5' sense)        SEQ ID NO: 393
      |||||||||||||||||||
3'dTdTACUUGACGAUGUCUCACUU       (3' antisense)    SEQ ID NO: 394
```

SEQ ID NOS 61/395/396
```
5'  CGTGAACTGCTACAGCGTGAA       (5' DNA sense)    SEQ ID NO: 61
      |||||||||||||||||||
5'    UGAACUGCUACAGCGUGAAdTdT   (5' sense)        SEQ ID NO: 395
      |||||||||||||||||||
3'  GCACUUGACGAUGUCUCACUU       (3' antisense)    SEQ ID NO: 396
```

Figure 7

```
SEQ ID NOS 267/356/402
5'  CCGGTCCTGTACCGTCCTCAA   (5' DNA sense)    SEQ ID NO: 267
    |||||||||||||||||||||
5'  CCGGUCCUGUACCGUCCUCAA   (5' sense)        SEQ ID NO: 356
    |||||||||||||||||||||
3'  GGCCAGGACAUGGCAGGAGUU   (3' antisense)    SEQ ID NO: 402

SEQ ID NOS 267/397/398
5'      CCGGTCCTGTACCGTCCTCAA        (5' DNA sense)    SEQ ID NO: 267
        |||||||||||||||||||||
5'      CCGGUCCUGUACCGUCCUCAAdTdT    (5' sense)        SEQ ID NO: 397
        |||||||||||||||||||||
3'  dTdTGGCCAGGACAUGGCAGGAGUU        (3' antisense)    SEQ ID NO: 398

SEQ ID NOS 267/399/400
5'  CCGGTCCTGTACCGTCCTCAA        (5' DNA sense)    SEQ ID NO: 267
    |||||||||||||||||||||
5'     GGUCCUGUACCGUCCUCAAdTdT   (5' sense)        SEQ ID NO: 399
       |||||||||||||||||||
3'dTdTCCAGGACAUGGCAGGAGUU        (3' antisense)    SEQ ID NO: 400

SEQ ID NOS 267/401/402
5'  CCGGTCCTGTACCGTCCTCAA        (5' DNA sense)    SEQ ID NO: 267
    |||||||||||||||||||||
5'     GGUCCUGUACCGUCCUCAAdTdT   (5' sense)        SEQ ID NO: 401
       |||||||||||||||||||
3'  GGCCAGGACAUGGCAGGAGUU        (3' antisense)    SEQ ID NO: 402

SEQ ID NOS 278/367/408
5'  TGCCACGGTCGCCTCTGAGAA   (5' DNA sense)    SEQ ID NO: 278
    |||||||||||||||||||||
5'  UGCCACGGUCGCCUCUGAGAA   (5' sense)        SEQ ID NO: 367
    |||||||||||||||||||||
3'  ACGGUGCCAGCGGAGACUCUU   (3' antisense)    SEQ ID NO: 408

SEQ ID NOS 278/403/404
5'      TGCCACGGTCGCCTCTGAGAA        (5' DNA sense)    SEQ ID NO: 278
        |||||||||||||||||||||
5'      UGCCACGGUCGCCUCUGAGAAdTdT    (5' sense)        SEQ ID NO: 403
        |||||||||||||||||||||
3'  dTdTACGGUGCCAGCGGAGACUCUU        (3' antisense)    SEQ ID NO: 404

SEQ ID NOS 278/405/406
5'  TGCCACGGTCGCCTCTGAGAA        (5' DNA sense)    SEQ ID NO: 278
    |||||||||||||||||||||
5'    CCACGGUCGCCUCUGAGAAdTdT    (5' sense)        SEQ ID NO: 405
      |||||||||||||||||||
3'dTdTGGUGCCAGCGGAGACUCUU        (3' antisense)    SEQ ID NO: 406

SEQ ID NOS 278/407/408
5'  TGCCACGGTCGCCTCTGAGAA        (5' DNA sense)    SEQ ID NO: 278
    |||||||||||||||||||||
5'    CCACGGUCGCCUCUGAGAAdTdT    (5' sense)        SEQ ID NO: 407
      |||||||||||||||||||
3'  ACGGUGCCAGCGGAGACUCUU        (3' antisense)    SEQ ID NO: 408
```

Figure 8
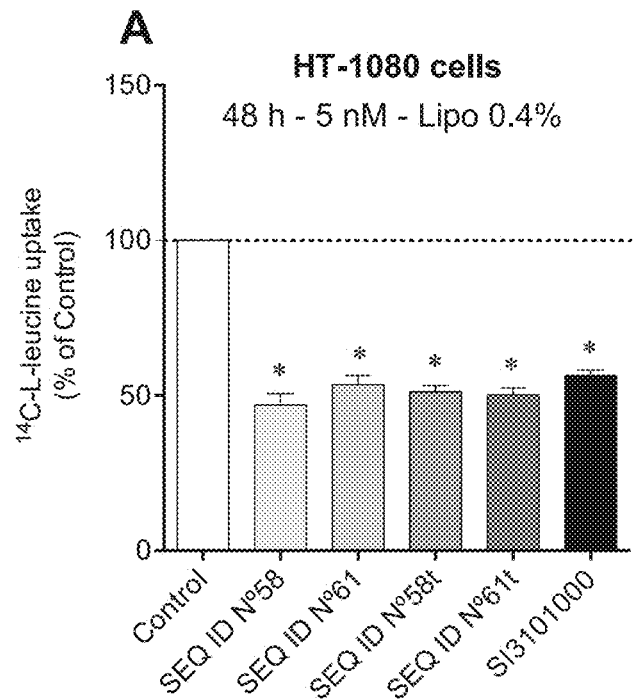
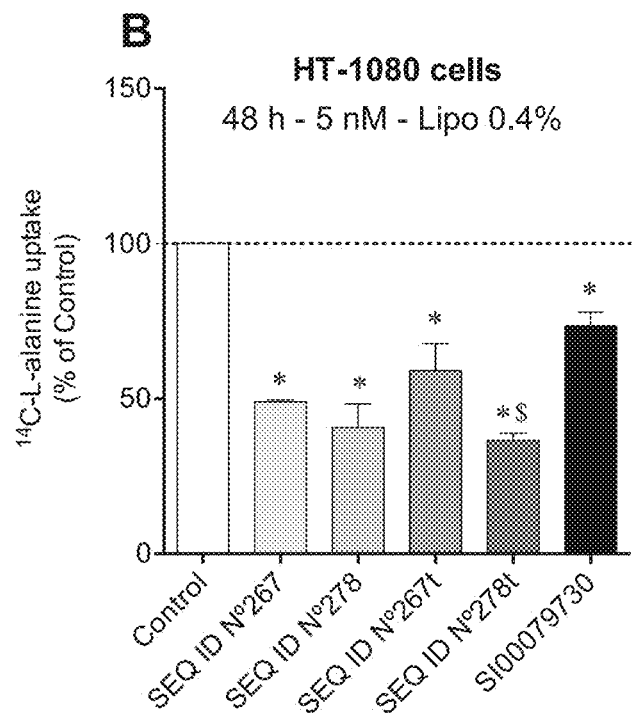

Figure 10
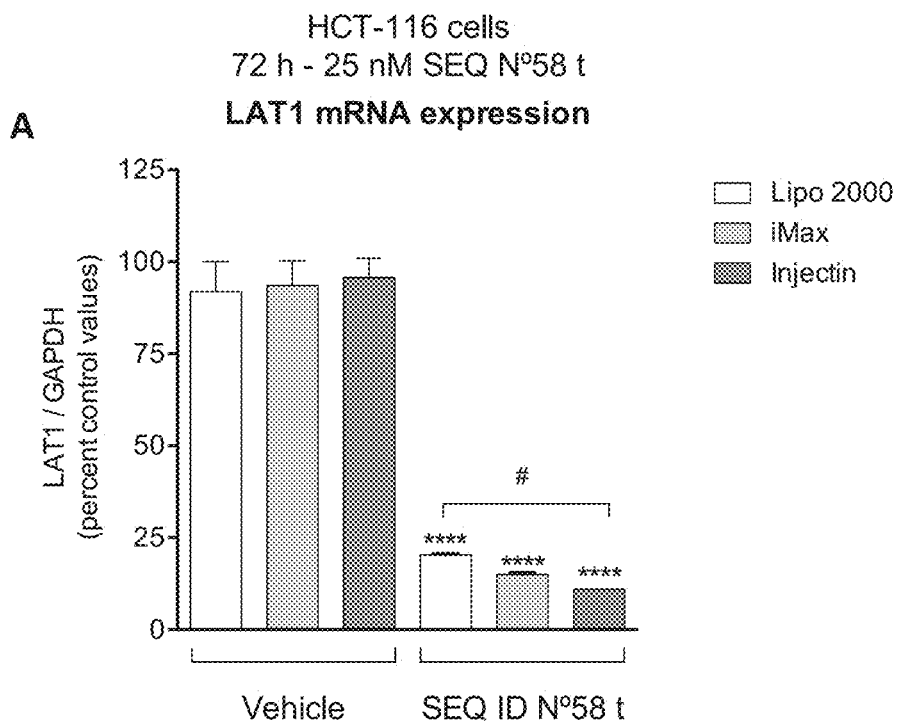
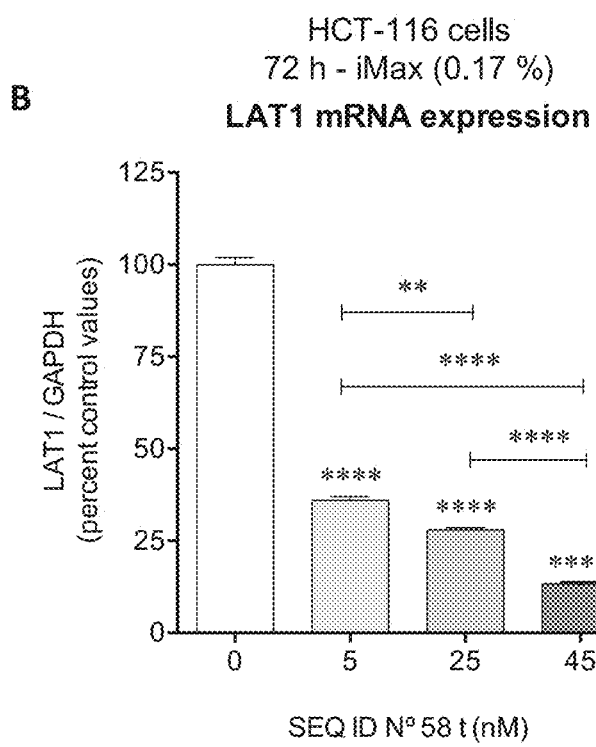

Figure 17
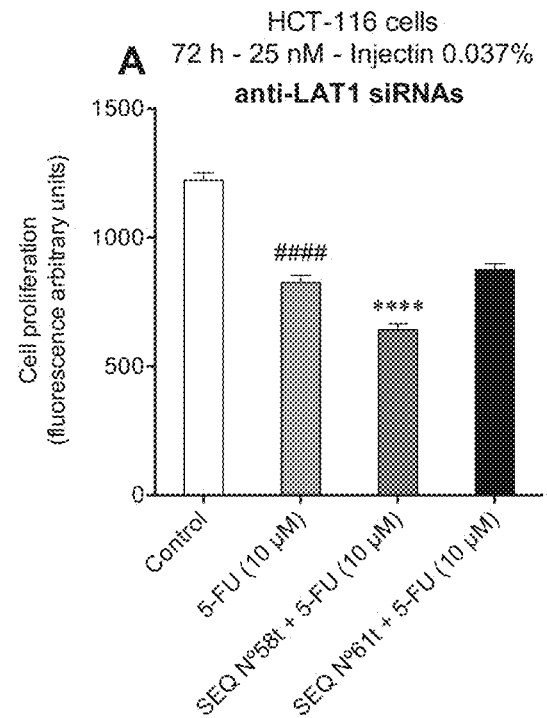
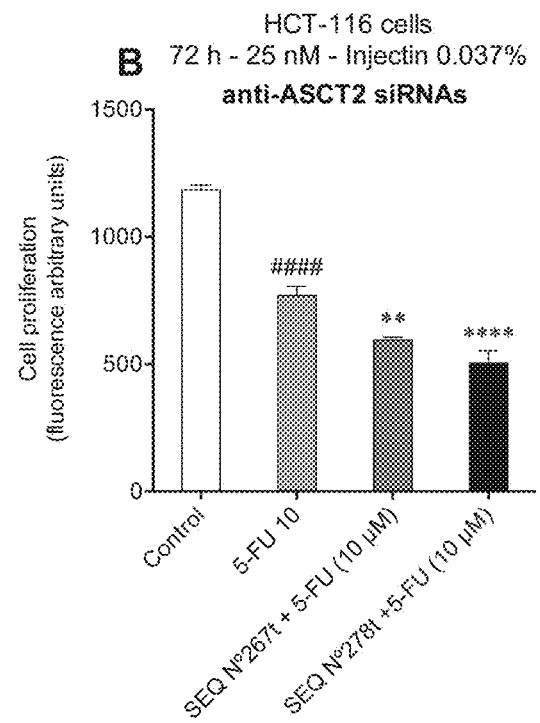

Figure 18
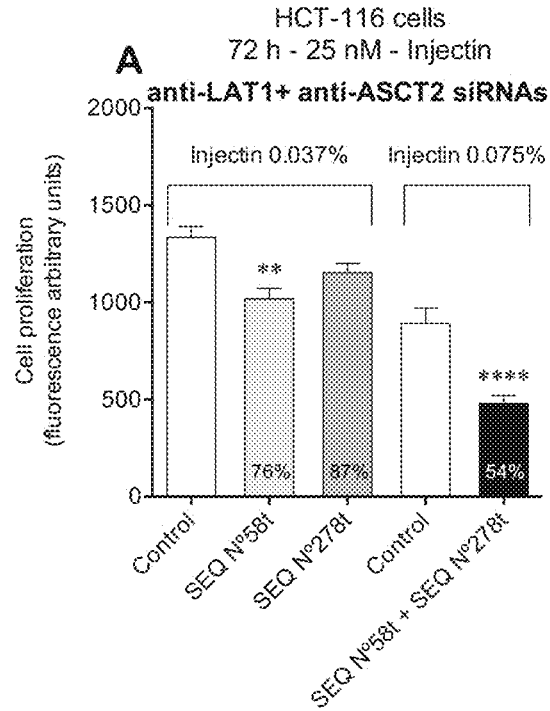
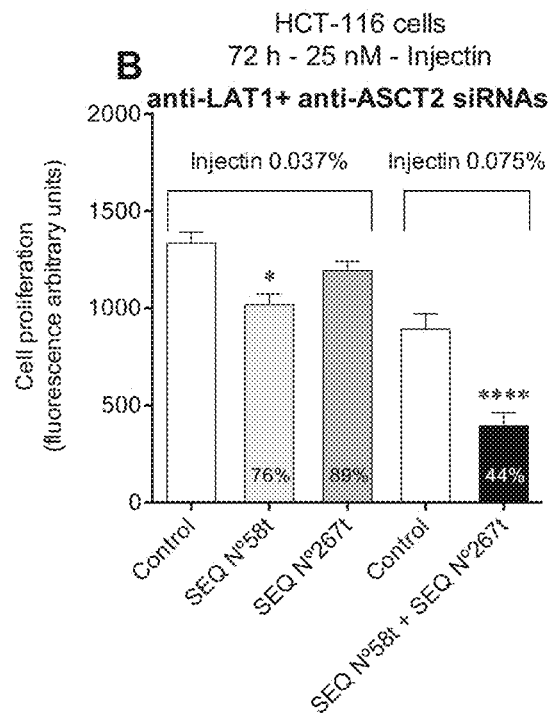

Figure 24

Most preferred LAT1 sequences of Homo sapiens solute carrier family 7 member 5 (SLC7A5), mRNA, LOCUS NM_003486, according version NM_003486.5, posted 20-FEB-2016.

| SEQ ID № | Target sequence | Position* | Nucleotides |
|---|---|---|---|
| 1 | AAGCGGCGCGCGCTAGCGGCG | 91-111 | 21 |
| 48 | GGCGCCGGCGGCCGAGGAGAA | 108-128 | 21 |
| 49 | CCGGCGGCCGAGGAGAAGGAA | 112-132 | 21 |
| 4 | AAGATGCTGGCCGCCAAGAGC | 145-165 | 21 |
| 5 | AAGAGCGCGGACGGCTCGGCG | 160-180 | 21 |
| 6 | AACATCACGCTGCTCAACGGC | 217-237 | 21 |
| 55 | GCTCGGCACCACCATCTCCAA | 387-407 | 21 |
| 56 | CTCGGCACCACCATCTCCAAA | 388-408 | 21 |
| 10 | AAGCTCTGGATCGAGCTGCTC | 466-486 | 21 |
| 58 | CTTCGCCACCTACCTGCTCAA | 525-545 | 21 |
| 12 | AAGCTCGTGGCCTGCCTCTGC | 586-606 | 21 |
| 60 | GCTGCTGCTCACGGCCGTGAA | 609-629 | 21 |
| 61 | CGTGAACTGCTACAGCGTGAA | 624-644 | 21 |
| 13 | AACTGCTACAGCGTGAAGGCC | 628-648 | 21 |
| 19 | AAGGCACCAAACTGGATGTGG | 773-793 | 21 |
| 22 | AACATTGTGCTGGCATTATAC | 796-816 | 21 |
| 71 | TGGAGGATGGAATTACTTGAA | 834-854 | 21 |
| 73 | CGTCACAGAGGAAATGATCAA | 858-878 | 21 |
| 76 | GCTGGTGTACGTGCTGACCAA | 930-950 | 21 |
| 78 | GTCCTGCTTCGGCTCCGTCAA | 1071-1091 | 21 |
| 80 | GCTGCTCTACGCCTTCTCCAA | 1224-1244 | 21 |
| 34 | AAGGACATCTTCTCCGTCATC | 1243-1263 | 21 |
| 81 | GGACATCTTCTCCGTCATCAA | 1245-1265 | 21 |
| 82 | CAACTTCTTCAGCTTCTTCAA | 1263-1283 | 21 |
| 35 | AACTTCTTCAGCTTCTTCAAC | 1264-1284 | 21 |
| 83 | TGATCGGCTGCGCCACAGAA | 1316-1336 | 21 |
| 84 | GATCTGGCTGCGCCACAGAAA | 1317-1337 | 21 |
| 37 | AAAGCCTGAGCTTGAGCGGCC | 1335-1355 | 21 |
| 87 | GATCGCCGTCTCCTTCTGGAA | 1410-1430 | 21 |
| 94 | CACGACCGTCCTGTGTCAGAA | 1545-1565 | 21 |

Figure 25
Most preferred sequences of Homo sapiens solute carrier family 1 member 5 (SLC1A5), transcript variant 3, mRNA, LOCUS NM_001145145, according version NM_001145145.1, posted 27-MAY-2017.

| SEQ ID № | Target sequence | Position | Nucleotides |
|---|---|---|---|
| 209 | AAGAGAGGAATATCACCGGAA | 300-320 | 21 |
| 251 | CCGCTTCTTCAACTCCTTCAA | 442-462 | 21 |
| 216 | AACTCCTTCAATGAGGCCACC | 452-472 | 21 |
| 217 | AATGAGGCCACCATGGTTCTG | 461-481 | 21 |
| 252 | CATGTTCCTGGTGGCTGGCAA | 517-537 | 21 |
| 218 | AAGATCGTGGAGATGGAGGAT | 536-556 | 21 |
| 219 | AAGTACATTCTGTGCTGCCTG | 584-684 | 21 |
| 257 | CACGCTGCCGCTGATGATGAA | 739-759 | 21 |
| 224 | AAGTGCGTGGAGGAGAATAAT | 758-778 | 21 |
| 225 | AATAATGGCGTGGCCAAGCAC | 773-793 | 21 |
| 258 | GATGAAGTGCGTGGAGGAGAA | 754-774 | 21 |
| 259 | GAAGTGCGTGGAGGAGAATAA | 757-777 | 21 |
| 226 | AATGGCGTGGCCAAGCACATC | 776-796 | 21 |
| 260 | GGAGAATAATGGCGTGGCCAA | 769-789 | 21 |
| 228 | AACATGGACGGTGCCGCGCTC | 830-850 | 21 |
| 263 | AGCAGTCCTTGGACTTCGTAA | 891-991 | 21 |
| 262 | GCAGTCCTTGGACTTCGTAAA | 892-912 | 21 |
| 229 | AAAGATCATCACCATCCTGGT | 910-930 | 21 |
| 230 | AAGATCATCACCATCCTGGTC | 911-931 | 21 |
| 265 | ACTCTGGCCATCATCCTCGAA | 986-1006 | 21 |
| 264 | CATCATCCTCGAAGCAGTCAA | 994-1014 | 21 |
| 267 | CCGGTCCTGTACCGTCCTCAA | 1066-1086 | 21 |
| 266 | TGTACCGTCCTCAATGTAGAA | 1073-1093 | 21 |
| 235 | AAAATTACGTGGACCGTACGG | 1122-1142 | 21 |
| 236 | AAATTACGTGGACCGTACGGA | 1123-1143 | 21 |
| 237 | AATTACGTGGACCGTACGGAG | 1124-1144 | 21 |
| 271 | TGGACCGTACGGAGTCGAGAA | 1131-1151 | 21 |
| 238 | AAGCACAGAGCCTGAGTTGAT | 1150-1170 | 21 |
| 272 | ACAGAGCCTGAGTTGATACAA | 1154-1174 | 21 |
| 273 | GCCTGAGTTGATACAAGTGAA | 1159-1179 | 21 |
| 278 | TGCCACGGTCGCCTCTGAGAA | 1264-1284 | 21 |
| 279 | ACGGTCGCCTCTGAGAAGGAA | 1268-1288 | 21 |
| 280 | GAGAAGGAATCAGTCATGTAA | 1280-1300 | 21 |

Figure 26A

| SEQ ID No | nucleotide | Sequences of interest | LAT 1 siRNA | | |
|---|---|---|---|---|---|
| | | human mRNA target sequence | | 5' sense | 5' anti-sense |
| SEQ ID NO 1 | 21 | aagcggcgcgcgctagcggcg | SEQ ID NO 105 | AAGCGGCGCGCGCUAGCGGCG | CGCCGCUAGCGCGCCGCUU |
| SEQ ID NO 2 | 21 | aaggaagaggcgcgggagaag | SEQ ID NO 106 | AAGGAAGAGGCGCGGGAGAAG | CUUCUCCCGCGCCUCUUCCUU |
| SEQ ID NO 3 | 21 | aagaggcgcggagaagatgc | SEQ ID NO 107 | AAGAGGCGCGGGAGAAGAUGC | GCAUCUUCUCCCGCGCCUCUU |
| SEQ ID NO 4 | 21 | aagatgctggccgccaagagc | SEQ ID NO 108 | AAGAUGCUGGCCGCCAAGAGC | GCUCUUGGCGGCCAGCAUCUU |
| SEQ ID NO 5 | 21 | aagagcgcggacggctcggcg | SEQ ID NO 109 | AAGAGCGCGGACGGCUCGGCG | CGCCGAGCCGUCCGCGCUCUU |
| SEQ ID NO 6 | 21 | aacatcacgctgctcaacggc | SEQ ID NO 110 | AACAUCACGCUGCUCAACGGC | GCCGUUGAGCAGCGUGAUGUU |
| SEQ ID NO 7 | 21 | aaggaggcaggctcgccggg | SEQ ID NO 111 | AAGGAGGCAGGCUCGCCGGGG | CCCCGGCGAGCCUGCCUCCUU |
| SEQ ID NO 8 | 21 | aaatcgggcggcgactacgcc | SEQ ID NO 112 | AAAUCGGGCGGCGACUACGCC | GGCGUAGUCGCCGCCCGAUUU |
| SEQ ID NO 9 | 21 | aatcgggcggcgactacgcct | SEQ ID NO 113 | AAUCGGGCGGCGACUACGCCU | AGGCGUAGUCGCCGCCCGAUU |
| SEQ ID NO 10 | 21 | aagctctggatcgagctgctc | SEQ ID NO 114 | AAGCUCUGGAUCGAGCUGCUC | GAGCAGCUCGAUCCAGAGCUU |
| SEQ ID NO 11 | 21 | aagccgctcttccccacctgc | SEQ ID NO 115 | AAGCCGCUCUUCCCCACCUGC | GCAGGUGGGGAAGAGCGGCUU |
| SEQ ID NO 12 | 21 | aagctcgtggcctgcctctgc | SEQ ID NO 116 | AAGCUCGUGGCCUGCCUCUGC | GCAGAGGCAGGCCACGAGCUU |
| SEQ ID NO 13 | 21 | aactgctacagcgtgaaggcc | SEQ ID NO 117 | AACUGCUACAGCGUGAAGGCC | GGCCUUCACGCUGUAGCAGUU |
| SEQ ID NO 14 | 21 | aaggccgccacccgggtccag | SEQ ID NO 118 | AAGGCCGCCACCCGGGUCCAG | CUGGACCCGGGUGGCGGCCUU |
| SEQ ID NO 15 | 21 | aagctcctggccctggccctg | SEQ ID NO 119 | AAGCUCCUGGCCCUGGCCCUG | CAGGGCCAGGGCCAGGAGCUU |
| SEQ ID NO 16 | 21 | aagggtgatgtgtccaatcta | SEQ ID NO 120 | AAGGGUGAUGUGUCCAAUCUA | UAGAUUGGACACAUCACCCUU |
| SEQ ID NO 17 | 21 | aatctagatcccaacttctca | SEQ ID NO 121 | AAUCUAGAUCCCAACUUCUCA | UGAGAAGUUGGGAUCUAGAUU |
| SEQ ID NO 18 | 21 | aacttctcatttgaaggcacc | SEQ ID NO 122 | AACUUCUCAUUUGAAGGCACC | GGUGCCUUCAAAUGAGAAGUU |
| SEQ ID NO 19 | 21 | aaggcaccaaactggatgtgg | SEQ ID NO 123 | AAGGCACCAAACUGGAUGUGG | CCACAUCCAGUUUGGUGCCUU |
| SEQ ID NO 20 | 21 | aaaactggatgtggggaacatt | SEQ ID NO 124 | AAACUGGAUGUGGGGAACAUU | AAUGUUCCCCACAUCCAGUUU |
| SEQ ID NO 21 | 21 | aactggatgtggggaacattg | SEQ ID NO 125 | AACUGGAUGUGGGGAACAUUG | CAAUGUUCCCCACAUCCAGUU |
| SEQ ID NO 22 | 21 | aacattgtgctggcattatac | SEQ ID NO 126 | AACAUUGUGCUGGCAUUAUAC | GUAUAAUGCCAGCACAAUGUU |
| SEQ ID NO 23 | 21 | aattacttgaatttcgtcaca | SEQ ID NO 127 | AAUUACUUGAAUUUCGUCACA | UGUGACGAAAUUCAAGUAAUU |
| SEQ ID NO 24 | 21 | aatttcgtcacagaggaaatg | SEQ ID NO 128 | AAUUUCGUCACAGAGGAAAUG | CAUUUCCUCUGUGACGAAAUU |
| SEQ ID NO 25 | 21 | aaatgatcaaccctacagaa | SEQ ID NO 129 | AAAUGAUCAACCCCUACAGAA | UUCUGUAGGGGUUGAUCAUUU |
| SEQ ID NO 26 | 21 | aatgatcaaccctacagaaa | SEQ ID NO 130 | AAUGAUCAACCCCUACAGAAA | UUUCUGUAGGGGUUGAUCAUU |
| SEQ ID NO 27 | 21 | aaccctacagaaacctgccc | SEQ ID NO 131 | AACCCUACAGAAACCUGCCC | GGGCAGGUUUCUGUAGGGGUU |
| SEQ ID NO 28 | 21 | aaacctgcccctggccatcat | SEQ ID NO 132 | AAACCUGCCCCUGGCCAUCAU | AUGAUGGCCAGGGGCAGGUUU |
| SEQ ID NO 29 | 21 | aacctgcccctggccatcatc | SEQ ID NO 133 | AACCUGCCCCUGGCCAUCAUC | GAUGAUGGCCAGGGGCAGGUU |
| SEQ ID NO 30 | 21 | aacctggcctacttcaccacc | SEQ ID NO 134 | AACCUGGCCUACUUCACCACC | GGUGGUGAAGUAGGCCAGGUU |

Figure 26B

| SEQ ID NO 31 | 21 | aactatcacctgggcgtcatg | SEQ ID NO 135 | AACUAUCACCUGGGCGUCAUG | CAUGACGCCCAGGUGAUAGUU |
|---|---|---|---|---|---|
| SEQ ID NO 32 | 21 | aatgggtccctgttcacatcc | SEQ ID NO 136 | AAUGGGUCCCUGUUCACAUCC | GGAUGUGAACAGGGACCCAUU |
| SEQ ID NO 33 | 21 | aaggccacctgccctccatcc | SEQ ID NO 137 | AAGGCCACCUGCCCUCCAUCC | GGAUGGAGGGCAGGUGGCCUU |
| SEQ ID NO 34 | 21 | aaggacatcttctccgtcatc | SEQ ID NO 138 | AAGGACAUCUUCUCCGUCAUC | GAUGACGGAGAAGAUGUCCUU |
| SEQ ID NO 35 | 21 | aacttcttcagcttcttcaac | SEQ ID NO 139 | AACUUCUUCAGCUUCUUCAAC | GUUGAAGAAGCUGAAGAAGUU |
| SEQ ID NO 36 | 21 | aactggctctgcgtggccctg | SEQ ID NO 140 | AACUGGCUCUGCGUGGCCCUG | CAGGGCCACGCAGAGCCAGUU |
| SEQ ID NO 37 | 21 | aaagcctgagcttgagcggcc | SEQ ID NO 141 | AAAGCCUGAGCUUGAGCGGCC | GGCCGCUCAAGCUCAGGCUUU |
| SEQ ID NO 38 | 21 | aagcctgagcttgagcggccc | SEQ ID NO 142 | AAGCCUGAGCUUGAGCGGCCC | GGGCCGCUCAAGCUCAGGCUU |
| SEQ ID NO 39 | 21 | aaggtgaacctggccctgcct | SEQ ID NO 143 | AAGGUGAACCUGGCCCUGCCU | AGGCAGGGCCAGGUUCACCUU |
| SEQ ID NO 40 | 21 | aacctggccctgcctgtgtc | SEQ ID NO 144 | AACCUGGCCCUGCCUGUGUUC | GAACACAGGCAGGGCCAGGUU |
| SEQ ID NO 41 | 21 | aagcacccgtggagtgtggc | SEQ ID NO 145 | AAGCACCCGUGGAGUGUGGC | GCCACACUCCACGGGUGCUUU |
| SEQ ID NO 42 | 21 | aaaaacaagcccaagtggctc | SEQ ID NO 146 | AAAAACAAGCCCAAGUGGCUC | GAGCCACUUGGGCUUGUUUUU |
| SEQ ID NO 43 | 21 | aaacaagcccaagtggctcct | SEQ ID NO 147 | AAACAAGCCCAAGUGGCUCCU | AGGAGCCACUUGGGCUUGUUU |
| SEQ ID NO 44 | 21 | aacaagcccaagtggctcctc | SEQ ID NO 148 | AACAAGCCCAAGUGGCUCCUC | GAGGAGCCACUUGGGCUUGUU |
| SEQ ID NO 45 | 21 | aagcccaagtggctcctccag | SEQ ID NO 149 | AAGCCCAAGUGGCUCCUCCAG | CUGGAGGAGCCACUUGGGCUU |
| SEQ ID NO 46 | 21 | aagtggctcctccagggcatc | SEQ ID NO 150 | AAGUGGCUCCUCCAGGGCAUC | GAUGCCCUGGAGGAGCCACUU |
| SEQ ID NO 47 | 21 | aagctcatgcaggtggtccc | SEQ ID NO 151 | AAGCUCAUGCAGGUGGUCCCC | GGGGACCACCUGCAUGAGCUU |
| SEQ ID NO 48 | 21 | ggcgccggcggccgaggagaa | SEQ ID NO 152 | GGCGCCGGCGGCCGAGGAGAA | UUCUCCUCGGCCGCCGGCGCC |
| SEQ ID NO 49 | 21 | ccggcgccgaggagaaggaa | SEQ ID NO 153 | CCGGCGGCCGAGGAGAAGGAA | UUCCUUCUCCUCGGCCGCCGG |
| SEQ ID NO 50 | 21 | ggagaagatgctggccgccaa | SEQ ID NO 154 | GGAGAAGAUGCUGGCCGCCAA | UUGGCGGCCAGCAUCUUCUCC |
| SEQ ID NO 51 | 21 | gaaggaagaggcgcgggagaa | SEQ ID NO 155 | GAAGGAAGAGGCGCGGGAGAA | UUCUCCCGCGCCUCUUCCUUC |
| SEQ ID NO 52 | 21 | ggagaagatgctggccgccaa | SEQ ID NO 156 | GGAGAAGAUGCUGGCCGCCAA | UUGGCGGCCAGCAUCUUCUCC |
| SEQ ID NO 53 | 21 | gggcgtgaccctgcagcggaa | SEQ ID NO 157 | GGGCGUGACCCUGCAGCGGAA | UUCCGCUGCAGGGUCACGCCC |
| SEQ ID NO 54 | 21 | gacgccacgggcgtgctcaa | SEQ ID NO 158 | GACGCCCACGGGCGUGCUCAA | UUGAGCACGCCCGUGGGCGUC |
| SEQ ID NO 55 | 21 | gctcggcaccaccatctccaa | SEQ ID NO 159 | GCUCGGCACCACCAUCUCCAA | UUGGAGAUGGUGGUGCCGAGC |
| SEQ ID NO 56 | 21 | ctcggcaccaccatctccaaa | SEQ ID NO 160 | CUCGGCACCACCAUCUCCAAA | UUUGGAGAUGGUGGUGCCGAG |
| SEQ ID NO 57 | 21 | ctcgctgccgccttcctcaa | SEQ ID NO 161 | CUCGCUGCCCGCCUUCCUCAA | UUGAGGAAGGCGGGCAGCGAG |
| SEQ ID NO 58 | 21 | cttcgccacctacctgctcaa | SEQ ID NO 162 | CUUCGCCACCUACCUGCUCAA | UUGAGCAGGUAGGUGGCGAAG |
| SEQ ID NO 59 | 21 | ggtgcccgaggaggcagccaa | SEQ ID NO 163 | GGUGCCCGAGGAGGCAGCCAA | UUGGCUGCCUCCUCGGGCACC |
| SEQ ID NO 60 | 21 | gctgctgctcacggccgtgaa | SEQ ID NO 164 | GCUGCUGCUCACGGCCGUGAA | UUCACGGCCGUGAGCAGCAGC |
| SEQ ID NO 61 | 21 | cgtgaactgctacagcgtgaa | SEQ ID NO 165 | CGUGAACUGCUACAGCGUGAA | UUCACGCUGUAGCAGUUCACG |
| SEQ ID NO 62 | 21 | ggatgcctttgccgccgccaa | SEQ ID NO 166 | GGAUGCCUUUGCCGCCGCCAA | UUGGCGGCGGCAAAGGCAUCC |
| SEQ ID NO 63 | 21 | gggcttcgtccagatcgggaa | SEQ ID NO 167 | GGGCUUCGUCCAGAUCGGGAA | UUCCCGAUCGGACGAAGCCC |
| SEQ ID NO 64 | 21 | cgggaagggtgatgtgtccaa | SEQ ID NO 168 | CGGGAAGGGUGAUGUGUCCAA | UUGGACACAUCACCCUUCCCG |
| SEQ ID NO | 21 | tgtgtccaatctagatccc | SEQ ID NO 169 | UGUGUCCAAUCUAGAU | UUGGGAUCUAGAUUGGAC |

Figure 26C

| | | | | | |
|---|---|---|---|---|---|
| 65 | | aa | | CCCAA | ACA |
| SEQ ID NO 66 | 21 | gatcccaacttctcatttgaa | SEQ ID NO 170 | GAUCCCAACUUCUCAUUUGAA | UUCAAAUGAGAAGUUGGGAUC |
| SEQ ID NO 67 | 21 | cttctcatttgaaggcaccaa | SEQ ID NO 171 | CUUCUCAUUUGAAGGCACCAA | UUGGUGCCUUCAAAUGAGAAG |
| SEQ ID NO 68 | 21 | ttctcatttgaaggcaccaa | SEQ ID NO 172 | UUCUCAUUUGAAGGCACCAAA | UUUGGUGCCUUCAAAUGAGAA |
| SEQ ID NO 69 | 21 | accaaactggatgtggggaa | SEQ ID NO 173 | ACCAAACUGGAUGUGGGGAA | UUCCCCACAUCCAGUUUGGU |
| SEQ ID NO 70 | 21 | ctttgcctatggaggatggaa | SEQ ID NO 174 | CUUUGCCUAUGGAGGAUGGAA | UUCCAUCCUCCAUAGGCAAAG |
| SEQ ID NO 71 | 21 | tggaggatggaattacttgaa | SEQ ID NO 175 | UGGAGGAUGGAAUUACUUGAA | UUCAAGUAAUUCCAUCCUCCA |
| SEQ ID NO 72 | 21 | tgaatttcgtcacagaggaaa | SEQ ID NO 176 | UGAAUUUCGUCACAGAGGAAA | UUUCCUCUGUGACGAAAUCA |
| SEQ ID NO 73 | 21 | cgtcacagaggaaatgatcaa | SEQ ID NO 177 | CGUCACAGAGGAAAUGAUCAA | UUGAUCAUUUCCUCUGUGACG |
| SEQ ID NO 74 | 21 | aaatgatcaaccccctacagaa | SEQ ID NO 178 | AAAUGAUCAACCCCUACAGAA | UUCUGUAGGGGUUGAUCAUUU |
| SEQ ID NO 75 | 21 | aatgatcaaccccctacagaaa | SEQ ID NO 179 | AAUGAUCAACCCCUACAGAAA | UUCUGUAGGGGUUGAUCAUUU |
| SEQ ID NO 76 | 21 | gctggtgtacgtgctgaccaa | SEQ ID NO 180 | GCUGGUGUACGUGCUGACCAA | UUGGUCAGCACGUACACCAGC |
| SEQ ID NO 77 | 21 | cgtggccgtggacttcgggaa | SEQ ID NO 181 | CGUGGCCGUGGACUUCGGGAA | UUCCCGAAGUCCACGGCCACG |
| SEQ ID NO 78 | 21 | gtcctgcttcggctccgtcaa | SEQ ID NO 182 | GUCCUGCUUCGGCUCCGUCAA | UUGACGGAGCCGAAGCAGGAC |
| SEQ ID NO 79 | 21 | ttcttcgtggggtcccgggaa | SEQ ID NO 183 | UUCUUCGUGGGGUCCCGGGAA | UUCCCGGGACCCCACGAAGAA |
| SEQ ID NO 80 | 21 | gctgctctacgccttctccaa | SEQ ID NO 184 | GCUGCUCUACGCCUUCUCCAA | UUGGAGAAGGCGUAGAGCAGC |
| SEQ ID NO 81 | 21 | ggacatcttctccgtcatcaa | SEQ ID NO 185 | GGACAUCUUCUCCGUCAUCAA | UUGAUGACGGAGAAGAUGUCC |
| SEQ ID NO 82 | 21 | caacttcttcagcttcttcaa | SEQ ID NO 186 | CAACUUCUUCAGCUUCUUCAA | UUGAAGAAGCUGAAGAAGUUG |
| SEQ ID NO 83 | 21 | tgatctggctgcgccacagaa | SEQ ID NO 187 | UGAUCUGGCUGCGCCACAGAA | UUCUGUGGCGCAGCCAGAUCA |
| SEQ ID NO 84 | 21 | gatctggctgcgccacagaaa | SEQ ID NO 188 | GAUCUGGCUGCGCCACAGAAA | UUUCUGUGGCGCAGCCAGAUC |
| SEQ ID NO 85 | 21 | tgagcttgagcggcccatcaa | SEQ ID NO 189 | UGAGCUUGAGCGGCCCAUCAA | UUGAUGGGCCGCUCAAGCUCA |
| SEQ ID NO 86 | 21 | tgagcggcccatcaaggtgaa | SEQ ID NO 190 | UGAGCGGCCCAUCAAGGUGAA | UUCACCUUGAUGGGCCGCUCA |
| SEQ ID NO 87 | 21 | gatcgccgtctccttctggaa | SEQ ID NO 191 | GAUCGCCGUCUCCUUCUGGAA | UUCCAGAAGGAGACGGCGAUC |
| SEQ ID NO 88 | 21 | cttcttcggggtctggtggaa | SEQ ID NO 192 | CUUCUUCGGGGUCUGGUGGAA | UUCCACCAGACCCCGAAGAAG |
| SEQ ID NO 89 | 21 | ttcttcggggtctggtggaaa | SEQ ID NO 193 | UUCUUCGGGGUCUGGUGGAAA | UUUCCACCAGACCCCGAAGAA |
| SEQ ID NO 90 | 21 | tcttcggggtctggtggaaaa | SEQ ID NO 194 | UCUUCGGGGUCUGGUGGAAAA | UUUUCCACCAGACCCCGAAGA |
| SEQ ID NO 91 | 21 | cttcggggtctggtggaaaaa | SEQ ID NO 195 | CUUCGGGGUCUGGUGGAAAAA | UUUUUCCACCAGACCCCGAAG |
| SEQ ID NO 92 | 21 | cggggtctggtggaaaacaa | SEQ ID NO 196 | CGGGGUCUGGUGGAAAACAA | UUGUUUUCCACCAGACCCCG |
| SEQ ID NO 93 | 21 | ctggtggaaaacaagcccaa | SEQ ID NO 197 | CUGGUGGAAAACAAGCCCAA | UUGGGCUUGUUUUCCACCAG |
| SEQ ID NO 94 | 21 | cacgaccgtcctgtgtcagaa | SEQ ID NO 198 | CACGACCGUCCUGUGUCAGAA | UUCUGACACAGGACGGUCGUG |
| SEQ ID NO 95 | 19 | aagatgctggccgccaagagc | SEQ ID NO 199 | GAUGCUGGCCGCCAAGAGC | GCUCUUGGCGGCCAGCAUC |
| SEQ ID NO 96 | 19 | aacatcacgctgctcaacggc | SEQ ID NO 200 | CAUCACGCUGCUCAACGC | GCCGUUGAGCAGCGUGAUG |
| SEQ ID NO 97 | 19 | aagctctggatcgagctgtc | SEQ ID NO 201 | GCUCUGGAUCGAGCUGCUC | GAGCAGCUCGAUCCAGAGC |
| SEQ ID NO 98 | 19 | aactgctacagcgtgaaggcc | SEQ ID NO 202 | CUGCUACAGCGUGAAGGCC | GGCCUUCACGCUGUAGCAG |
| SEQ ID NO 99 | 19 | aacattgtgctggcattatac | SEQ ID NO 203 | CAUUGUGCUGGCAUUAUAC | GUAUAAUGCCAGCACAAUG |

Figure 26D

| SEQ ID NO 100 | 19 | aaggacatcttctccgtcatc | SEQ ID NO 204 | GGACAUCUUCUCCGUCAUC | GAUGACGGAGAAGAUGUCC |
|---|---|---|---|---|---|
| SEQ ID NO 101 | 19 | cttcgccacctacctgctcaa | SEQ ID NO 205 | UCGCCACCUACCUGCUCAA | UUGAGCAGGUAGGUGGCGA |
| SEQ ID NO 102 | 19 | ggacatcttctccgtcatcaa | SEQ ID NO 206 | ACAUCUUCUCCGUCAUCAA | UUGAUGACGGAGAAGAUGU |
| SEQ ID NO 103 | 19 | tgatctggctgcgccacagaa | SEQ ID NO 207 | AUCUGGCUGCGCCACAGAA | UUCUGUGGCGCAGCCAGAU |
| SEQ ID NO 104 | 19 | gatcgccgtctccttctggaa | SEQ ID NO 208 | UCGCCGUCUCCUUCUGGAA | UUCCAGAAGGAGACGGCGA |

Figure 27A

| SEQ ID NO | nucleotide | Sequences of interest | ASCT2 siRNA | | |
|---|---|---|---|---|---|
| | | human mRNA target sequence | | 5' sense | 5' anti-sense |
| SEQ ID NO 209 | 21 | aagagaggaatatcaccggaa | SEQ ID NO 298 | AAGAGAGGAAUAUCACCGGAA | UUCCGGUGAUAUUCCUCUCUU |
| SEQ ID NO 210 | 21 | aatatcaccggaaccagggtg | SEQ ID NO 299 | AAUAUCACCGGAACCAGGGUG | CACCCUGGUUCCGGUGAUAUU |
| SEQ ID NO 211 | 21 | aaccagggtgaaggtgcccgt | SEQ ID NO 300 | AACCAGGGUGAAGGUGCCCGU | ACGGGCACCUUCACCCUGGUU |
| SEQ ID NO 212 | 21 | aaggtgcccgtggggcaggag | SEQ ID NO 301 | AAGGUGCCCGUGGGGCAGGAG | CUCCUGCCCCACGGGCACCUU |
| SEQ ID NO 213 | 21 | aacatcctgggcttggtagtg | SEQ ID NO 302 | AACAUCCUGGGCUUGGUAGUG | CACUACCAAGCCCAGGAUGUU |
| SEQ ID NO 214 | 21 | aagctggggcctgaagggag | SEQ ID NO 303 | AAGCUGGGGCCUGAAGGGGAG | CUCCCCUUCAGGCCCCAGCUU |
| SEQ ID NO 215 | 21 | aaggggagctgcttatccgct | SEQ ID NO 304 | AAGGGGAGCUGCUUAUCCGCU | AGCGGAUAAGCAGCUCCCCUU |
| SEQ ID NO 216 | 21 | aactccttcaatgaggccacc | SEQ ID NO 305 | AACUCCUUCAAUGAGGCCACC | GGUGGCCUCAUUGAAGGAGUU |
| SEQ ID NO 217 | 21 | aatgaggccaccatggttctg | SEQ ID NO 306 | AAUGAGGCCACCAUGGUUCUG | CAGAACCAUGGUGGCCUCAUU |
| SEQ ID NO 218 | 21 | aagatcgtggagatggaggat | SEQ ID NO 307 | AAGAUCGUGGAGAUGGAGGAU | AUCCUCCAUCUCCACGAUCUU |
| SEQ ID NO 219 | 21 | aagtacattctgtgctgcctg | SEQ ID NO 308 | AAGUACAUUCUGUGCUGCCUG | CAGGCAGCACAGAAUGUACUU |
| SEQ ID NO 220 | 21 | aaaaaccccaccgcttcctg | SEQ ID NO 309 | AAAAACCCCUACCGCUUCCUG | CAGGAAGCGGUAGGGGUUUUU |
| SEQ ID NO 221 | 21 | aaaaccccaccgcttcctgt | SEQ ID NO 310 | AAAACCCCUACCGCUUCCUGU | ACAGGAAGCGGUAGGGGUUUU |
| SEQ ID NO 222 | 21 | aaaccccaccgcttcctgtg | SEQ ID NO 311 | AAACCCCUACCGCUUCCUGUG | CACAGGAAGCGGUAGGGGUUU |
| SEQ ID NO 223 | 21 | aaccccaccgcttcctgtgg | SEQ ID NO 312 | AACCCCUACCGCUUCCUGUGG | CCACAGGAAGCGGUAGGGGUU |
| SEQ ID NO 224 | 21 | aagtgcgtggaggagaataat | SEQ ID NO 313 | AAGUGCGUGGAGGAGAAUAAU | AUUAUUCUCCUCCACGCACUU |
| SEQ ID NO 225 | 21 | aataatggcgtggccaagcac | SEQ ID NO 314 | AAUAAUGGCGUGGCCAAGCAC | GUGCUUGGCCACGCCAUUAUU |
| SEQ ID NO 226 | 21 | aatggcgtggccaagcacatc | SEQ ID NO 315 | AAUGGCGUGGCCAAGCACAUC | GAUGUGCUUGGCCACGCCAUU |
| SEQ ID NO 227 | 21 | aagcacatcagccgtttcatc | SEQ ID NO 316 | AAGCACAUCAGCCGUUUCAUC | GAUGAAACGGCUGAUGUGCUU |
| SEQ ID NO 228 | 21 | aacatggacggtgccgcgctc | SEQ ID NO 317 | AACAUGGACGGUGCCGCGCUC | GAGCGCGGCACCGUCCAUGUU |
| SEQ ID NO 229 | 21 | aaagatcatcaccatcctggt | SEQ ID NO 318 | AAAGAUCAUCACCAUCCUGGU | ACCAGGAUGGUGAUGAUCUUU |
| SEQ ID NO 230 | 21 | aagatcatcaccatcctggtc | SEQ ID NO 319 | AAGAUCAUCACCAUCCUGGUC | GACCAGGAUGGUGAUGAUCUU |
| SEQ ID NO 231 | 21 | aagcagtcaacctccggtcg | SEQ ID NO 320 | AAGCAGUCAACCUCCGGUCG | CGACCGGAGGUUGACUGCUUU |
| SEQ ID NO 232 | 21 | aacctccggtcgaccatatc | SEQ ID NO 321 | AACCUCCGGUCGACCAUAUC | GAUAUGGUCGACCGGAGGUU |
| SEQ ID NO 233 | 21 | aatgtagaaggtgacgctctg | SEQ ID NO 322 | AAUGUAGAAGGUGACGCUCUG | CAGAGCGUCACCUUCUACAUU |
| SEQ ID NO 234 | 21 | aaggtgacgctctgggggcag | SEQ ID NO 323 | AAGGUGACGCUCUGGGGCAG | CUGCCCCAGAGCGUCACCUU |
| SEQ ID NO 235 | 21 | aaaaattacgtggaccgtacg | SEQ ID NO 324 | AAAAAUUACGUGGACCGUACGG | CCGUACGGUCCACGUAAUUUU |
| SEQ ID NO 236 | 21 | aaattacgtggaccgtacgga | SEQ ID NO 325 | AAAUUACGUGGACCGUACGGA | UCCGUACGGUCCACGUAAUUU |
| SEQ ID NO 237 | 21 | aattacgtggaccgtacggag | SEQ ID NO 326 | AAUUACGUGGACCGUACGGAG | CUCCGUACGGUCCACGUAAUU |
| SEQ ID NO 238 | 21 | aagcacagagcctgagttgat | SEQ ID NO 327 | AAGCACAGAGCCUGAGUUGAU | AUCAACUCAGGCUCUGUGCUU |
| SEQ ID NO 239 | 21 | aagtgaagagtgagctgccc | SEQ ID NO 328 | AAGUGAAGAGUGAGCUGCCCC | GGGGCAGCUCACUCUUCACUU |

Figure 27B

| | | | | | |
|---|---|---|---|---|---|
| SEQ ID NO 240 | 21 | aagagtgagctgcccctggat | SEQ ID NO 329 | AAGAGUGAGCUGCCCCUGGAU | AUCCAGGGGCAGCUCACUCUU |
| SEQ ID NO 241 | 21 | aaggaaacccctcctcaaac | SEQ ID NO 330 | AAGGAAACCCCUCCUCAAAC | GUUUGAGGAGGGGUUUCCUU |
| SEQ ID NO 242 | 21 | aaacccctcctcaaacacta | SEQ ID NO 331 | AAACCCCUCCUCAAACACUA | UAGUGUUUGAGGAGGGGUUU |
| SEQ ID NO 243 | 21 | aaacactatcggggccccgc | SEQ ID NO 332 | AAACACUAUCGGGGGCCCGCA | UGCGGGCCCCGAUAGUGUUU |
| SEQ ID NO 244 | 21 | aacactatcggggcccgcag | SEQ ID NO 333 | AACACUAUCGGGGGCCCGCAG | CUGCGGGCCCCGAUAGUGUU |
| SEQ ID NO 245 | 21 | aagagaggaatataccggaa | SEQ ID NO 334 | AAGAGAGGAAUAUCACCGGAA | UUCCGGUGAUAUUCCUCUCUU |
| SEQ ID NO 246 | 21 | tatcaccggaaccagggtga | SEQ ID NO 335 | UAUCACCGGAACCAGGGUGAA | UUCACCCUGGUUCCGGUGAUA |
| SEQ ID NO 247 | 21 | gcaggaggtggaggggatgaa | SEQ ID NO 336 | GCAGGAGGUGGAGGGGAUGAA | UUCAUCCCCUCCACCUCCUGC |
| SEQ ID NO 248 | 21 | ctttggtgtggcgctgcggaa | SEQ ID NO 337 | CUUUGGUGUGGCGCUGCGGAA | UUCCGCAGCGCCACACCAAAG |
| SEQ ID NO 249 | 21 | ctgcggaagctggggcctga | SEQ ID NO 338 | CUGCGGAAGCUGGGGCCUGAA | UUCAGGCCCCAGCUUCCGCAG |
| SEQ ID NO 250 | 21 | gctgcttatccgcttcttcaa | SEQ ID NO 339 | GCUGCUUAUCCGCUUCUUCAA | UUGAAGAAGCGGAUAAGCAGC |
| SEQ ID NO 251 | 21 | ccgcttcttcaactccttcaa | SEQ ID NO 340 | CCGCUUCUUCAACUCCUUCAA | UUGAAGGAGUUGAAGAAGCGG |
| SEQ ID NO 252 | 21 | catgttcctggtggctggcaa | SEQ ID NO 341 | CAUGUUCCUGGUGGCUGGCAA | UUGCCAGCCACCAGGAACAUG |
| SEQ ID NO 253 | 21 | actctttgcccgccttggcaa | SEQ ID NO 342 | ACUCUUUGCCCGCCUUGGCAA | UUGCCAAGGCGGGCAAAGAGU |
| SEQ ID NO 254 | 21 | ctacttcctcttcacccgcaa | SEQ ID NO 343 | CUACUUCCUCUUCACCCGCAA | UUGCGGGUGAAGAGGAAGUAG |
| SEQ ID NO 255 | 21 | tacttcctcttcacccgcaaa | SEQ ID NO 344 | UACUUCCUCUUCACCCGCAAA | UUUGCGGGUGAAGAGGAAGUA |
| SEQ ID NO 256 | 21 | cttcctcttcacccgcaaaaa | SEQ ID NO 345 | CUUCCUCUUCACCCGCAAAAA | UUUUUGCGGGUGAAGAGGAAG |
| SEQ ID NO 257 | 21 | cacgctgccgctgatgatgaa | SEQ ID NO 346 | CACGCUGCCGCUGAUGAUGAA | UUCAUCAUCAGCGGCAGCGUG |
| SEQ ID NO 258 | 21 | gatgaagtgcgtggaggagaa | SEQ ID NO 347 | GAUGAAGUGCGUGGAGGAGAA | UUCUCCUCCACGCACUUCAUC |
| SEQ ID NO 259 | 21 | gaagtgcgtggaggagaataa | SEQ ID NO 348 | GAAGUGCGUGGAGGAGAAUAA | UUAUUCUCCUCCACGCACUUC |
| SEQ ID NO 260 | 21 | ggagaataatggcgtggccaa | SEQ ID NO 349 | GGAGAAUAAUGGCGUGGCCAA | UUGGCCACGCCAUUAUUCUCC |
| SEQ ID NO 261 | 21 | gcccatcggcgccaccgtcaa | SEQ ID NO 350 | GCCCAUCGGCGCCACCGUCAA | UUGACGGUGGCGCCGAUGGGC |
| SEQ ID NO 262 | 21 | gcagtccttggacttcgtaaa | SEQ ID NO 351 | GCAGUCCUUGGACUUCGUAAA | UUUACGAAGUCCAAGGACUGC |
| SEQ ID NO 263 | 21 | agcagtccttggacttcgtaa | SEQ ID NO 352 | AGCAGUCCUUGGACUUCGUAA | UUACGAAGUCCAAGGACUGCU |
| SEQ ID NO 264 | 21 | catcatcctcgaagcagtcaa | SEQ ID NO 353 | CAUCAUCCUCGAAGCAGUCAA | UUGACUGCUUCGAGGAUGAUG |
| SEQ ID NO 265 | 21 | actctggccatcatcctcgaa | SEQ ID NO 354 | ACUCUGGCCAUCAUCCUCGAA | UUCGAGGAUGAUGGCCAGAGU |
| SEQ ID NO 266 | 21 | tgtaccgtcctcaatgtagaa | SEQ ID NO 355 | UGUACCGUCCUCAAUGUAGAA | UUCUACAUUGAGGACGGUACA |
| SEQ ID NO 267 | 21 | ccggtcctgtaccgtcctcaa | SEQ ID NO 356 | CCGGUCCUGUACCGUCCUCAA | UUGAGGACGGUACAGGACCGG |
| SEQ ID NO 268 | 21 | gggggcaggactcctccaaa | SEQ ID NO 357 | GGGGGCAGGACUCCUCCAAAA | UUUUGGAGGAGUCCUGCCCCC |
| SEQ ID NO 269 | 21 | tgggggcaggactcctccaa | SEQ ID NO 358 | UGGGGGCAGGACUCCUCCAAA | UUUGGAGGAGUCCUGCCCCCA |
| SEQ ID NO 270 | 21 | ctgggggcaggactcctcca | SEQ ID NO 359 | CUGGGGGCAGGACUCCUCCAA | UUGGAGGAGUCCUGCCCCCAG |
| SEQ ID NO 271 | 21 | tggaccgtacggagtcgaga | SEQ ID NO 360 | UGGACCGUACGGAGUCGAGAA | UUCUCGACUCCGUACGGUCCA |
| SEQ ID NO 272 | 21 | acagagcctgagttgataca | SEQ ID NO 361 | ACAGAGCCUGAGUUGAUACAA | UUGUAUCAACUCAGGCUCUGU |
| SEQ ID NO 273 | 21 | gcctgagttgatacaagtga | SEQ ID NO 362 | GCCUGAGUUGAUACAAGUGAA | UUCACUUGUAUCAACUCAGGC |
| SEQ ID NO | 21 | ctgccagtccccactgagga | SEQ ID NO 363 | CUGCCAGUCCCCACUGAGGA | UUCCUCAGUGGGGAC |

Figure 27C

| | | | | AGGAA | UGGCAG |
|---|---|---|---|---|---|
| 274 | | a | | | |
| SEQ ID NO 275 | 21 | cagtccccactgaggaagga a | SEQ ID NO 364 | CUGUCCCACUGAGGA AGGAA | UUCCUUCCUCAGUGG GGACUG |
| SEQ ID NO 276 | 21 | ggaaggaaaccccctcctca a | SEQ ID NO 365 | GGAAGGAAACCCCCUC CUCAA | UUGAGGAGGGGGUUU CCUUCC |
| SEQ ID NO 277 | 21 | gaaggaaaccccctcctcaa a | SEQ ID NO 366 | GAAGGAAACCCCCUCC UCAAA | UUUGAGGAGGGGGUU UCCUUC |
| SEQ ID NO 278 | 21 | tgccacggtcgcctctgaga a | SEQ ID NO 367 | UGCCACGGUCGCCUCU GAGAA | UUCUCAGAGGCGACC GUGGCA |
| SEQ ID NO 279 | 21 | acggtcgcctctgagaagga a | SEQ ID NO 368 | ACGGUCGCCUCUGAG AAGGAA | UUCCUUCUCAGAGGC GACCGU |
| SEQ ID NO 280 | 21 | gagaaggaatcagtcatgta a | SEQ ID NO 369 | GAGAAGGAAUCAGUC AUGUAA | UUACAUGACUGAUUC CUUCUC |
| SEQ ID NO 281 | 19 | gagaggaatatcaccggaa | SEQ ID NO 370 | GAGAGGAAUAUCACC GGAA | UUCCGGUGAUAUUCC UCUC |
| SEQ ID NO 282 | 19 | gctggggcctgaagggag | SEQ ID NO 371 | CUCCUUCAAUGAGGCC ACC | GGUGGCCUCAUUGAA GGAG |
| SEQ ID NO 283 | 19 | taatggcgtggccaagcac | SEQ ID NO 372 | UAAUGGCGUGGCCAA GCAC | GUGCUUGGCCACGCCA UUA |
| SEQ ID NO 284 | 19 | tggcgtggccaagcacatc | SEQ ID NO 373 | UGGCGUGGCCAAGCA CAUC | GAUGUGCUUGGCCAC GCCA |
| SEQ ID NO 285 | 19 | catggacggtgccgcgctc | SEQ ID NO 374 | CAUGGACGGUGCCGC GCUC | GAGCGCGGCACCGUCC AUG |
| SEQ ID NO 286 | 19 | aattacgtggaccgtacgg | SEQ ID NO 375 | AAUUACGUGGACCGU ACGG | CCGUACGGUCCACGUA AUU |
| SEQ ID NO 287 | 19 | attacgtggaccgtacgga | SEQ ID NO 376 | AUUACGUGGACCGUA CGGA | UCCGUACGGUCCACGU AAU |
| SEQ ID NO 288 | 19 | ttacgtggaccgtacggag | SEQ ID NO 377 | UUACGUGGACCGUAC GGAG | CUCCGUACGGUCCACG UAA |
| SEQ ID NO 289 | 19 | gcacagagcctgagttgat | SEQ ID NO 378 | GCACAGAGCCUGAGU UGAU | AUCAACUCAGGCUCUG UGC |
| SEQ ID NO 290 | 19 | gagaggaatatcaccggaa | SEQ ID NO 379 | GAGAGGAAUAUCACC GGAA | UUCCGGUGAUAUUCC UCUC |
| SEQ ID NO 291 | 19 | agaataatggcgtggccaa | SEQ ID NO 380 | AGAAUAAUGGCGUGG CCAA | UUGGCCACGCCAUUA UUCU |
| SEQ ID NO 292 | 19 | tcatcctcgaagcagtcaa | SEQ ID NO 381 | UCAUCCUCGAAGCAGU CAA | UUGACUGCUUCGAGG AUGA |
| SEQ ID NO 293 | 19 | ggtcctgtaccgtcctcaa | SEQ ID NO 382 | GGUCCUGUACCGUCC UCAA | UUGAGGACGGUACAG GACC |
| SEQ ID NO 294 | 19 | gaccgtacggagtcgagaa | SEQ ID NO 383 | GACCGUACGGAGUCG AGAA | UUCUCGACUCCGUACG GUC |
| SEQ ID NO 295 | 19 | agagcctgagttgatacaa | SEQ ID NO 384 | AGAGCCUGAGUUGAU ACAA | UUGUAUCAACUCAGG CUCU |
| SEQ ID NO 296 | 19 | ccacggtcgcctctgagaa | SEQ ID NO 385 | CCACGGUCGCCUCUGA GAA | UUCUCAGAGGCGACC GUGG |
| SEQ ID NO 297 | 19 | ggtcgcctctgagaaggaa | SEQ ID NO 386 | GGUCGCCUCUGAGAA GGAA | UUCCUUCUCAGAGGC GACC |

SEQUENCE LISTING

```
<160> NUMBER OF SEQ ID NOS: 605

<210> SEQ ID NO 1
<211> LENGTH: 21
<212> TYPE: DNA
<213> ORGANISM: Homo sapiens

<400> SEQUENCE: 1
aagcggcgcg cgctagcggc g                                               21

<210> SEQ ID NO 2
<211> LENGTH: 21
<212> TYPE: DNA
<213> ORGANISM: Homo sapiens

<400> SEQUENCE: 2
aaggaagagg cgcgggagaa g                                               21

<210> SEQ ID NO 3
<211> LENGTH: 21
<212> TYPE: DNA
<213> ORGANISM: Homo sapiens

<400> SEQUENCE: 3
aagaggcgcg ggagaagatg c                                               21

<210> SEQ ID NO 4
<211> LENGTH: 21
<212> TYPE: DNA
<213> ORGANISM: Homo sapiens

<400> SEQUENCE: 4
aagatgctgg ccgccaagag c                                               21
```

```
<210> SEQ ID NO 5
<211> LENGTH: 21
<212> TYPE: DNA
<213> ORGANISM: Homo sapiens

<400> SEQUENCE: 5
aagagcgcgg acggctcggc g                                              21

<210> SEQ ID NO 6
<211> LENGTH: 21
<212> TYPE: DNA
<213> ORGANISM: Homo sapiens

<400> SEQUENCE: 6
aacatcacgc tgctcaacgg c                                              21

<210> SEQ ID NO 7
<211> LENGTH: 21
<212> TYPE: DNA
<213> ORGANISM: Homo sapiens

<400> SEQUENCE: 7
aaggaggcag gctcgccggg g                                              21

<210> SEQ ID NO 8
<211> LENGTH: 21
<212> TYPE: DNA
<213> ORGANISM: Homo sapiens

<400> SEQUENCE: 8
aaatcgggcg gcgactacgc c                                              21

<210> SEQ ID NO 9
<211> LENGTH: 21
<212> TYPE: DNA
<213> ORGANISM: Homo sapiens

<400> SEQUENCE: 9
aatcgggcgg cgactacgcc t                                              21

<210> SEQ ID NO 10
<211> LENGTH: 21
<212> TYPE: DNA
<213> ORGANISM: Homo sapiens

<400> SEQUENCE: 10
aagctctgga tcgagctgct c                                              21

<210> SEQ ID NO 11
<211> LENGTH: 21
<212> TYPE: DNA
<213> ORGANISM: Homo sapiens

<400> SEQUENCE: 11
aagccgctct tccccacctg c                                              21

<210> SEQ ID NO 12
<211> LENGTH: 21
<212> TYPE: DNA
<213> ORGANISM: Homo sapiens

<400> SEQUENCE: 12
aagctcgtgg cctgcctctg c                                              21
```

```
<210> SEQ ID NO 13
<211> LENGTH: 21
<212> TYPE: DNA
<213> ORGANISM: Homo sapiens

<400> SEQUENCE: 13
aactgctaca gcgtgaaggc c                                              21

<210> SEQ ID NO 14
<211> LENGTH: 21
<212> TYPE: DNA
<213> ORGANISM: Homo sapiens

<400> SEQUENCE: 14
aaggccgcca cccgggtcca g                                              21

<210> SEQ ID NO 15
<211> LENGTH: 21
<212> TYPE: DNA
<213> ORGANISM: Homo sapiens

<400> SEQUENCE: 15
aagctcctgg ccctggccct g                                              21

<210> SEQ ID NO 16
<211> LENGTH: 21
<212> TYPE: DNA
<213> ORGANISM: Homo sapiens

<400> SEQUENCE: 16
aagggtgatg tgtccaatct a                                              21

<210> SEQ ID NO 17
<211> LENGTH: 21
<212> TYPE: DNA
<213> ORGANISM: Homo sapiens

<400> SEQUENCE: 17
aatctagatc ccaacttctc a                                              21

<210> SEQ ID NO 18
<211> LENGTH: 21
<212> TYPE: DNA
<213> ORGANISM: Homo sapiens

<400> SEQUENCE: 18
aacttctcat ttgaaggcac c                                              21

<210> SEQ ID NO 19
<211> LENGTH: 21
<212> TYPE: DNA
<213> ORGANISM: Homo sapiens

<400> SEQUENCE: 19
aaggcaccaa actggatgtg g                                              21

<210> SEQ ID NO 20
<211> LENGTH: 21
<212> TYPE: DNA
<213> ORGANISM: Homo sapiens

<400> SEQUENCE: 20
```

```
aaactggatg tggggaacat t                                         21

<210> SEQ ID NO 21
<211> LENGTH: 21
<212> TYPE: DNA
<213> ORGANISM: Homo sapiens

<400> SEQUENCE: 21
aactggatgt ggggaacatt g                                         21

<210> SEQ ID NO 22
<211> LENGTH: 21
<212> TYPE: DNA
<213> ORGANISM: Homo sapiens

<400> SEQUENCE: 22
aacattgtgc tggcattata c                                         21

<210> SEQ ID NO 23
<211> LENGTH: 21
<212> TYPE: DNA
<213> ORGANISM: Homo sapiens

<400> SEQUENCE: 23
aattacttga atttcgtcac a                                         21

<210> SEQ ID NO 24
<211> LENGTH: 21
<212> TYPE: DNA
<213> ORGANISM: Homo sapiens

<400> SEQUENCE: 24
aatttcgtca cagaggaaat g                                         21

<210> SEQ ID NO 25
<211> LENGTH: 21
<212> TYPE: DNA
<213> ORGANISM: Homo sapiens

<400> SEQUENCE: 25
aaatgatcaa cccctacaga a                                         21

<210> SEQ ID NO 26
<211> LENGTH: 21
<212> TYPE: DNA
<213> ORGANISM: Homo sapiens

<400> SEQUENCE: 26
aatgatcaac ccctacagaa a                                         21

<210> SEQ ID NO 27
<211> LENGTH: 21
<212> TYPE: DNA
<213> ORGANISM: Homo sapiens

<400> SEQUENCE: 27
aacccctaca gaaacctgcc c                                         21

<210> SEQ ID NO 28
<211> LENGTH: 21
<212> TYPE: DNA
<213> ORGANISM: Homo sapiens

<400> SEQUENCE: 28
```
aaacctgccc ctggccatca t                                              21

<210> SEQ ID NO 29
<211> LENGTH: 21
<212> TYPE: DNA
<213> ORGANISM: Homo sapiens

<400> SEQUENCE: 29
aacctgcccc tggccatcat c                                              21

<210> SEQ ID NO 30
<211> LENGTH: 21
<212> TYPE: DNA
<213> ORGANISM: Homo sapiens

<400> SEQUENCE: 30
aacctggcct acttcaccac c                                              21

<210> SEQ ID NO 31
<211> LENGTH: 21
<212> TYPE: DNA
<213> ORGANISM: Homo sapiens

<400> SEQUENCE: 31
aactatcacc tgggcgtcat g                                              21

<210> SEQ ID NO 32
<211> LENGTH: 21
<212> TYPE: DNA
<213> ORGANISM: Homo sapiens

<400> SEQUENCE: 32
aatgggtccc tgttcacatc c                                              21

<210> SEQ ID NO 33
<211> LENGTH: 21
<212> TYPE: DNA
<213> ORGANISM: Homo sapiens

<400> SEQUENCE: 33
aaggccacct gccctccatc c                                              21

<210> SEQ ID NO 34
<211> LENGTH: 21
<212> TYPE: DNA
<213> ORGANISM: Homo sapiens

<400> SEQUENCE: 34
aaggacatct tctccgtcat c                                              21

<210> SEQ ID NO 35
<211> LENGTH: 21
<212> TYPE: DNA
<213> ORGANISM: Homo sapiens

<400> SEQUENCE: 35
aacttcttca gcttcttcaa c                                              21

<210> SEQ ID NO 36
<211> LENGTH: 21
<212> TYPE: DNA
<213> ORGANISM: Homo sapiens

```
<400> SEQUENCE: 36
aactggctct gcgtggccct g                                              21

<210> SEQ ID NO 37
<211> LENGTH: 21
<212> TYPE: DNA
<213> ORGANISM: Homo sapiens

<400> SEQUENCE: 37
aaagcctgag cttgagcggc c                                              21

<210> SEQ ID NO 38
<211> LENGTH: 21
<212> TYPE: DNA
<213> ORGANISM: Homo sapiens

<400> SEQUENCE: 38
aagcctgagc ttgagcggcc c                                              21

<210> SEQ ID NO 39
<211> LENGTH: 21
<212> TYPE: DNA
<213> ORGANISM: Homo sapiens

<400> SEQUENCE: 39
aaggtgaacc tggccctgcc t                                              21

<210> SEQ ID NO 40
<211> LENGTH: 21
<212> TYPE: DNA
<213> ORGANISM: Homo sapiens

<400> SEQUENCE: 40
aacctggccc tgcctgtgtt c                                              21

<210> SEQ ID NO 41
<211> LENGTH: 21
<212> TYPE: DNA
<213> ORGANISM: Homo sapiens

<400> SEQUENCE: 41 aagcacccg tggagtgtgg c                                               21

<210> SEQ ID NO 42
<211> LENGTH: 21
<212> TYPE: DNA
<213> ORGANISM: Homo sapiens

<400> SEQUENCE: 42
aaaaacaagc ccaagtggct c                                              21

<210> SEQ ID NO 43
<211> LENGTH: 21
<212> TYPE: DNA
<213> ORGANISM: Homo sapiens

<400> SEQUENCE: 43
aaacaagccc aagtggctcc t                                              21

<210> SEQ ID NO 44
<211> LENGTH: 21
<212> TYPE: DNA
<213> ORGANISM: Homo sapiens
```

```
<400> SEQUENCE: 44
aacaagccca agtggctcct c                                            21

<210> SEQ ID NO 45
<211> LENGTH: 21
<212> TYPE: DNA
<213> ORGANISM: Homo sapiens

<400> SEQUENCE: 45
aagcccaagt ggctcctcca g                                            21

<210> SEQ ID NO 46
<211> LENGTH: 21
<212> TYPE: DNA
<213> ORGANISM: Homo sapiens

<400> SEQUENCE: 46
aagtggctcc tccagggcat c                                            21

<210> SEQ ID NO 47
<211> LENGTH: 21
<212> TYPE: DNA
<213> ORGANISM: Homo sapiens

<400> SEQUENCE: 47
aagctcatgc aggtggtccc c                                            21

<210> SEQ ID NO 48
<211> LENGTH: 21
<212> TYPE: DNA
<213> ORGANISM: Homo sapiens

<400> SEQUENCE: 48
ggcgccggcg gccgaggaga a                                            21

<210> SEQ ID NO 49
<211> LENGTH: 21
<212> TYPE: DNA
<213> ORGANISM: Homo sapiens

<400> SEQUENCE: 49
ccggcggccg aggagaagga a                                            21

<210> SEQ ID NO 50
<211> LENGTH: 21
<212> TYPE: DNA
<213> ORGANISM: Homo sapiens

<400> SEQUENCE: 50
ggagaagatg ctggccgcca a                                            21

<210> SEQ ID NO 51
<211> LENGTH: 21
<212> TYPE: DNA
<213> ORGANISM: Homo sapiens

<400> SEQUENCE: 51
gaaggaagag gcgcgggaga a                                            21

<210> SEQ ID NO 52
<211> LENGTH: 21
<212> TYPE: DNA
```

```
<213> ORGANISM: Homo sapiens

<400> SEQUENCE: 52
ggagaagatg ctggccgcca a                                              21

<210> SEQ ID NO 53
<211> LENGTH: 21
<212> TYPE: DNA
<213> ORGANISM: Homo sapiens

<400> SEQUENCE: 53
gggcgtgacc ctgcagcgga a                                              21

<210> SEQ ID NO 54
<211> LENGTH: 21
<212> TYPE: DNA
<213> ORGANISM: Homo sapiens

<400> SEQUENCE: 54
gacgcccacg ggcgtgctca a                                              21

<210> SEQ ID NO 55
<211> LENGTH: 21
<212> TYPE: DNA
<213> ORGANISM: Homo sapiens

<400> SEQUENCE: 55
gctcggcacc accatctcca a                                              21

<210> SEQ ID NO 56
<211> LENGTH: 21
<212> TYPE: DNA
<213> ORGANISM: Homo sapiens

<400> SEQUENCE: 56
ctcggcacca ccatctccaa a                                              21

<210> SEQ ID NO 57
<211> LENGTH: 21
<212> TYPE: DNA
<213> ORGANISM: Homo sapiens

<400> SEQUENCE: 57
ctcgctgccc gccttcctca a                                              21

<210> SEQ ID NO 58
<211> LENGTH: 21
<212> TYPE: DNA
<213> ORGANISM: Homo sapiens

<400> SEQUENCE: 58
cttcgccacc tacctgctca a                                              21

<210> SEQ ID NO 59
<211> LENGTH: 21
<212> TYPE: DNA
<213> ORGANISM: Homo sapiens

<400> SEQUENCE: 59
ggtgcccgag gaggcagcca a                                              21

<210> SEQ ID NO 60
<211> LENGTH: 21
```

<212> TYPE: DNA
<213> ORGANISM: Homo sapiens

<400> SEQUENCE: 60
gctgctgctc acggccgtga a                                              21

<210> SEQ ID NO 61
<211> LENGTH: 21
<212> TYPE: DNA
<213> ORGANISM: Homo sapiens

<400> SEQUENCE: 61
cgtgaactgc tacagcgtga a                                              21

<210> SEQ ID NO 62
<211> LENGTH: 21
<212> TYPE: DNA
<213> ORGANISM: Homo sapiens

<400> SEQUENCE: 62
ggatgccttt gccgccgcca a                                              21

<210> SEQ ID NO 63
<211> LENGTH: 21
<212> TYPE: DNA
<213> ORGANISM: Homo sapiens

<400> SEQUENCE: 63
gggcttcgtc cagatcggga a                                              21

<210> SEQ ID NO 64
<211> LENGTH: 21
<212> TYPE: DNA
<213> ORGANISM: Homo sapiens

<400> SEQUENCE: 64
cgggaagggt gatgtgtcca a                                              21

<210> SEQ ID NO 65
<211> LENGTH: 21
<212> TYPE: DNA
<213> ORGANISM: Homo sapiens

<400> SEQUENCE: 65
tgtgtccaat ctagatccca a                                              21

<210> SEQ ID NO 66
<211> LENGTH: 21
<212> TYPE: DNA
<213> ORGANISM: Homo sapiens

<400> SEQUENCE: 66
gatcccaact tctcatttga a                                              21

<210> SEQ ID NO 67
<211> LENGTH: 21
<212> TYPE: DNA
<213> ORGANISM: Homo sapiens

<400> SEQUENCE: 67
cttctcattt gaaggcacca a                                              21

<210> SEQ ID NO 68

```
<211> LENGTH: 21
<212> TYPE: DNA
<213> ORGANISM: Homo sapiens

<400> SEQUENCE: 68
ttctcatttg aaggcaccaa a                                              21

<210> SEQ ID NO 69
<211> LENGTH: 20
<212> TYPE: DNA
<213> ORGANISM: Homo sapiens

<400> SEQUENCE: 69
accaaactgg atgtggggaa                                                20

<210> SEQ ID NO 70
<211> LENGTH: 21
<212> TYPE: DNA
<213> ORGANISM: Homo sapiens

<400> SEQUENCE: 70
ctttgcctat ggaggatgga a                                              21

<210> SEQ ID NO 71
<211> LENGTH: 21
<212> TYPE: DNA
<213> ORGANISM: Homo sapiens

<400> SEQUENCE: 71
tggaggatgg aattacttga a                                              21

<210> SEQ ID NO 72
<211> LENGTH: 21
<212> TYPE: DNA
<213> ORGANISM: Homo sapiens

<400> SEQUENCE: 72
tgaatttcgt cacagaggaa a                                              21

<210> SEQ ID NO 73
<211> LENGTH: 21
<212> TYPE: DNA
<213> ORGANISM: Homo sapiens

<400> SEQUENCE: 73
cgtcacagag gaaatgatca a                                              21

<210> SEQ ID NO 74
<211> LENGTH: 21
<212> TYPE: DNA
<213> ORGANISM: Homo sapiens

<400> SEQUENCE: 74
aaatgatcaa cccctacaga a                                              21

<210> SEQ ID NO 75
<211> LENGTH: 21
<212> TYPE: DNA
<213> ORGANISM: Homo sapiens

<400> SEQUENCE: 75
aatgatcaac ccctacagaa a                                              21
```

```
<210> SEQ ID NO 76
<211> LENGTH: 21
<212> TYPE: DNA
<213> ORGANISM: Homo sapiens

<400> SEQUENCE: 76
gctggtgtac gtgctgacca a                                              21

<210> SEQ ID NO 77
<211> LENGTH: 21
<212> TYPE: DNA
<213> ORGANISM: Homo sapiens

<400> SEQUENCE: 77
cgtggccgtg gacttcggga a                                              21

<210> SEQ ID NO 78
<211> LENGTH: 21
<212> TYPE: DNA
<213> ORGANISM: Homo sapiens

<400> SEQUENCE: 78
gtcctgcttc ggctccgtca a                                              21

<210> SEQ ID NO 79
<211> LENGTH: 21
<212> TYPE: DNA
<213> ORGANISM: Homo sapiens

<400> SEQUENCE: 79
ttcttcgtgg ggtcccggga a                                              21

<210> SEQ ID NO 80
<211> LENGTH: 21
<212> TYPE: DNA
<213> ORGANISM: Homo sapiens

<400> SEQUENCE: 80
gctgctctac gccttctcca a                                              21

<210> SEQ ID NO 81
<211> LENGTH: 21
<212> TYPE: DNA
<213> ORGANISM: Homo sapiens

<400> SEQUENCE: 81
ggacatcttc tccgtcatca a                                              21

<210> SEQ ID NO 82
<211> LENGTH: 21
<212> TYPE: DNA
<213> ORGANISM: Homo sapiens

<400> SEQUENCE: 82
caacttcttc agcttcttca a                                              21

<210> SEQ ID NO 83
<211> LENGTH: 21
<212> TYPE: DNA
<213> ORGANISM: Homo sapiens

<400> SEQUENCE: 83
tgatctggct gcgccacaga a                                              21
```

<210> SEQ ID NO 84
<211> LENGTH: 21
<212> TYPE: DNA
<213> ORGANISM: Homo sapiens

<400> SEQUENCE: 84
gatctggctg cgccacagaa a                                          21

<210> SEQ ID NO 85
<211> LENGTH: 21
<212> TYPE: DNA
<213> ORGANISM: Homo sapiens

<400> SEQUENCE: 85
tgagcttgag cggcccatca a                                          21

<210> SEQ ID NO 86
<211> LENGTH: 21
<212> TYPE: DNA
<213> ORGANISM: Homo sapiens

<400> SEQUENCE: 86
tgagcggccc atcaaggtga a                                          21

<210> SEQ ID NO 87
<211> LENGTH: 21
<212> TYPE: DNA
<213> ORGANISM: Homo sapiens

<400> SEQUENCE: 87
gatcgccgtc tccttctgga a                                          21

<210> SEQ ID NO 88
<211> LENGTH: 21
<212> TYPE: DNA
<213> ORGANISM: Homo sapiens

<400> SEQUENCE: 88
cttcttcggg gtctggtgga a                                          21

<210> SEQ ID NO 89
<211> LENGTH: 21
<212> TYPE: DNA
<213> ORGANISM: Homo sapiens

<400> SEQUENCE: 89
ttcttcgggg tctggtggaa a                                          21

<210> SEQ ID NO 90
<211> LENGTH: 21
<212> TYPE: DNA
<213> ORGANISM: Homo sapiens

<400> SEQUENCE: 90
tcttcggggt ctggtggaaa a                                          21

<210> SEQ ID NO 91
<211> LENGTH: 21
<212> TYPE: DNA
<213> ORGANISM: Homo sapiens

<400> SEQUENCE: 91
cttcggggtc tggtggaaaa a                                          21

<210> SEQ ID NO 92
<211> LENGTH: 21
<212> TYPE: DNA
<213> ORGANISM: Homo sapiens

<400> SEQUENCE: 92
cggggtctgg tggaaaaaca a                                              21

<210> SEQ ID NO 93
<211> LENGTH: 21
<212> TYPE: DNA
<213> ORGANISM: Homo sapiens

<400> SEQUENCE: 93
ctggtggaaa aacaagccca a                                              21

<210> SEQ ID NO 94
<211> LENGTH: 21
<212> TYPE: DNA
<213> ORGANISM: Homo sapiens

<400> SEQUENCE: 94
cacgaccgtc ctgtgtcaga a                                              21

<210> SEQ ID NO 95
<211> LENGTH: 21
<212> TYPE: DNA
<213> ORGANISM: Homo sapiens

<400> SEQUENCE: 95
aagatgctgg ccgccaagag c                                              21

<210> SEQ ID NO 96
<211> LENGTH: 21
<212> TYPE: DNA
<213> ORGANISM: Homo sapiens

<400> SEQUENCE: 96
aacatcacgc tgctcaacgg c                                              21

<210> SEQ ID NO 97
<211> LENGTH: 21
<212> TYPE: DNA
<213> ORGANISM: Homo sapiens

<400> SEQUENCE: 97
aagctctgga tcgagctgct c                                              21

<210> SEQ ID NO 98
<211> LENGTH: 21
<212> TYPE: DNA
<213> ORGANISM: Homo sapiens

<400> SEQUENCE: 98
aactgctaca gcgtgaaggc c                                              21

<210> SEQ ID NO 99
<211> LENGTH: 21
<212> TYPE: DNA
<213> ORGANISM: Homo sapiens

<400> SEQUENCE: 99
aacattgtgc tggcattata c                                              21

<210> SEQ ID NO 100
<211> LENGTH: 21
<212> TYPE: DNA
<213> ORGANISM: Homo sapiens

<400> SEQUENCE: 100
aaggacatct tctccgtcat c                                              21

<210> SEQ ID NO 101
<211> LENGTH: 21
<212> TYPE: DNA
<213> ORGANISM: Homo sapiens

<400> SEQUENCE: 101
cttcgccacc tacctgctca a                                              21

<210> SEQ ID NO 102
<211> LENGTH: 21
<212> TYPE: DNA
<213> ORGANISM: Homo sapiens

<400> SEQUENCE: 102
ggacatcttc tccgtcatca a                                              21

<210> SEQ ID NO 103
<211> LENGTH: 21
<212> TYPE: DNA
<213> ORGANISM: Homo sapiens

<400> SEQUENCE: 103
tgatctggct gcgccacaga a                                              21

<210> SEQ ID NO 104
<211> LENGTH: 21
<212> TYPE: DNA
<213> ORGANISM: Homo sapiens

<400> SEQUENCE: 104
gatcgccgtc tccttctgga a                                              21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 105
aagcggcgcg cgcuagcggc g                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 106
aaggaagagg cgcgggagaa g                                              21

```
<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 107
aagaggcgcg ggagaagaug c                                              21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 108
aagaugcugg ccgccaagag c                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 109
aagagcgcgg acggcucggc g                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 110
aacaucacgc ugcucaacgg c                                              21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 111
aaggaggcag gcucgccggg g                                              21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 112
aaaucgggcg gcgacuacgc c                                              21

<210> SEQ ID NO 113
```

```
<211> LENGTH: 21
<212> TYPE: RNA
<213> ORGANISM: Homo sapiens

<400> SEQUENCE: 113
aaucgggcgg cgacuacgcc u                                              21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 114
aagcucugga ucgagcugcu c                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 115
aagccgcucu uccccaccug c                                              21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 116
aagcucgugg ccugccucug c                                              21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 117
aacugcuaca gcgugaaggc c                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 118
aaggccgcca cccgggucca g                                              21

<210> SEQ ID NO 119
<211> LENGTH: 21
<212> TYPE: RNA
<213> ORGANISM: Artificial Sequence
<220> FEATURE:
```

-continued

<223> OTHER INFORMATION: Description of Artificial Sequence: Synthetic
     siRNA sense strand

<400> SEQUENCE: 119
aagcuccugg cccuggcccu g                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
     siRNA sense strand

<400> SEQUENCE: 120
aagggugaug uguccaaucu a                                              21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
     siRNA sense strand

<400> SEQUENCE: 121
aaucuagauc ccaacuucuc a                                              21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
     siRNA sense strand

<400> SEQUENCE: 122
aacuucucau uugaaggcac c                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
     siRNA sense strand

<400> SEQUENCE: 123
aaggcaccaa acuggaugug g                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
     siRNA sense strand

<400> SEQUENCE: 124
aaacuggaug ugggaacau u                                               21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic -continued siRNA sense strand

<400> SEQUENCE: 125
aacuggaugu ggggaacauu g                                             21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 126
aacauugugc uggcauuaua c                                             21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 127
aauuacuuga auuucgucac a                                             21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 128
aauuucguca cagaggaaau g                                             21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 129
aaaugaucaa ccccuacaga a                                             21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 130
aaugaucaac cccuacagaa a                                             21

<210> SEQ ID NO 131
<211> LENGTH: 21
<212> TYPE: RNA
<213> ORGANISM: Homo sapiens

<400> SEQUENCE: 131
aaccccuaca gaaaccugcc c                                                21

<210> SEQ ID NO 132
<211> LENGTH: 21
<212> TYPE: RNA
<213> ORGANISM: Homo sapiens

<400> SEQUENCE: 132
aaaccugccc cuggccauca u                                                21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 133
aaccugcccc uggccaucau c                                                21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 134
aaccuggccu acuucaccac c                                                21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 135
aacuaucacc ugggcgucau g                                                21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 136
aauggguccc uguucacauc c                                                21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 137
aaggccaccu gcccuccauc c                                                21

<210> SEQ ID NO 138

```
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 138
aaggacaucu ucuccgucau c                                           21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 139
aacuucuuca gcuucuucaa c                                           21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 140
aacuggcucu gcguggcccu g                                           21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 141
aaagccugag cuugagcggc c                                           21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 142
aagccugagc uugagcggcc c                                           21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 143
aaggugaacc uggcccugcc u                                           21

<210> SEQ ID NO 144
<211> LENGTH: 21
```

<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 144
aaccuggccc ugccuguguu c                                              21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 145
aagacacccg uggagugugg c                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 146
aaaaacaagc ccaaguggcu c                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 147
aaacaagccc aaguggcucc u                                              21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 148
aacaagccca aguggcuccu c                                              21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 149
aagcccaagu ggcuccucca g                                              21

<210> SEQ ID NO 150
<211> LENGTH: 21
<212> TYPE: RNA

```
<213> ORGANISM: Artificial Sequence
<220> FEATURE:
<223> OTHER INFORMATION: Description of Artificial Sequence: Synthetic
      siRNA sense strand

<400> SEQUENCE: 150
aaguggcucc uccagggcau c                                              21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 151
aagcucaugc aggugguccc c                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 152
ggcgccggcg gccgaggaga a                                              21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 153
ccggcggccg aggagaagga a                                              21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 154
ggagaagaug cuggccgcca a                                              21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 155
gaaggaagag gcgcgggaga a                                              21

<210> SEQ ID NO 156
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      siRNA sense strand

<400> SEQUENCE: 156
ggagaagaug cuggccgcca a                                              21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 157
gggcgugacc cugcagcgga a                                              21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 158
gacgcccacg ggcgugcuca a                                              21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 159
gcucggcacc accaucucca a                                              21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 160
cucggcacca ccaucuccaa a                                              21

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 161
cucgcugccc gccuuccuca a                                              21

<210> SEQ ID NO 162
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      siRNA sense strand

<400> SEQUENCE: 162
cuucgccacc uaccugcuca a                                              21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 163
ggugcccgag gaggcagcca a                                              21

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 164
gcugcugcuc acggccguga a                                              21

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 165
cgugaacugc uacagcguga a                                              21

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 166
ggaugccuuu gccgccgcca a                                              21

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 167
gggcuucguc cagaucggga a                                              21

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued siRNA sense strand

<400> SEQUENCE: 168
cgggaagggu gaugugucca a             21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 169
uguguccaau cuagauccca a             21

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 170
gaucccaacu ucucauuuga a             21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 171
cuucucauuu gaaggcacca a             21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 172
uucucauuug aaggcaccaa a             21

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 173
accaaacugg augugggaa             20

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand -continued

<400> SEQUENCE: 174
cuuugccuau ggaggaugga a                                          21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 175
uggaggaugg aauuacuuga a                                          21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 176
ugaauuucgu cacagaggaa a                                          21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 177
cgucacagag gaaaugauca a                                          21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 178
aaaugaucaa ccccuacaga a                                          21

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 179
aaugaucaac cccuacagaa a                                          21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

```
<400> SEQUENCE: 180
gcugguguac gugcugacca a                                              21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 181
cguggccgug gacuucggga a                                              21

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 182
guccugcuuc ggcuccguca a                                              21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 183
uucuucgugg ggucccggga a                                              21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 184
gcugcucuac gccuucucca a                                              21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 185
ggacaucuuc uccgucauca a                                              21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 186
```
caacuucuuc agcuucuuca a                                               21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 187
ugaucuggcu gcgccacaga a                                               21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 188
gaucuggcug cgccacagaa a                                               21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 189
ugagcuugag cggcccauca a                                               21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 190
ugagcggccc aucaagguga a                                               21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 191
gaucgccguc uccuucugga a                                               21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 192
cuucuucggg gucuggugga a         21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 193
uucuucgggg ucugguggaa a         21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 194
ucuucggggu cugguggaaa a         21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 195
cuucgggguc ugguggaaaa a         21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 196
cggggucugg uggaaaaaca a         21

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 197
cugguggaaa aacaagccca a         21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 198
cacgaccguc cugugucaga a         21

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 199
gaugcuggcc gccaagagc                                              19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 200
caucacgcug cucaacggc                                              19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 201
gcucuggauc gagcugcuc                                              19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 202
cugcuacagc gugaaggcc                                              19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 203
cauugugcug gcauuauac                                              19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 204
ggacaucuuc uccgucauc                                              19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 205
ucgccaccua ccugcucaa                                                19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 206
acaucuucuc cgucaucaa                                                19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 207
aucuggcugc gccacagaa                                                19

<210> SEQ ID NO 208
<211> LENGTH: 19
<212> TYPE: RNA
<213> ORGANISM: Homo sapiens

<400> SEQUENCE: 208
ucgccgucuc cuucuggaa                                                19

<210> SEQ ID NO 209
<211> LENGTH: 21
<212> TYPE: DNA
<213> ORGANISM: Homo sapiens

<400> SEQUENCE: 209
aagagaggaa tatcaccgga a                                             21

<210> SEQ ID NO 210
<211> LENGTH: 21
<212> TYPE: DNA
<213> ORGANISM: Homo sapiens

<400> SEQUENCE: 210
aatatcaccg gaaccagggt g                                             21

<210> SEQ ID NO 211
<211> LENGTH: 21
<212> TYPE: DNA
<213> ORGANISM: Homo sapiens

<400> SEQUENCE: 211
aaccagggtg aaggtgcccg t                                             21

```
<210> SEQ ID NO 212
<211> LENGTH: 21
<212> TYPE: DNA
<213> ORGANISM: Homo sapiens

<400> SEQUENCE: 212
aaggtgcccg tggggcagga g                                              21

<210> SEQ ID NO 213
<211> LENGTH: 21
<212> TYPE: DNA
<213> ORGANISM: Homo sapiens

<400> SEQUENCE: 213
aacatcctgg gcttggtagt g                                              21

<210> SEQ ID NO 214
<211> LENGTH: 21
<212> TYPE: DNA
<213> ORGANISM: Homo sapiens

<400> SEQUENCE: 214
aagctggggc ctgaagggga g                                              21

<210> SEQ ID NO 215
<211> LENGTH: 21
<212> TYPE: DNA
<213> ORGANISM: Homo sapiens

<400> SEQUENCE: 215
aaggggagct gcttatccgc t                                              21

<210> SEQ ID NO 216
<211> LENGTH: 21
<212> TYPE: DNA
<213> ORGANISM: Homo sapiens

<400> SEQUENCE: 216
aactccttca atgaggccac c                                              21

<210> SEQ ID NO 217
<211> LENGTH: 21
<212> TYPE: DNA
<213> ORGANISM: Homo sapiens

<400> SEQUENCE: 217
aatgaggcca ccatggttct g                                              21

<210> SEQ ID NO 218
<211> LENGTH: 21
<212> TYPE: DNA
<213> ORGANISM: Homo sapiens

<400> SEQUENCE: 218
aagatcgtgg agatggagga t                                              21

<210> SEQ ID NO 219
<211> LENGTH: 21
<212> TYPE: DNA
<213> ORGANISM: Homo sapiens

<400> SEQUENCE: 219
aagtacattc tgtgctgcct g                                              21
```

```
<210> SEQ ID NO 220
<211> LENGTH: 21
<212> TYPE: DNA
<213> ORGANISM: Homo sapiens

<400> SEQUENCE: 220
aaaaacccct accgcttcct g                                              21

<210> SEQ ID NO 221
<211> LENGTH: 21
<212> TYPE: DNA
<213> ORGANISM: Homo sapiens

<400> SEQUENCE: 221 aaaacccta ccgcttcctg t                                               21

<210> SEQ ID NO 222
<211> LENGTH: 21
<212> TYPE: DNA
<213> ORGANISM: Homo sapiens

<400> SEQUENCE: 222 aaaccccta cgcttcctgt g                                               21

<210> SEQ ID NO 223
<211> LENGTH: 21
<212> TYPE: DNA
<213> ORGANISM: Homo sapiens

<400> SEQUENCE: 223 aaccccta cgcttcctgtg g                                               21

<210> SEQ ID NO 224
<211> LENGTH: 21
<212> TYPE: DNA
<213> ORGANISM: Homo sapiens

<400> SEQUENCE: 224
aagtgcgtgg aggagaataa t                                              21

<210> SEQ ID NO 225
<211> LENGTH: 21
<212> TYPE: DNA
<213> ORGANISM: Homo sapiens

<400> SEQUENCE: 225
aataatggcg tggccaagca c                                              21

<210> SEQ ID NO 226
<211> LENGTH: 21
<212> TYPE: DNA
<213> ORGANISM: Homo sapiens

<400> SEQUENCE: 226
aatggcgtgg ccaagcacat c                                              21

<210> SEQ ID NO 227
<211> LENGTH: 21
<212> TYPE: DNA
<213> ORGANISM: Homo sapiens

<400> SEQUENCE: 227
```
aagcacatca gccgtttcat c                                              21

<210> SEQ ID NO 228
<211> LENGTH: 21
<212> TYPE: DNA
<213> ORGANISM: Homo sapiens

<400> SEQUENCE: 228
aacatggacg gtgccgcgct c                                              21

<210> SEQ ID NO 229
<211> LENGTH: 21
<212> TYPE: DNA
<213> ORGANISM: Homo sapiens

<400> SEQUENCE: 229
aaagatcatc accatcctgg t                                              21

<210> SEQ ID NO 230
<211> LENGTH: 21
<212> TYPE: DNA
<213> ORGANISM: Homo sapiens

<400> SEQUENCE: 230
aagatcatca ccatcctggt c                                              21

<210> SEQ ID NO 231
<211> LENGTH: 21
<212> TYPE: DNA
<213> ORGANISM: Homo sapiens

<400> SEQUENCE: 231
aagcagtcaa cctcccggtc g                                              21

<210> SEQ ID NO 232
<211> LENGTH: 21
<212> TYPE: DNA
<213> ORGANISM: Homo sapiens

<400> SEQUENCE: 232
aacctcccgg tcgaccatat c                                              21

<210> SEQ ID NO 233
<211> LENGTH: 21
<212> TYPE: DNA
<213> ORGANISM: Homo sapiens

<400> SEQUENCE: 233
aatgtagaag gtgacgctct g                                              21

<210> SEQ ID NO 234
<211> LENGTH: 21
<212> TYPE: DNA
<213> ORGANISM: Homo sapiens

<400> SEQUENCE: 234
aaggtgacgc tctgggggca g                                              21

<210> SEQ ID NO 235
<211> LENGTH: 21
<212> TYPE: DNA
<213> ORGANISM: Homo sapiens

<400> SEQUENCE: 235
aaaattacgt ggaccgtacg g                                              21

<210> SEQ ID NO 236
<211> LENGTH: 21
<212> TYPE: DNA
<213> ORGANISM: Homo sapiens

<400> SEQUENCE: 236
aaattacgtg gaccgtacgg a                                              21

<210> SEQ ID NO 237
<211> LENGTH: 21
<212> TYPE: DNA
<213> ORGANISM: Homo sapiens

<400> SEQUENCE: 237
aattacgtgg accgtacgga g                                              21

<210> SEQ ID NO 238
<211> LENGTH: 21
<212> TYPE: DNA
<213> ORGANISM: Homo sapiens

<400> SEQUENCE: 238
aagcacagag cctgagttga t                                              21

<210> SEQ ID NO 239
<211> LENGTH: 21
<212> TYPE: DNA
<213> ORGANISM: Homo sapiens

<400> SEQUENCE: 239
aagtgaagag tgagctgccc c                                              21

<210> SEQ ID NO 240
<211> LENGTH: 21
<212> TYPE: DNA
<213> ORGANISM: Homo sapiens

<400> SEQUENCE: 240
aagagtgagc tgcccctgga t                                              21

<210> SEQ ID NO 241
<211> LENGTH: 21
<212> TYPE: DNA
<213> ORGANISM: Homo sapiens

<400> SEQUENCE: 241
aaggaaaccc cctcctcaaa c                                              21

<210> SEQ ID NO 242
<211> LENGTH: 21
<212> TYPE: DNA
<213> ORGANISM: Homo sapiens

<400> SEQUENCE: 242
aaaccccctc ctcaaacact a                                              21

<210> SEQ ID NO 243
<211> LENGTH: 21
<212> TYPE: DNA
<213> ORGANISM: Homo sapiens

```
<400> SEQUENCE: 243
aaacactatc gggggcccgc a                                              21

<210> SEQ ID NO 244
<211> LENGTH: 21
<212> TYPE: DNA
<213> ORGANISM: Homo sapiens

<400> SEQUENCE: 244
aacactatcg ggggcccgca g                                              21

<210> SEQ ID NO 245
<211> LENGTH: 21
<212> TYPE: DNA
<213> ORGANISM: Homo sapiens

<400> SEQUENCE: 245
aagagaggaa tatcaccgga a                                              21

<210> SEQ ID NO 246
<211> LENGTH: 21
<212> TYPE: DNA
<213> ORGANISM: Homo sapiens

<400> SEQUENCE: 246
tatcaccgga accagggtga a                                              21

<210> SEQ ID NO 247
<211> LENGTH: 21
<212> TYPE: DNA
<213> ORGANISM: Homo sapiens

<400> SEQUENCE: 247
gcaggaggtg gagggatga a                                               21

<210> SEQ ID NO 248
<211> LENGTH: 21
<212> TYPE: DNA
<213> ORGANISM: Homo sapiens

<400> SEQUENCE: 248
ctttggtgtg gcgctgcgga a                                              21

<210> SEQ ID NO 249
<211> LENGTH: 21
<212> TYPE: DNA
<213> ORGANISM: Homo sapiens

<400> SEQUENCE: 249
ctgcggaagc tggggcctga a                                              21

<210> SEQ ID NO 250
<211> LENGTH: 21
<212> TYPE: DNA
<213> ORGANISM: Homo sapiens

<400> SEQUENCE: 250
gctgcttatc cgcttcttca a                                              21

<210> SEQ ID NO 251
<211> LENGTH: 21
<212> TYPE: DNA
<213> ORGANISM: Homo sapiens
```

```
<400> SEQUENCE: 251
ccgcttcttc aactccttca a                                              21

<210> SEQ ID NO 252
<211> LENGTH: 21
<212> TYPE: DNA
<213> ORGANISM: Homo sapiens

<400> SEQUENCE: 252
catgttcctg gtggctggca a                                              21

<210> SEQ ID NO 253
<211> LENGTH: 21
<212> TYPE: DNA
<213> ORGANISM: Homo sapiens

<400> SEQUENCE: 253
actctttgcc cgccttggca a                                              21

<210> SEQ ID NO 254
<211> LENGTH: 21
<212> TYPE: DNA
<213> ORGANISM: Homo sapiens

<400> SEQUENCE: 254
ctacttcctc ttcacccgca a                                              21

<210> SEQ ID NO 255
<211> LENGTH: 21
<212> TYPE: DNA
<213> ORGANISM: Homo sapiens

<400> SEQUENCE: 255
tacttcctct tcacccgcaa a                                              21

<210> SEQ ID NO 256
<211> LENGTH: 21
<212> TYPE: DNA
<213> ORGANISM: Homo sapiens

<400> SEQUENCE: 256
cttcctcttc acccgcaaaa a                                              21

<210> SEQ ID NO 257
<211> LENGTH: 21
<212> TYPE: DNA
<213> ORGANISM: Homo sapiens

<400> SEQUENCE: 257
cacgctgccg ctgatgatga a                                              21

<210> SEQ ID NO 258
<211> LENGTH: 21
<212> TYPE: DNA
<213> ORGANISM: Homo sapiens

<400> SEQUENCE: 258
gatgaagtgc gtggaggaga a                                              21

<210> SEQ ID NO 259
<211> LENGTH: 21
<212> TYPE: DNA
```

```
<213> ORGANISM: Homo sapiens

<400> SEQUENCE: 259
gaagtgcgtg gaggagaata a                                              21

<210> SEQ ID NO 260
<211> LENGTH: 21
<212> TYPE: DNA
<213> ORGANISM: Homo sapiens

<400> SEQUENCE: 260
ggagaataat ggcgtggcca a                                              21

<210> SEQ ID NO 261
<211> LENGTH: 21
<212> TYPE: DNA
<213> ORGANISM: Homo sapiens

<400> SEQUENCE: 261
gcccatcggc gccaccgtca a                                              21

<210> SEQ ID NO 262
<211> LENGTH: 21
<212> TYPE: DNA
<213> ORGANISM: Homo sapiens

<400> SEQUENCE: 262
gcagtccttg gacttcgtaa a                                              21

<210> SEQ ID NO 263
<211> LENGTH: 21
<212> TYPE: DNA
<213> ORGANISM: Homo sapiens

<400> SEQUENCE: 263
agcagtcctt ggacttcgta a                                              21

<210> SEQ ID NO 264
<211> LENGTH: 21
<212> TYPE: DNA
<213> ORGANISM: Homo sapiens

<400> SEQUENCE: 264
catcatcctc gaagcagtca a                                              21

<210> SEQ ID NO 265
<211> LENGTH: 21
<212> TYPE: DNA
<213> ORGANISM: Homo sapiens

<400> SEQUENCE: 265
actctggcca tcatcctcga a                                              21

<210> SEQ ID NO 266
<211> LENGTH: 21
<212> TYPE: DNA
<213> ORGANISM: Homo sapiens

<400> SEQUENCE: 266
tgtaccgtcc tcaatgtaga a                                              21

<210> SEQ ID NO 267
<211> LENGTH: 21
```

<212> TYPE: DNA
<213> ORGANISM: Homo sapiens

<400> SEQUENCE: 267
ccggtcctgt accgtcctca a                                              21

<210> SEQ ID NO 268
<211> LENGTH: 21
<212> TYPE: DNA
<213> ORGANISM: Homo sapiens

<400> SEQUENCE: 268
gggggcagga ctcctccaaa a                                              21

<210> SEQ ID NO 269
<211> LENGTH: 21
<212> TYPE: DNA
<213> ORGANISM: Homo sapiens

<400> SEQUENCE: 269 tggggcagg actcctccaa a                                               21

<210> SEQ ID NO 270
<211> LENGTH: 21
<212> TYPE: DNA
<213> ORGANISM: Homo sapiens

<400> SEQUENCE: 270
ctgggggcag gactcctcca a                                              21

<210> SEQ ID NO 271
<211> LENGTH: 21
<212> TYPE: DNA
<213> ORGANISM: Homo sapiens

<400> SEQUENCE: 271
tggaccgtac ggagtcgaga a                                              21

<210> SEQ ID NO 272
<211> LENGTH: 21
<212> TYPE: DNA
<213> ORGANISM: Homo sapiens

<400> SEQUENCE: 272
acagagcctg agttgataca a                                              21

<210> SEQ ID NO 273
<211> LENGTH: 21
<212> TYPE: DNA
<213> ORGANISM: Homo sapiens

<400> SEQUENCE: 273
gcctgagttg atacaagtga a                                              21

<210> SEQ ID NO 274
<211> LENGTH: 21
<212> TYPE: DNA
<213> ORGANISM: Homo sapiens

<400> SEQUENCE: 274
ctgccagtcc ccactgagga a                                              21

<210> SEQ ID NO 275

```
<211> LENGTH: 21
<212> TYPE: DNA
<213> ORGANISM: Homo sapiens

<400> SEQUENCE: 275
cagtccccac tgaggaagga a                                              21

<210> SEQ ID NO 276
<211> LENGTH: 21
<212> TYPE: DNA
<213> ORGANISM: Homo sapiens

<400> SEQUENCE: 276
ggaaggaaac ccctcctca a                                               21

<210> SEQ ID NO 277
<211> LENGTH: 21
<212> TYPE: DNA
<213> ORGANISM: Homo sapiens

<400> SEQUENCE: 277
gaaggaaacc ccctcctcaa a                                              21

<210> SEQ ID NO 278
<211> LENGTH: 21
<212> TYPE: DNA
<213> ORGANISM: Homo sapiens

<400> SEQUENCE: 278
tgccacggtc gcctctgaga a                                              21

<210> SEQ ID NO 279
<211> LENGTH: 21
<212> TYPE: DNA
<213> ORGANISM: Homo sapiens

<400> SEQUENCE: 279
acggtcgcct ctgagaagga a                                              21

<210> SEQ ID NO 280
<211> LENGTH: 21
<212> TYPE: DNA
<213> ORGANISM: Homo sapiens

<400> SEQUENCE: 280
gagaaggaat cagtcatgta a                                              21

<210> SEQ ID NO 281
<211> LENGTH: 19
<212> TYPE: DNA
<213> ORGANISM: Homo sapiens

<400> SEQUENCE: 281
gagaggaata tcaccggaa                                                 19

<210> SEQ ID NO 282
<211> LENGTH: 19
<212> TYPE: DNA
<213> ORGANISM: Homo sapiens

<400> SEQUENCE: 282
gctggggcct gaaggggag                                                 19
```

```
<210> SEQ ID NO 283
<211> LENGTH: 19
<212> TYPE: DNA
<213> ORGANISM: Homo sapiens

<400> SEQUENCE: 283
taatggcgtg gccaagcac                                               19

<210> SEQ ID NO 284
<211> LENGTH: 19
<212> TYPE: DNA
<213> ORGANISM: Homo sapiens

<400> SEQUENCE: 284
tggcgtggcc aagcacatc                                               19

<210> SEQ ID NO 285
<211> LENGTH: 19
<212> TYPE: DNA
<213> ORGANISM: Homo sapiens

<400> SEQUENCE: 285
catggacggt gccgcgctc                                               19

<210> SEQ ID NO 286
<211> LENGTH: 19
<212> TYPE: DNA
<213> ORGANISM: Homo sapiens

<400> SEQUENCE: 286
aattacgtgg accgtacgg                                               19

<210> SEQ ID NO 287
<211> LENGTH: 19
<212> TYPE: DNA
<213> ORGANISM: Homo sapiens

<400> SEQUENCE: 287
attacgtgga ccgtacgga                                               19

<210> SEQ ID NO 288
<211> LENGTH: 19
<212> TYPE: DNA
<213> ORGANISM: Homo sapiens

<400> SEQUENCE: 288
ttacgtggac cgtacggag                                               19

<210> SEQ ID NO 289
<211> LENGTH: 19
<212> TYPE: DNA
<213> ORGANISM: Homo sapiens

<400> SEQUENCE: 289
gcacagagcc tgagttgat                                               19

<210> SEQ ID NO 290
<211> LENGTH: 19
<212> TYPE: DNA
<213> ORGANISM: Homo sapiens

<400> SEQUENCE: 290
gagaggaata tcaccggaa                                               19
```

<210> SEQ ID NO 291
<211> LENGTH: 19
<212> TYPE: DNA
<213> ORGANISM: Homo sapiens

<400> SEQUENCE: 291
agaataatgg cgtggccaa                                                 19

<210> SEQ ID NO 292
<211> LENGTH: 19
<212> TYPE: DNA
<213> ORGANISM: Homo sapiens

<400> SEQUENCE: 292
tcatcctcga agcagtcaa                                                 19

<210> SEQ ID NO 293
<211> LENGTH: 19
<212> TYPE: DNA
<213> ORGANISM: Homo sapiens

<400> SEQUENCE: 293
ggtcctgtac cgtcctcaa                                                 19

<210> SEQ ID NO 294
<211> LENGTH: 19
<212> TYPE: DNA
<213> ORGANISM: Homo sapiens

<400> SEQUENCE: 294
gaccgtacgg agtcgagaa                                                 19

<210> SEQ ID NO 295
<211> LENGTH: 19
<212> TYPE: DNA
<213> ORGANISM: Homo sapiens

<400> SEQUENCE: 295
agagcctgag ttgatacaa                                                 19

<210> SEQ ID NO 296
<211> LENGTH: 19
<212> TYPE: DNA
<213> ORGANISM: Homo sapiens

<400> SEQUENCE: 296
ccacggtcgc ctctgagaa                                                 19

<210> SEQ ID NO 297
<211> LENGTH: 19
<212> TYPE: DNA
<213> ORGANISM: Homo sapiens

<400> SEQUENCE: 297
ggtcgcctct gagaaggaa                                                 19

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

```
<400> SEQUENCE: 298
aagagaggaa uauuaccgga a                                           21

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 299 aauauccaccg gaaccagggu g                                          21

<210> SEQ ID NO 300
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 300
aaccagggug aaggugcccg u                                           21

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 301
aaggugcccg uggggcagga g                                           21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 302
aacauccugg gcuugguagu g                                           21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 303
aagcuggggc cugaagggga g                                           21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 304
```
aaggggagcu gcuuauccgc u                                        21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 305
aacuccuuca augaggccac c                                        21

<210> SEQ ID NO 306
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 306
aaugaggcca ccaugguucu g                                        21

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 307
aagaucgugg agauggagga u                                        21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 308
aaguacauuc ugugcugccu g                                        21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 309
aaaaacsccu accgcuuccu g                                        21

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 310
aaaaccccua ccgcuuccug u                          21

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 311
aaaccccuac cgcuuccugu g                          21

<210> SEQ ID NO 312
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 312
aaccccuacc gcuuccugug g                          21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 313
aagugcgugg aggagaauaa u                          21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 314
aauaauggcg uggccaagca c                          21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 315
aauggcgugg ccaagcacau c                          21

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 316
aagcacauca gccguuucau c                          21

```
<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 317
aacauggacg gugccgcgcu c                                              21

<210> SEQ ID NO 318
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 318
aaagaucauc accauccugg u                                              21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 319
aagaucauca ccauccuggu c                                              21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 320
aagcagucaa ccucccgguc g                                              21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 321
aaccucccgg ucgaccauau c                                              21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 322
aauguagaag gugacgcucu g                                              21
```

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 323
aaggugacgc ucuggggca g                                               21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 324
aaaauuacgu ggaccguacg g                                              21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 325
aaauuacgug gaccguacgg a                                              21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 326
aauuacgugg accguacgga g                                              21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 327
aagcacagag ccugaguuga u                                              21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 328
aagugaagag ugagcugccc c                                              21

```
<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 329
aagagugagc ugccccugga u                                              21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 330
aaggaaaccc ccuccucaaa c                                              21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 331 aaaccccuc cucaaacacu a                                               21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 332
aaacacuauc gggggcccgc a                                              21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 333
aacacuaucg ggggcccgca g                                              21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 334
aagagaggaa uaucaccgga a                                              21

<210> SEQ ID NO 335
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 335
uaucaccgga accaggguga a                                             21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 336
gcaggaggug gagggauga a                                              21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 337 cuuggugug gcgcugcgga a                                              21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 338
cugcggaagc uggggccuga a                                             21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 339
gcugcuuauc cgcuucuuca a                                             21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 340
ccgcuucuuc aacuccuuca a                                             21

<210> SEQ ID NO 341
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 341
cauguuccug guggcuggca a                                              21

<210> SEQ ID NO 342
<211> LENGTH: 21
<212> TYPE: RNA
<213> ORGANISM: Homo sapiens

<400> SEQUENCE: 342
acucuuugcc cgccuuggca a                                              21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 343
cuacuuccuc uucacccgca a                                              21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 344
uacuuccucu ucacccgcaa a                                              21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 345
cuuccucuuc acccgcaaaa a                                              21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 346
cacgcugccg cugaugauga a                                              21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
``` siRNA sense strand

<400> SEQUENCE: 347
gaugaagugc guggaggaga a                                              21

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 348
gaagugcgug gaggagaaua a                                              21

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 349
ggagaauaau ggcguggcca a                                              21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 350
gcccaucggc gccaccguca a                                              21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 351
gcaguccuug gacuucguaa a                                              21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 352 agcagccuu ggacuucgua a                                               21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 353
caucauccuc gaagcaguca a				21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 354
acucuggcca ucauccucga a				21

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 355
uguaccgucc ucaauguaga a				21

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 356
ccgguccugu accguccuca a				21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 357
gggggcagga cuccuccaaa a				21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 358 uggggggcagg acuccuccaa a				21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 359 cuggggcag gacuccucca a                                              21

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 360
uggaccguac ggagucgaga a                                             21

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 361
acagagccug aguugauaca a                                             21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 362
gccugaguug auacaaguga a                                             21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 363
cugccagucc ccacugagga a                                             21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 364
cuguccccac ugaggaagga a                                             21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 365
ggaaggaaac ccccuccuca a                                                21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 366
gaaggaaacc cccuccucaa a                                                21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 367
ugccacgguc gccucugaga a                                                21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 368
acggucgccu cugagaagga a                                                21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 369
gagaaggaau cagucaugua a                                                21

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 370
gagaggaaua ucaccggaa                                                   19

<210> SEQ ID NO 371
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 371
cuccuucaau gaggccacc                                                19

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 372
uaauggcgug gccaagcac                                                19

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 373
uggcguggcc aagcacauc                                                19

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 374
cauggacggu gccgcgcuc                                                19

<210> SEQ ID NO 375
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 375
aauuacgugg accguacgg                                                19

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 376
auuacgugga ccguacgga                                                19

<210> SEQ ID NO 377
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 377
uuacguggac cguacggag                                                19

<210> SEQ ID NO 378
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 378
gcacagagcc ugaguugau                                                   19

<210> SEQ ID NO 379
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 379
gagaggaaua ucaccggaa                                                   19

<210> SEQ ID NO 380
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 380
agaauaaugg cguggccaa                                                   19

<210> SEQ ID NO 381
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 381
ucauccucga agcagucaa                                                   19

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 382
gguccuguac cguccucaa                                                   19

<210> SEQ ID NO 383
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 383
gaccguacgg agucgagaa                                                   19

```
<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 384
agagccugag uugauacaa                                                      19

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 385
ccacggucgc cucugagaa                                                      19

<210> SEQ ID NO 386
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sense strand

<400> SEQUENCE: 386
ggucgccucu gagaaggaa                                                      19

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (22)..(23)
<223> OTHER INFORMATION: deoxythymidine

<400> SEQUENCE: 387
cuucgccacc uaccugcuca att                                                 23

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA antisense sequence
<220> FEATURE:
<223> OTHER INFORMATION: Description of Combined DNA/RNA Molecule:
      Synthetic siRNA antisense sequence
<220> FEATURE:
<221> NAME/KEY: modified_base
<222> LOCATION: (22)..(23)
<223> OTHER INFORMATION: deoxythymidine

<400> SEQUENCE: 388
uugagcaggu agguggcgaa gtt                                                 23
```

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (20)..(21)
<223> OTHER INFORMATION: deoxythymidine

<400> SEQUENCE: 389
ucgccaccua ccugcucaat t                                              21

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand
<220> FEATURE:
<221> NAME/KEY: modified_base
<222> LOCATION: (20)..(21)
<223> OTHER INFORMATION: deoxythymidine

<400> SEQUENCE: 390
uugagcaggu agguggcgat t                                              21

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (22)..(23)
<223> OTHER INFORMATION: deoxythymidine

<400> SEQUENCE: 391
cgugaacugc uacagcguga att                                            23

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand
<220> FEATURE:
<221> NAME/KEY: modified_base
<222> LOCATION: (22)..(23)
<223> OTHER INFORMATION: deoxythymidine

<400> SEQUENCE: 392
uucacucugu agcaguucac gtt                                            23

```
<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (20)..(21)
<223> OTHER INFORMATION: deoxythymidine

<400> SEQUENCE: 393
ugaacugcua cagcgugaat t                                              21

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand
<220> FEATURE:
<221> NAME/KEY: modified_base
<222> LOCATION: (20)..(21)
<223> OTHER INFORMATION: deoxythymidine

<400> SEQUENCE: 394
uucacucugu agcaguucat t                                              21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (20)..(21)
<223> OTHER INFORMATION: deoxythymidine

<400> SEQUENCE: 395
ugaacugcua cagcgugaat t                                              21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense strand

<400> SEQUENCE: 396
uucacucugu agcaguucac g                                              21

<210> SEQ ID NO 397
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (22)..(23)
<223> OTHER INFORMATION: deoxythymidine

<400> SEQUENCE: 397 ccguccugu accguccuca att                                              23

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand
<220> FEATURE:
<221> NAME/KEY: modified_base
<222> LOCATION: (22)..(23)
<223> OTHER INFORMATION: deoxythymidine

<400> SEQUENCE: 398
uugaggacgg uacaggaccg gtt                                             23

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (20)..(21)
<223> OTHER INFORMATION: deoxythymidine

<400> SEQUENCE: 399
gguccuguac cguccucaat t                                               21

<210> SEQ ID NO 400
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand
<220> FEATURE:
<221> NAME/KEY: modified_base
<222> LOCATION: (20)..(21)
<223> OTHER INFORMATION: deoxythymidine

<400> SEQUENCE: 400
uugaggacgg uacaggacct t                                               21

<210> SEQ ID NO 401
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (20)..(21)
<223> OTHER INFORMATION: deoxythymidine

<400> SEQUENCE: 401
gguccuguac cguccucaat t                                              21

<210> SEQ ID NO 402
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense strand

<400> SEQUENCE: 402
uugaggacgg uacaggaccg g                                              21

<210> SEQ ID NO 403
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (22)..(23)
<223> OTHER INFORMATION: deoxythymidine

<400> SEQUENCE: 403
ugccacgguc gccucugaga att                                            23

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand
<220> FEATURE:
<221> NAME/KEY: modified_base
<222> LOCATION: (22)..(23)
<223> OTHER INFORMATION: deoxythymidine

<400> SEQUENCE: 404
uucucagagg cgaccguggc att                                            23

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
```

```
      Synthetic siRNA sense strand
<220> FEATURE:
<221> NAME/KEY: modified_base
<222> LOCATION: (20)..(21)
<223> OTHER INFORMATION: deoxythymidine

<400> SEQUENCE: 405
ccacggucgc cucugagaat t                                              21

<210> SEQ ID NO 406
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA antisense strand
<220> FEATURE:
<223> OTHER INFORMATION: Description of Combined DNA/RNA Molecule:
      Synthetic siRNA antisense strand
<220> FEATURE:
<221> NAME/KEY: modified_base
<222> LOCATION: (20)..(21)
<223> OTHER INFORMATION: deoxythymidine

<400> SEQUENCE: 406
uucucagagg cgaccguggt t                                              21

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sense strand
<220> FEATURE:
<223> OTHER INFORMATION: Description of Combined DNA/RNA Molecule:
      Synthetic siRNA sense strand
<220> FEATURE:
<221> NAME/KEY: modified_base
<222> LOCATION: (20)..(21)
<223> OTHER INFORMATION: deoxythymidine

<400> SEQUENCE: 407
ccacggucgc cucugagaat t                                              21

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense strand

<400> SEQUENCE: 408
uucucagagg cgaccguggc a                                              21

<210> SEQ ID NO 409

<400> SEQUENCE: 409

000

<210> SEQ ID NO 410

<400> SEQUENCE: 410

000

<210> SEQ ID NO 411
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 411
uugagcaggu agguggcgaa g                                            21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 412
uugagcaggu agguggcgau g                                            21

<210> SEQ ID NO 413
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 413
cgccgcuagc gcgcgccgcu u                                            21

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 414
cuucucccgc gccucuuccu u                                            21

<210> SEQ ID NO 415
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 415
gcaucuucuc ccgcgccucu u                                            21

<210> SEQ ID NO 416
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 416
gcucuuggcg gccagcaucu u                                            21

<210> SEQ ID NO 417
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 417
cgccgagccg uccgcgcucu u                                              21

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 418
gccguugagc agcgugaugu u                                              21

<210> SEQ ID NO 419
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 419
ccccggcgag ccugccuccu u                                              21

<210> SEQ ID NO 420
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 420
ggcguagucg ccgcccgauu u                                              21

<210> SEQ ID NO 421
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 421
aggcguaguc gccgcccgau u                                              21

<210> SEQ ID NO 422
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 422
gagcagcucg auccagagcu u                                              21

<210> SEQ ID NO 423
<211> LENGTH: 21
<212> TYPE: RNA
```

<213> ORGANISM: Artificial Sequence
<220> FEATURE:
<223> OTHER INFORMATION: Description of Artificial Sequence: Synthetic
      siRNA antisense sequence

<400> SEQUENCE: 423
gcaggugggg aagagcggcu u                                          21

<210> SEQ ID NO 424
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 424
gcagaggcag gccacgagcu u                                          21

<210> SEQ ID NO 425
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 425
ggccuucacg cuguagcagu u                                          21

<210> SEQ ID NO 426
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 426
cuggacccgg guggcggccu u                                          21

<210> SEQ ID NO 427
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 427
cagggccagg gccaggagcu u                                          21

<210> SEQ ID NO 428
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 428
uagauuggac acaucacccu u                                          21

<210> SEQ ID NO 429
<211> LENGTH: 21
<212> TYPE: RNA
<213> ORGANISM: Artificial Sequence

```
<220> FEATURE:
<223> OTHER INFORMATION: Description of Artificial Sequence: Synthetic
      siRNA antisense sequence

<400> SEQUENCE: 429
ugagaaguug ggaucuagau u                                              21

<210> SEQ ID NO 430
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 430
ggugccuuca aaugagaagu u                                              21

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 431
ccacauccag uuuggugccu u                                              21

<210> SEQ ID NO 432
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 432
aauguucccc acauccaguu u                                              21

<210> SEQ ID NO 433
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 433
caauguuccc cacauccagu u                                              21

<210> SEQ ID NO 434
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 434
guauaaugcc agcacaaugu u                                              21

<210> SEQ ID NO 435
<211> LENGTH: 21
<212> TYPE: RNA
<213> ORGANISM: Artificial Sequence
<220> FEATURE:
```

<223> OTHER INFORMATION: Description of Artificial Sequence: Synthetic
      siRNA antisense sequence

<400> SEQUENCE: 435
ugugacgaaa uucaaguaau u                                              21

<210> SEQ ID NO 436
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 436 cauuccucu gugacgaaau u                                               21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 437
uucuguaggg guugaucauu u                                              21

<210> SEQ ID NO 438
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 438
uuucuguagg gguugaucau u                                              21

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 439
gggcagguuu cuguaggggu u                                              21

<210> SEQ ID NO 440
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 440
augauggcca ggggcagguu u                                              21

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic siRNA antisense sequence

<400> SEQUENCE: 441
gaugauggcc aggggcaggu u                                              21

<210> SEQ ID NO 442
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 442
gguggugaag uaggccaggu u                                              21

<210> SEQ ID NO 443
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 443
caugacgccc aggugauagu u                                              21

<210> SEQ ID NO 444
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 444
ggaugugaac agggacccau u                                              21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 445
ggauggaggg cagguggccu u                                              21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 446
gaugacggag aagauguccu u                                              21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence -continued

<400> SEQUENCE: 447
guugaagaag cugaagaagu u                                              21

<210> SEQ ID NO 448
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 448
cagggccacg cagagccagu u                                              21

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 449
ggccgcucaa gcucaggcuu u                                              21

<210> SEQ ID NO 450
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 450
gggccgcuca agcucaggcu u                                              21

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 451
aggcagggcc agguucaccu u                                              21

<210> SEQ ID NO 452
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 452
gaacacaggc agggccaggu u                                              21

<210> SEQ ID NO 453
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

```
<400> SEQUENCE: 453
gccacacucc acgggugucu u                                              21

<210> SEQ ID NO 454
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 454
gagccacuug ggcuuguuuu u                                              21

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 455
aggagccacu ugggcuuguu u                                              21

<210> SEQ ID NO 456
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 456
gaggagccac uugggcuugu u                                              21

<210> SEQ ID NO 457
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 457
cuggaggagc cacuugggcu u                                              21

<210> SEQ ID NO 458
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 458
gaugcccugg aggagccacu u                                              21

<210> SEQ ID NO 459
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 459
```
ggggaccacc ugcaugagcu u                                              21

<210> SEQ ID NO 460
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 460
uucuccucgg ccgccggcgc c                                              21

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 461
uuccuucucc ucggccgccg g                                              21

<210> SEQ ID NO 462
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 462
uuggcggcca gcaucuucuc c                                              21

<210> SEQ ID NO 463
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 463
uucucccgcg ccucuuccuu c                                              21

<210> SEQ ID NO 464
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 464
uuggcggcca gcaucuucuc c                                              21

<210> SEQ ID NO 465
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 465

-continued

| | |
|---|---|
| uuccgcugca gggucacgcc c | 21 |

<210> SEQ ID NO 466
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 466

| | |
|---|---|
| uugagcacgc ccgugggcgu c | 21 |

<210> SEQ ID NO 467
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 467

| | |
|---|---|
| uuggagaugg uggugccgag c | 21 |

<210> SEQ ID NO 468
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 468

| | |
|---|---|
| uuuggagaug guggugccga g | 21 |

<210> SEQ ID NO 469
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 469

| | |
|---|---|
| uugaggaagg cgggcagcga g | 21 |

<210> SEQ ID NO 470
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 470

| | |
|---|---|
| uugagcaggu agguggcgaa g | 21 |

<210> SEQ ID NO 471
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 471

| | |
|---|---|
| uuggcugccu ccucgggcac c | 21 |

-continued

<210> SEQ ID NO 472
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 472
uucacggccg ugagcagcag c                                              21

<210> SEQ ID NO 473
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 473
uucacgcugu agcaguucac g                                              21

<210> SEQ ID NO 474
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 474
uuggcggcgg caaaggcauc c                                              21

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 475
uucccgaucu ggacgaagcc c                                              21

<210> SEQ ID NO 476
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 476
uuggacacau cacccuuccc g                                              21

<210> SEQ ID NO 477
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 477
uugggaucua gauuggacac a                                              21

```
<210> SEQ ID NO 478
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 478
uucaaaugag aaguugggau c                                            21

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 479 uugguogccuu caaaugagaa g                                           21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 480
uuuggugccu ucaaaugaga a                                            21

<210> SEQ ID NO 481
<211> LENGTH: 20
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 481
uuccccacau ccaguuuggu                                              20

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 482
uuccauccuc cauaggcaaa g                                            21

<210> SEQ ID NO 483
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 483
uucaaguaau uccauccucc a                                            21
```

```
<210> SEQ ID NO 484
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 484 uuccucugu gacgaaauuc a                                              21

<210> SEQ ID NO 485
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 485
uugaucauuu ccucugugac g                                             21

<210> SEQ ID NO 486
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 486
uucuguaggg guugaucauu u                                             21

<210> SEQ ID NO 487
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 487
uucuguaggg guugaucauu u                                             21

<210> SEQ ID NO 488
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 488
uuggucagca cguacaccag c                                             21

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 489
uucccgaagu ccacggccac g                                             21

<210> SEQ ID NO 490
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 490
uugacggagc cgaagcagga c                                             21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 491
uucccgggac cccacgaaga a                                             21

<210> SEQ ID NO 492
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 492
uuggagaagg cguagagcag c                                             21

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 493
uugaugacgg agaagauguc c                                             21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 494
uugaagaagc ugaagaaguu g                                             21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 495
uucuguggcg cagccagauc a                                             21

<210> SEQ ID NO 496
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 496
uuucuguggc gcagccagau c                                              21

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 497
uugaugggcc gcucaagcuc a                                              21

<210> SEQ ID NO 498
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 498
uucaccuuga ugggccgcuc a                                              21

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 499
uuccagaagg agacggcgau c                                              21

<210> SEQ ID NO 500
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 500
uuccaccaga ccccgaagaa g                                              21

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 501
uuuccaccag accccgaaga a                                              21

<210> SEQ ID NO 502
<211> LENGTH: 21
<212> TYPE: RNA
```

<213> ORGANISM: Artificial Sequence
<220> FEATURE:
<223> OTHER INFORMATION: Description of Artificial Sequence: Synthetic
      siRNA antisense sequence

<400> SEQUENCE: 502
uuuuccacca gaccccgaag a                                            21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 503 uuuuccacc agaccccgaa g                                             21

<210> SEQ ID NO 504
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 504 uuguuuucc accagacccc g                                             21

<210> SEQ ID NO 505
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 505
uugggcuugu uuuccacca g                                             21

<210> SEQ ID NO 506
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 506
uucugacaca ggacggucgu g                                            21

<210> SEQ ID NO 507
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 507
gcucuuggcg gccagcauc                                               19

<210> SEQ ID NO 508
<211> LENGTH: 19
<212> TYPE: RNA
<213> ORGANISM: Artificial Sequence

```
<220> FEATURE:
<223> OTHER INFORMATION: Description of Artificial Sequence: Synthetic
      siRNA antisense sequence

<400> SEQUENCE: 508
gccguugagc agcgugaug                                                       19

<210> SEQ ID NO 509
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 509
gagcagcucg auccagagc                                                       19

<210> SEQ ID NO 510
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 510
ggccuucacg cuguagcag                                                       19

<210> SEQ ID NO 511
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 511
guauaaugcc agcacaaug                                                       19

<210> SEQ ID NO 512
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 512
gaugacggag aagaugucc                                                       19

<210> SEQ ID NO 513
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 513
uugagcaggu agguggcga                                                       19

<210> SEQ ID NO 514
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      siRNA antisense sequence

<400> SEQUENCE: 514
uugaugacgg agaagaugu                                                    19

<210> SEQ ID NO 515
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 515
uucuguggcg cagccagau                                                    19

<210> SEQ ID NO 516
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 516
uuccagaagg agacggcga                                                    19

<210> SEQ ID NO 517
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 517
uuccggugau auuccucucu u                                                 21

<210> SEQ ID NO 518
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 518
cacccugguu ccggugauau u                                                 21

<210> SEQ ID NO 519
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 519
acgggcaccu ucacccuggu u                                                 21

<210> SEQ ID NO 520
<211> LENGTH: 21
<212> TYPE: RNA
<213> ORGANISM: Artificial Sequence
<220> FEATURE:
<223> OTHER INFORMATION: Description of Artificial Sequence: Synthetic
``` siRNA antisense sequence

<400> SEQUENCE: 520
cuccugcccc acgggcaccu u                                              21

<210> SEQ ID NO 521
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 521
cacuaccaag cccaggaugu u                                              21

<210> SEQ ID NO 522
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 522
cuccccuuca ggccccagcu u                                              21

<210> SEQ ID NO 523
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 523
agcggauaag cagcucccu u                                               21

<210> SEQ ID NO 524
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 524
gguggccuca uugaaggagu u                                              21

<210> SEQ ID NO 525
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 525
cagaaccaug guggccucau u                                              21

<210> SEQ ID NO 526
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence -continued

<400> SEQUENCE: 526
auccuccauc uccacgaucu u                                          21

<210> SEQ ID NO 527
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 527
caggcagcac agaauguacu u                                          21

<210> SEQ ID NO 528
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 528
caggaagcgg uaggguuuu u                                           21

<210> SEQ ID NO 529
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 529
acaggaagcg guaggguuu u                                           21

<210> SEQ ID NO 530
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 530
cacaggaagc gguaggguu u                                           21

<210> SEQ ID NO 531
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 531
ccacaggaag cgguagggu u                                           21

<210> SEQ ID NO 532
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

```
<400> SEQUENCE: 532
auuauucucc uccacgcacu u                                              21

<210> SEQ ID NO 533
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 533
gugcuuggcc acgccauuau u                                              21

<210> SEQ ID NO 534
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 534
gaugugcuug gccacgccau u                                              21

<210> SEQ ID NO 535
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 535
gaugaaacgg cugaugugcu u                                              21

<210> SEQ ID NO 536
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 536
gagcgcggca ccguccaugu u                                              21

<210> SEQ ID NO 537
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 537
accaggaugg ugaugaucuu u                                              21

<210> SEQ ID NO 538
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 538
```
gaccaggaug gugaugaucu u                                    21

<210> SEQ ID NO 539
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 539
cgaccgggag guugacugcu u                                    21

<210> SEQ ID NO 540
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 540
gauauggucg accgggaggu u                                    21

<210> SEQ ID NO 541
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 541
cagagcguca ccuucuacau u                                    21

<210> SEQ ID NO 542
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 542
cugcccccag agcgucaccu u                                    21

<210> SEQ ID NO 543
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 543
ccguacgguc cacguaauuu u                                    21

<210> SEQ ID NO 544
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 544
uccguacggu ccacguaauu u                                         21

<210> SEQ ID NO 545
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 545
cuccguacgg uccacguaau u                                         21

<210> SEQ ID NO 546
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 546
aucaacucag gcucugugcu u                                         21

<210> SEQ ID NO 547
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 547
ggggcagcuc acucuucacu u                                         21

<210> SEQ ID NO 548
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 548
auccaggggc agcucacucu u                                         21

<210> SEQ ID NO 549
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 549
guuugaggag gggguuuccu u                                         21

<210> SEQ ID NO 550
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 550
uaguguuuga ggaggggguu u                                         21

<210> SEQ ID NO 551
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 551
ugcgggcccc cgauaguguu u                                            21

<210> SEQ ID NO 552
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 552
cugcgggccc ccgauagugu u                                            21

<210> SEQ ID NO 553
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 553
uuccggugau auuccucucu u                                            21

<210> SEQ ID NO 554
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 554
uucacccugg uuccggugau a                                            21

<210> SEQ ID NO 555
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 555
uucauccccu ccaccuccug c                                            21

<210> SEQ ID NO 556
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 556
uuccgcagcg ccacaccaaa g                                            21

```
<210> SEQ ID NO 557
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 557
uucaggcccc agcuuccgca g                                             21

<210> SEQ ID NO 558
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 558
uugaagaagc ggauaagcag c                                             21

<210> SEQ ID NO 559
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 559
uugaaggagu ugaagaagcg g                                             21

<210> SEQ ID NO 560
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 560
uugccagcca ccaggaacau g                                             21

<210> SEQ ID NO 561
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 561
uugccaaggc gggcaaagag u                                             21

<210> SEQ ID NO 562
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 562
uugcggguga agaggaagua g                                             21
```

```
<210> SEQ ID NO 563
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 563
uuugcgggug aagaggaagu a                                              21

<210> SEQ ID NO 564
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 564
uuuuugcggg ugaagaggaa g                                              21

<210> SEQ ID NO 565
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 565
uucaucauca gcggcagcgu g                                              21

<210> SEQ ID NO 566
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 566
uucuccucca cgcacuucau c                                              21

<210> SEQ ID NO 567
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 567
uuauucuccu ccacgcacuu c                                              21

<210> SEQ ID NO 568
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 568
uuggccacgc cauuauucuc c                                              21

<210> SEQ ID NO 569
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 569
uugacggugg cgccgauggg c                                              21

<210> SEQ ID NO 570
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 570
uuuacgaagu ccaaggacug c                                              21

<210> SEQ ID NO 571
<211> LENGTH: 22
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 571
uuacgaaguc caaggacugc ug                                             22

<210> SEQ ID NO 572
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 572
uugacugcuu cgaggaugau g                                              21

<210> SEQ ID NO 573
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 573
uucgaggaug auggccagag u                                              21

<210> SEQ ID NO 574
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 574
uucuacauug aggacgguac a                                              21

<210> SEQ ID NO 575
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 575
uugaggacgg uacaggaccg g                                            21

<210> SEQ ID NO 576
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 576
uuuuggagga guccugcccc c                                            21

<210> SEQ ID NO 577
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 577
uuuggaggag uccugccccc a                                            21

<210> SEQ ID NO 578
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 578
uuggaggagu ccugcccccca g                                           21

<210> SEQ ID NO 579
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 579
uucucgacuc cguacggucc a                                            21

<210> SEQ ID NO 580
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 580
uuguaucaac ucaggcucug u                                            21

<210> SEQ ID NO 581
<211> LENGTH: 21
<212> TYPE: RNA
```

<213> ORGANISM: Artificial Sequence
<220> FEATURE:
<223> OTHER INFORMATION: Description of Artificial Sequence: Synthetic
      siRNA antisense sequence

<400> SEQUENCE: 581
uucacuugua ucaacucagg c                                           21

<210> SEQ ID NO 582
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 582
uuccucagug gggacuggca g                                           21

<210> SEQ ID NO 583
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 583
uuccuuccuc agugggggacu g                                          21

<210> SEQ ID NO 584
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 584
uugaggaggg gguuuccuuc c                                           21

<210> SEQ ID NO 585
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 585
uuugaggagg ggguuuccuu c                                           21

<210> SEQ ID NO 586
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 586
uucucagagg cgaccguggc a                                           21

<210> SEQ ID NO 587
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 587
uuccuucuca gaggcgaccg u                                              21

<210> SEQ ID NO 588
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 588
uuacaugacu gauuccuucu c                                              21

<210> SEQ ID NO 589
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 589
uuccggugau auuccucuc                                                 19

<210> SEQ ID NO 590
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 590
gguggccuca uugaaggag                                                 19

<210> SEQ ID NO 591
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 591
gugcuuggcc acgccauua                                                 19

<210> SEQ ID NO 592
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 592
gaugugcuug gccacgcca                                                 19

<210> SEQ ID NO 593
<211> LENGTH: 19
<212> TYPE: RNA
<213> ORGANISM: Artificial Sequence
<220> FEATURE:

```
<223> OTHER INFORMATION: Description of Artificial Sequence: Synthetic
      siRNA antisense sequence

<400> SEQUENCE: 593
gagcgcggca ccguccaug                                              19

<210> SEQ ID NO 594
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 594
ccguacgguc cacguaauu                                              19

<210> SEQ ID NO 595
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 595
uccguacggu ccacguaau                                              19

<210> SEQ ID NO 596
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 596
cuccguacgg uccacguaa                                              19

<210> SEQ ID NO 597
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 597
aucaacucag gcucugugc                                              19

<210> SEQ ID NO 598
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 598
uuccggugau auuccucuc                                              19

<210> SEQ ID NO 599
<211> LENGTH: 19
<212> TYPE: RNA
<213> ORGANISM: Artificial Sequence
<220> FEATURE:
<223> OTHER INFORMATION: Description of Artificial Sequence: Synthetic
``` siRNA antisense sequence

<400> SEQUENCE: 599
uuggccacgc cauuauucu                    19

<210> SEQ ID NO 600
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 600
uugacugcuu cgaggauga                    19

<210> SEQ ID NO 601
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 601
uugaggacgg uacaggacc                    19

<210> SEQ ID NO 602
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 602
uucucgacuc cguacgguc                    19

<210> SEQ ID NO 603
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 603
uuguaucaac ucaggcucu                    19

<210> SEQ ID NO 604
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence

<400> SEQUENCE: 604
uucucagagg cgaccgugg                    19

<210> SEQ ID NO 605
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA antisense sequence -continued

```
<400> SEQUENCE: 605
uuccuucuca gaggcgacc                                                      19
```

ANTICANCER THERAPEUTIC INTERVENTION

SEQUENCE LISTING

The instant application contains a Sequence Listing which has been submitted electronically in ASCII format and is hereby incorporated by reference in its entirety. Said ASCII copy, created on Jul. 16, 2019, is named C64-026732_US_ORD_SL.txt and is 130,450 bytes in size.

FIELD OF THE INVENTION

The present invention is directed to a method of treating cancer using interfering RNA duplexes to mediate gene silencing. The present invention is also directed to interfering RNA duplexes and vectors encoding such interfering RNA duplexes.

DESCRIPTION OF RELATED ART

Regardless of their origin, tumours require a constant supply of nutrients to support their characteristic unabated growth. In fact, tumour cells may consume more nutrients than required for their own metabolic needs (Medina et al., 1992b), and exhibit distinct metabolic profiles compared to their normal cellular counterparts. Tumours are supplied with nutrients to fuel their metabolic needs through the collective processes of angiogenesis and the prodigious expression of nutrient transporters in the plasma membranes of constituent cells. Amino acids are the primary source of cellular nitrogen, used for nucleotide, glutathione, amino sugar and protein synthesis. The voracious and apparently wasteful amino acid metabolism of malignant tumours leads to, among other things, negative nitrogen balance in the host with cancer. Moreover, the carbon skeletons of amino acids are often utilized as an oxidative fuel source for ATP generation in addition to glucose and fatty acids, and may also contribute to sterol and lipid biosynthesis (Baggetto, 1992; Medina et al., 1992a). Compared to normal cells or tissues, cancer cells display enhanced and altered channelling of amino acids into select metabolic pathways, often in concert with the aerobic glycolysis characteristic of tumours (Baggetto, 1992) and (Mazurek et al., 2003). Solid tumours are often poorly vascularized, especially in the nascent avascular phase characteristic of neoplasia and metastases, so they must have efficient mechanisms for extracting plasma amino acids in order to compete with host tissues (Medina et al., 1992b). Cancer, in turn, is a microcosm of evolution, with the "fittest" cells enduring through adaptation to the local microenvironment; as a result, amino acid transporters with properties that impart growth and survival advantages are selected for and expressed, often at augmented levels compared to the parent tissue.

Prior to the advent of mammalian amino acid transporter cloning and isolation, Christensen proposed that specific amino acid transporters could be upregulated in transformed cells to support the high levels of protein synthesis necessary for growth and proliferation (Christensen, 1990). A search of the human expressed sequence tag (EST) database at the Cancer Genome Anatomy Project (CGAP) website (cgap.nci.nhi.gov), using the "cDNA Virtual northern" tool to determine the expression levels of the classic neutral amino acid transport "systems" A, ASC, L and N, in normal and cancerous tissues revealed that while five transporters are significantly enhanced overall in cancerous tissues, two stand out—LAT1 (large neutral amino acid transporter 1) and ASCT2 (ASC amino acid transporter 2) (Fuchs et al., 2005). ASCT2 and LAT1 are both upregulated three-fold (collectively) in a variety of cancerous tissues where their expression pattern is almost identical (Fuchs et al., 2005).

LAT1 has long been associated with cancerous or proliferative cells. When full-length LAT1 was first isolated and characterized in 1998, it was shown not to be expressed in rat liver but was detected in rat hepatoma (dRLh-84) and hepatocarcinoma (FAA-HTC1) cell lines (Kanai et al., 1998), which is consistent with the expression pattern of ASCT2 in human liver as discussed below. Northern blot analysis with human cell lines revealed TA1 expression in the choriocarcinoma cell line JEG-3 and breast carcinoma cell line MDA-A1 (Sang et al., 1995), as well as in stomach signet ring cell carcinoma (KATOIII), lung small cell carcinoma (RERF-LC-MA) and malignant melanoma (G-361) (Kanai et al., 1998). Both 4F2hc and LAT1 were detected in several leukemia cell lines, RERF-LC-MA lung small cell carcinoma cells, HeLa uterine cervical carcinoma cells and T-24 bladder carcinoma cells (Yanagida et al., 2001). The results with the T-24 cells have been confirmed by confocal immunofluorescence microscopy, which revealed colocalization of LAT1 and 4F2hc in the plasma membrane (Kim et al., 2002). LAT1 and 4F2hc have also been shown to colocalize in the plasma membrane of KB human oral epidermoid carcinoma cells (Yoon et al., 2005), and may be important for oral squamous epithelial carcinogenesis, as immunohistochemical staining has shown that their expression increases during progression of oral normal mucosa to oral squamous cell carcinoma (Kim et al., 2004b).

Kühne et al., (Kuhne et al., 2007) discloses genetic polymorphisms of the LAT1 and LAT2 genes and relates such polymorphisms to the pharmacokinetics of melphalan. Shennan et al., (Shennan et al., 2008) discloses that inhibiting LAT1 reduces the growth of human breast cancer cells. Nawashiro et al., (Nawashiro et al., 2006) discloses that LAT1 is a potential molecular target in human astrocytic tumors. Yamauchi et al., (Yamauchi et al., 2009) and Kim et al., (Kim et al., 2008) disclose the use of LAT1 inhibitors to block tumor activity of various cancer cells. In the context of the requirement of the 4F2hc chaperone for enabling LAT1 activity, real-time quantitative RT-PCR revealed similar levels of LAT1 and 4F2hc mRNA in KB cells (Yoon et al., 2005). This conflicts with the data from T-24 cells where LAT1 levels were ~1.5 fold higher than 4F2hc (Kim et al., 2002) and with results in MDA-MB-231 and MCF-7 human breast cancer cells, where LAT1 mRNA was ~4.3- and ~4.9-fold higher than 4F2hc (Shennan et al., 2004). Based on the data by (Fuchs et al., 2005), it appears that the overall abundance of 4F2hc mRNA is on par with that of LAT1, but it should be kept in mind that protein and mRNA levels are not always linearly correlated due to the multiple mechanisms of gene expression control. Moreover, cells undoubtedly possess mechanisms that adequately match protein levels of both components, such that 4F2hc is not rate-limiting for vital LAT1-related functions.

When colon cancer RCN-9 cells were injected into the spleen of rats, the size of the resultant metastatic liver tumors was directly correlated to LAT1 expression (Ohkame et al., 2001; Tamai et al., 2001). Thus, it has been proposed that inhibiting LAT1 function could serve as a potential therapeutic for many types of cancers (Kanai et al., 2001). To date, studies targeting LAT1 specifically are scarce. However, in vitro LAT1 antisense expression in non-human hepatic tumor cells resulted in a modest though statistically significant decrease in cell number, viability and S-phase cells over a 5-day period relative to controls despite the absence of a significant decrease in L-type transport over this period (Storey et al., 2005).

Antisense oligonucleotides directed against 4F2hc have been shown to inhibit Na$^+$-independent isoleucine transport in C6-BU-1 rat glioma cells (Broer et al., 1997), and leucine uptake in BeWo human cytotrophoblast cells (Kudo et al., 2004), but the effects on cell growth were not reported. An anti-4F2hc antibody inhibited the proliferation of a variety of tumor cell lines (Yagita et al., 1986), but it is possible that these effects were mediated through the collective effects on other 4F2 "light chains" in addition to LAT1, or to non-transport related functions of 4F2hc (Feral et al., 2005). Knockdown of LAT1 in T-24 cells with a LAT1-siRNA against nucleotides 1173-1194 in vitro led to a decrease in L-CSNO uptake (Li et al., 2005), but it is not reported whether cell survival was affected. Thus, mechanistic studies linking the LAT1 "light chain" to cancer growth remain to be reported.

The use of siRNA to inhibit LAT1 gene expression have been disclose by several groups (Kim et al., 2006a; Kim et al., 2006b; Kaneko et al., 2007; Pinho et al., 2007a; Yin et al., 2008; Kuhne et al., 2009; Nicklin et al., 2009; Xia et al., 2010; Liang et al., 2011; Miko et al., 2011; Ohkawa et al., 2011; Denoyer et al., 2012; Hayashi et al., 2012; Dickens et al., 2013; Hayashi et al., 2013; Youland et al., 2013; Gaccioli et al., 2015; Habermeier et al., 2015; Wongthai et al., 2015; Furugen et al., 2016; Polet et al., 2016; Straka et al., 2016; Tomblin et al., 2016; Wei et al., 2016; Xu et al., 2016; Liu et al., 2017).

More recently, LAT1 has been suggested as a marker of cancer prognosis in the types of cancer listed in the following table:

| | | |
|---|---|---|
| Kidney | Renal cell carcinoma | (Betsunoh et al., 2013) |
| | Urothelial carcinomas | (Eltz et al., 2008) |
| | Cell carcinoma of the upper urinary tract | (Nakanishi et al., 2007) |
| Lung | Non-small cell lung cancer | (Kaira et al., 2008b; Imai et al., 2009; Kaira et al., 2009c; Kaira et al., 2009d; Kaira et al., 2010b; Kaira et al., 2010a; Kyoichi, 2010; Takeuchi et al., 2010; Kaira et al., 2011b; Kaira et al., 2012a; Chuntao et al., 2015) |
| | Pulmonary adenocarcinoma | (Kaira et al., 2010b) |
| | Squamous cell carcinoma of the lung | (Kaira et al., 2009b) |
| | Lung cancer | (Kaira et al., 2007; Kaira et al., 2011a) |
| | Neuroendocrine tumors of the lung | (Kaira et al., 2008c; Kyoichi et al., 2008) |
| | Malignant pleural mesothelioma | (Kaira et al., 2011c) |
| Colon | Rectal cancer | (Ebara et al., 2010) |
| Breast | Breast Cancer | (Furuya et al., 2012; Erner et al., 2013; Fukumoto et al., 2013) |
| Pancreas | Pancreatic cancer | (Kaira et al., 2012b; Yanagisawa et al., 2012; Kaira et al., 2015a) |
| Gastrintestinal | Gastric carcinoma | (Ichinoe et al., 2011; Ichinoe et al., 2015) |
| | Oesophageal cancer | (Suzuki et al., 2014) |
| Blood | Multiple myeloma | (Isoda et al., 2014) |
| | Thymic carcinomas | (Kaira et al., 2009a) |
| Hepatobilbiar | Biliary tract cancer | (Kaira et al., 2014; Yanagisawa et al., 2014) |
| | Hepatocellular carcinoma | (Li et al., 2013; Masashi et al., 2014) |
| | Adenoid cystic carcinoma | (Kaira et al., 2013) |
| Metastatic | Primary metastatsis | (Kaira et al., 2008a) |
| | Liver Metastasis | (Kaoru et al., 2011) |
| Brain | Glioma | (Keyaerts et al., 2007; Stockhammer et al., 2008; Okubo et al., 2010) |
| | Astrocytic tumors | (Nawashiro et al., 2006) |
| Head & Neck | Oral squamous cell carcinoma | (Kim et al., 2004a; Nobusawa et al., 2013) |
| | Tongue cancer | (Toyoda et al., 2014a) |
| | Hypopharyngeal squamous cell carcinoma | (Toyoda et al., 2014b) |
| Prostate | Prostate cancer | (Sakata et al., 2009; Wang et al., 2011; Segawa et al., 2013; Yanagisawa et al., 2015) |
| Uterus | Endometrioid adenocarcinoma | (Watanabe et al., 2014) |

System ASC transport activity is ubiquitous and characterized by its preference for small neutral amino acids including alanine, serine, and cysteine. The system ASC of neutral amino acid transporters (SLC1A4 and SLC1A5) belongs to the solute carrier family-1 (SLC1), which also includes the high-affinity glutamate transporters. Human ATB0 was identified by RT-PCR and enzymatic restriction analysis in the human proximal tubule cell line HKPT and corresponds to rodent ASCT2. The two ASC transporters exhibit distinct substrate selectivity. SLC1A4 encodes the sodium-dependent amino acid transporter ASCT1, which accepts L-alanine, Lserine, L-theonine, and L-cysteine in a stereospecific manner. ASCT2, the second isoform of the ASC transport system, is encoded by SLC1A5. In the kidney and intestine, ASCT2 is present in the brush-border membranes of the proximal tubule cells and enterocytes, respectively. In addition to the typical system ASC substrates, it also accepts L-glutamine and L-asparagine at higher affinity as well as methionine, leucine, and glycine with lower affinity. Both ASCT1 and ASCT2 mediate the sodium-dependent obligatory exchange of substrate amino acids (Pinho et al., 2007b).

More recently, ASCT2 has been suggested as a marker of cancer prognosis in the types of cancer listed in the following table:

| | | |
|---|---|---|
| Breast | Breast Cancer | (Betsunoh et al., 2013; Kim et al., 2013) |
| Brain | Neuroblastoma | (Ren et al., 2015) |
| Colon | Rectal cancer | (Witte et al., 2002) |
| Gastrintestinal | Oesophageal cancer | (Honjo et al., 2016) |
| Head & Neck | Lacrimal gland adenocarcinoma | (Koo et al., 2015) |
| | Tongue cancer | (Toyoda et al., 2014a) |
| | Laryngeal squamous cell carcinoma | (Nikkuni et al., 2015) |
| | Thyroid medullary carcinoma | (Kim et al., 2016) |
| Hepatobilbiar | Hepatocellular carcinoma | (Ge et al., 2015) |
| Kidney | Renal cell carcinoma | (Liu et al., 2015) |
| Lung | Non-small cell lung cancer | (Shimizu et al., 2014) |
| Metastatic | Primary metastatsis | (Kim et al., 2014) |
| Pancreas | Pancreatic cancer | (Kaira et al., 2015a; Kaira et al., 2015b) |
| Skin | Melanoma | (Wang et al., 2014) |

ASCT2 is expressed in colorectal adenocarcinomas and patient survival decreased with increased percentage of ASCT2-positive cancer cells. These results indicate that ASCT2 is expressed in a significant number of colorectal adenocarcinomas, and that ASCT2 expression is associated with aggressive biological behavior (Witte et al., 2002). It has been proposed that ASCT2 appears to be required for the glutamine metabolism in both nonmalignant and malignant prostate. However, ASCT2-positive prostate adenocarcinoma seems to be related to a more aggressive biological behavior. ASCT 2 seems to be involved in tumor progression (Li et al., 2003; Wang et al., 2015). ASCT2 expression has a crucial role in the metastasis of pulmonary adecocarcinomas, and is a potential molecular marker for predicting poor prognosis after surgery (Shimizu et al., 2014). ASCT2 expression was also found to play an important role in tumour cell growth, and is a promising pathological marker for predicting a worse outcome in pancreatic cancer (Kaira et al., 2015b; Kyoichi et al., 2015). High ASCT2 expression was also found to be significantly associated with poor prognosis and survival of neuroblastoma patients (Ren et al., 2015). In addition, others have suggested that ASCT2 suppression exerts proapoptotic effects transcending those of glutamine starvation alone (Bryan et al., 2004; Fuchs et al., 2004). The importance of ASCT2 expression in melanoma was confirmed by shRNA knockdown, which inhibited glutamine uptake, mTORC1 signalling and cell proliferation (Wang et al., 2014).

The use of siRNA to inhibit ASCT2 gene expression have been disclose by several groups (Wieland et al., 2005; Nicklin et al., 2009; Okudaira et al., 2011; Barel et al., 2012; Hassanein et al., 2013; Hassanein et al., 2015; Corbet et al., 2016; Straka et al., 2016; Zhou et al., 2016; Lee et al., 2017).

RNA interference ("RNAi") is a recently discovered mechanism of post-transcriptional gene silencing in which double-stranded RNA corresponding to a gene (or coding region) of interest is introduced into an organism, resulting in degradation of the corresponding mRNA. The phenomenon was originally discovered in *Caenorhabditis elegans* (Fire et al., 1998).

Unlike antisense technology, the RNAi phenomenon persists for multiple cell divisions before gene expression is regained. The process occurs in at least two steps: an endogenous ribonuclease cleaves the longer dsRNA into shorter, 21- 22- or 23-nucleotide-long RNAs, termed "small interfering RNAs" or siRNAs (Hannon, 2002). The siRNA segments then mediate the degradation of the target m RNA. RNAi has been used for gene function determination in a manner similar to but more efficient than antisense oligonucleotides. By making targeted knockouts at the RNA level by RNAi, rather than at the DNA level using conventional gene knockout technology, a vast number of genes can be assayed quickly and efficiently. RNAi is therefore an extremely powerful, simple method for assaying gene function.

RNAi has been shown to be effective in cultured mammalian cells. In most methods described to date, RNAi is carried out by introducing double-stranded RNA into cells by microinjection or by soaking cultured cells in a solution of double-stranded RNA, as well as transfecting the cells with a plasmid carrying a hairpin-structured siRNA expressing cassette under the control of suitable promoters, such as the U6, H1 or cytomegalovirus ("CMV") promoter (Elbashir et al., 2001; Harborth et al., 2001; Lee et al., 2001; Brummelkamp et al., 2002; Miyagishi et al., 2002; Paddison et al., 2002; Paul et al., 2002; Sui et al., 2002; Xia et al., 2002; Yu et al., 2002). The gene-specific inhibition of gene expression by double-stranded ribonucleic acid is generally described in U.S. Pat. No. 6,506,559, which is incorporated herein by reference. Exemplary use of siRNA technology is further described in Published U.S. Patent Application No. 2003/01090635 and Published U.S. Patent Application NO. 20040248174, which are incorporated herein by reference. Davis (Davis, 2009) describes the targeted delivery of siRNA to humans using nanoparticle technology.

SUMMARY OF THE INVENTION

An object of the present invention is to use an RNA interference technique to down regulate the expression of the LAT1 and/or ASCT2 genes in order to treat or prevent cancer. Preferred cancers that can be treated or prevented by the present invention include bladder, brain, colon, head and neck, kidney, liver, lung, lymph node, mammary gland, muscle, ovary, pancreas, skin and stomach cancers. The compositions (or molecules) of the invention comprises or consists of short interfering nucleic acid molecules (siNA) and related compounds including, but not limited to, siRNA. The present invention encompasses compositions and methods of use of siNA including, but not limited to short interfering RNA (siRNA), double-stranded RNA (dsRNA), micro-RNA (miRNA), antagomirs and short hairpin RNA (shRNA) capable of mediating RNA interference. In one embodiment, the siNA molecule of the invention can be incorporated into RISC (RNA-induced silencing complex).

A further object of the present invention is to provide a siRNA molecule that efficiently down regulates the expression of the LAT1 gene and/or ASCT2 gene.

Accordingly, in a first aspect, the invention relates to a siNA molecule, wherein said molecule specifically targets at least one sequence selected from SEQ ID NO: 1-SEQ ID NO: 104 or a variant thereof and SEQ ID NO: 209-SEQ ID NO: 297 or a variant thereof. In an alternative embodiment, the invention relates to an siNA molecule wherein said molecule specifically targets at least one sequence complementary to at least one sequence selected from SEQ ID NO: 1-SEQ ID NO: 104 or a variant thereof and SEQ ID NO: 209-SEQ ID NO: 297 or a variant thereof. In one embodiment, the invention relates to an isolated siNA molecule, preferably an isolated siRNA molecule.

In one embodiment, the siNA molecule reduces expression of the (preferably, human) LAT 1 and/or ASCT2 gene when introduced into a cell.

In one embodiment, the siNA molecule specifically targets at least one sequence selected from SEQ ID No 4, 6, 10, 13, 22, 34, 58, 61, 81, 83, 87 and 95 to 104 or a variant thereof. Preferably, the siNA molecule targets a sequence selected from SEQ ID NO 6, 22, 34, 58 and 61 or a variant thereof. Even more preferably, the siNA targets SEQ ID NO: 61 or 58 to a variant thereof. Preferably, the siNA molecule reduces expression of the LAT1 gene when expressed into a cell.

In an alternative embodiment, the siNA molecule specifically targets at least one sequence selected from SEQ ID NO: 209, 216, 225, 226, 228, 235 to 238, 245, 260, 264, 267, 271, 272, 278, 279 and 281 to 297. Preferably, the siNA molecule targets a sequence selected from SEQ ID NO 225, 237, 267 or 278 or a variant thereof. Even more preferably, the siNA targets SEQ ID NO: 267 or 278 or a variant thereof. Preferably the siNA molecule reduces expression of the ASCT2 gene when expressed into a cell.

In a further embodiment, the siNA preferably comprises a double-stranded RNA molecule, whose antisense strand is substantially complementary to any of SEQ ID NO: 1-SEQ ID NO: 104, more preferably SEQ ID No 4, 6, 10, 13, 22, 34, 58, 61, 81, 83, 87 and 95 to 104, even more preferably SEQ ID NO 6, 22, 34, 58 and 61, and most preferably SEQ ID NO: 61 or 58 or any variant thereof, and its sense strand will comprise an RNA sequence complementary to the sense strand, wherein both strands are hybridised by standard base pairing between nucleotides. In a further embodiment, said sense stand comprises or consists of a sequence selected from SEQ ID NO: 105 to 208, preferably SEQ ID NO: 108, 110, 114, 117, 126, 138, 162, 165, 185, 187, 191 and 199 to 208, more preferably SEQ ID NO: 110, 126, 138, 162 and 165 and most preferably SEQ ID NO: 162 or 165 or a variant thereof. The corresponding antisense strands are described in FIGS. 26A-D. Preferably, the siNA molecule reduces expression of the LAT1 gene when expressed into a cell.

In an alternative embodiment, the siNA preferably comprises a double-stranded RNA molecule, whose antisense strand is substantially complementary to any of SEQ ID NO: 209-SEQ ID NO: 297, more preferably SEQ ID NO: 209, 216, 225, 226, 228, 235 to 238, 245, 260, 264, 267, 271, 272, 278, 279 and 281 to 297, even more preferably SEQ ID NO 225, 237, 267 or 278 and most preferably SEQ ID NO: 267 or 278 or any variant thereof, and its sense strand will comprise an RNA sequence complementary to the sense strand, wherein both strands are hybridised by standard base pairing between nucleotides. In a further embodiment, said sense stand comprises or consists of a sequence selected from SEQ ID NO: 298 to 386, preferably, SEQ ID NO: 298, 305, 314, 315, 317, 324-327, 334, 349, 353, 356, 360, 361, 367, 368 and 370 to 386, more preferably SEQ ID NO: 314, 326, 36 and 367 or a variant thereof, and even more preferably SEQ ID NO: 356 or 367 or any variant thereof. The corresponding antisense strands are described in FIG. 27. Preferably, the siNA molecule reduces expression of the ASCT2 gene when expressed into a cell.

Within the meaning of the present invention "substantially complementary" to a target mRNA sequence, may also be understood as "substantially identical" to said target sequence. "Identity" as is known by one of ordinary skill in the art, is the degree of sequence relatedness between nucleotide sequences as determined by matching the order and identity of nucleotides between sequences. In one embodiment the antisense strand of an siRNA having 80%, and between 80% up to 100% complementarity, for example, 85%, 86%, 87%, 88%, 89%, 90%, 91%, 92%, 93%, 94%, 95%, 96%, 97% or 99% complementarity, to the target mRNA sequence are considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule.

A gene is "targeted" by a siNA according to the present invention when, for example, the siNA molecule selectively decreases or inhibits the expression of the gene. The phrase "selectively decrease or inhibit" as used herein encompasses siNAs that affect expression of LAT1 and/or ASCT2. Alternatively, a siNA targets a gene when the siNA hybridizes under stringent conditions to the gene transcript, i.e. its mRNA. Capable of hybridizing "under stringent conditions" means annealing to the target mRNA region, under standard conditions, e.g., high temperature and/or low salt content which tend to disfavor hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387-389.

Nucleic acid sequences cited herein are written in a 5' to 3' direction unless indicated otherwise. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases these bases may appear as "dT" to differentiate deoxyribonucleotides present in a chain of ribonucleotides.

In one embodiment of the invention, the siNA molecule is 40 base pairs or fewer in length. Preferably, the siNA molecule is 19 to 25 base pairs in length. In one embodiment, the siNA comprises or consists of a 21 nucleotide double-stranded region. Preferably, the siNA has a sense and an anti-sense strand. In an alternative embodiment, the siNA molecule comprises or consists of a 19 nucleotide double-stranded region. In one embodiment, the siNA has blunt ends. In an alternative embodiment, the siNA has 5' and/or 3' overhangs. Preferably the overhangs are between 1 to 5 nucleotides, more preferably, 2 nucleotide overhangs. The overhangs may be ribonucleic acids, or deoxyribonucleic acids.

In one embodiment, the siNA molecule according to the invention comprises a chemical modification. Preferably, the chemical modification is on the sense strand, the antisense strand or both. Examples of chemical modifications include phosphorothioate internucleotide linkages, 2'-OMethylation, 2'-deoxy-fluoro ribonucleotides, 2'-deoxy ribonucleotides, 5-C methyl nucleotides, inverted deoxybasic residue incorporation or a substitution of uracyl ribose nucleotides with deoxythymidine nucleotides or combinations thereof.

In one embodiment, the 5' or 3' overhangs are dinucleotides, preferably thymidine dinucleotide. In a preferred embodiment, the 5' or 3' overhangs are deoxythymidines. In one embodiment, the sense strand comprises at least one, preferably two 3' overhangs. Preferably, said sense strand comprises at least one, preferably two 3' deoxythymidines. In an alternative embodiment, the antisense strand comprises at least one, preferably two 3' overhangs. Preferably, said sense strand comprises at least one, preferably two 3' deoxythymidines. In a further preferred embodiment, both the sense and antisense strands comprise 3' overhangs as described herein.

In a further embodiment, the siNA molecule preferably comprises a double-stranded RNA molecule, wherein preferably the sense strand and the anti-sense strand are selected from the below or a variant thereof.

| Sense strand | Anti-sense strand | |
|---|---|---|
| 387 | 388. | This sequence is also referred to herein as SEQ ID NO: 58/387/388. |
| 389 | 390 | This sequence is also referred to herein as SEQ ID NO: 58/389/390 |
| 389 | 412 | This sequence is also referred to herein as SEQ ID NO: 58/389/412 |
| 391 | 392 | This sequence is also referred to herein as SEQ ID NO: 61/391/392 |
| 393 | 394 | This sequence is also referred to herein as SEQ ID NO: 61/393/394 |
| 395 | 396 | This sequence is also referred to herein as SEQ ID NO: 61/395/396 |
| 397 | 398 | This sequence is also referred to herein as SEQ ID NO: 267/397/398 |
| 399 | 400 | This sequence is also referred to herein as SEQ ID NO: 267/399/400 |
| 401 | 402 | This sequence is also referred to herein as SEQ ID NO: 267/401/402 |
| 403 | 404 | This sequence is also referred to herein as SEQ ID NO: 278/403/404 |
| 405 | 406 | This sequence is also referred to herein as SEQ ID NO: 278/405/406 |
| 407 | 408 | This sequence is also referred to herein as SEQ ID NO: 278/407/408 |

By "variant" as used herein is meant a sequence with 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the non-variant nucleic or ribonucleic acid sequence.

By "down-regulating" is meant a decrease in the expression of LAT1 and/or ASCT2 by up to or more than 10%, 15% 20%, 25%, 30%, 35%, 40%, 45% 50%, 55% 60%, 65%, 70%, 75%, 80%, 85%, 90%, 95% when compared to the level in a control. Alternatively, the siNA molecule described herein may abolish LAT1 and/or ASCT2 expression. The term "abolish" means that no expression of LAT1 and/or ASCT2 is detectable or that no functional LAT1 and/or ASCT2 protein is produced. For example, a reduction in the expression and/or protein levels of at least LAT1 and/or ASCT2 expression may be a measure of protein and/or nucleic acid levels and can be measured by any technique known to the skilled person, such as, but not limited to, any form of gel electrophoresis or chromatography (e.g. HPLC).

Notably, in some embodiments, the siNA molecule (either the 5' or 3' strand or both) may begin with at least one, preferably two alanine nucleotides. Alternatively, if the target sequence starts with one or two alanine sequences, these may not be included (targeted) in the siNA molecule.

In one embodiment, the target sequence may be characterised by at least one, preferably two alanine nucleotides at the 3' end of the sequence, and/or the target sequence lacks at least one, preferably two alanine nucleotides at the 5' end of the sequence, and/or the target sequence lacks two consecutive alanine nucleotides within the sequence. In a preferred embodiment, the siNA molecules of the invention are characterised in that they target sequences with the above properties.

In one embodiment a plurality of species of siNA molecule are used, wherein said plurality of siNA molecules are targeted to the same or a different mRNA species.

In one embodiment, the siNA is selected from dsRNA, siRNA or shRNA. Preferably, the siNA is siRNA.

In a further embodiment, the invention relates to a siNA molecule, as herein described for use as a medicament. In one embodiment, the invention relates to a siNA for use in the treatment of a disorder characterised by increased expression levels (compared to the levels in a healthy subject) of LAT1 and/or ASCT2.

In another aspect of the invention, there is provided a siNA molecule, as described herein for use in the treatment of cancer.

In a further aspect, the invention relates to the use of at least one siNA molecule, as described herein in the preparation of a medicament for the treatment of cancer.

In another aspect, the invention relates to a method for the treatment of cancer, the method comprising administering at least one siNA molecule, as described herein, to a patient or subject in need thereof.

In one embodiment, the cancer is selected from bladder, blood, brain, colon, head and neck, kidney, liver, lung, lymph node, mammary gland, muscle, ovary, pancreas, prostate, skin, stomach and uterus cancer.

In another aspect of the invention there is provided a pharmaceutical composition comprising at least one siNA molecule as described herein and a pharmaceutically acceptable carrier.

In a further aspect of the invention there is provided a method, preferably an in vitro method of inhibiting amino acid uptake into a cell, the method comprising administering a siNA as defined herein to a cell. Preferably, the amino acid uptake is sodium-independent leucine uptake. Alternatively, the amino acid uptake is sodium-dependent alanine uptake. In one embodiment, amino acid uptake is inhibited by up to or more than 10%, 20%, 30%, 40%, 50%, 60%, 70%, 80% or 90% when compared to the level in a control.

In a further aspect of the invention, there is provided a method of decreasing cell proliferation, the method comprising administering at least on siNA as described herein to a cell. In one embodiment, said decrease in cell proliferation may be up to or more than 10%, 20%, 30%, 40%, 50%, 60%, 70%, 80% or 90% when compared to the level in a control.

In a yet further aspect of the invention, there is provided a method of reducing tumour volume, preferably in a patient, the method comprising administering at least one siNA as described herein. In one embodiment, said decrease in tumour volume may be up to or more than 10%, 20%, 30%, 40%, 50%, 60%, 70%, 80% or 90% when compared to the level in a control.

In on embodiment, of the above-described methods at least one LAT-1 siNA or at least one ASCT2 siNA is administered. In an alternative embodiment, at least one LAT-1 siNA and at least one ASCT2 siNA is administered In another embodiment, the invention relates to methods of reducing cancer cell proliferation comprising treating the cells with an siNA of the invention in combination with one or more anti-cancer agents known in the art, preferably wherein the anti-cancer agent comprises an anti-antineoplastic agent, more preferably a cytotoxic antineoplastic agent and most preferably 5-fluoruracil (5-FU), cisplatin (Cisp) and/or oxaliplatin (Oxa).

The invention also relates to methods of treating cancer comprising administrating an siNA of the invention in combination with one or more anti-cancer agents known in the art, preferably to a patient in need thereof, preferably wherein the anti-cancer agent comprises an anti-antineoplastic agent, more preferably a cytotoxic antineoplastic agent and most preferably 5-fluoruracil (5-FU), cisplatin (Cisp) and/or oxaliplatin (Oxa). The invention further relates to pharmaceutical compositions comprising the siNA of the invention and the one or more anti-cancer agent.

In another embodiment the invention relates to methods for increasing the efficacy of an anti-cancer therapy given to a patient comprising administering an siNA of the invention in combination with the therapy. Said increase in efficacy may be up to or more than 10%, 20%, 30%, 40%, 50%, 60%, 70%, 80% or 90% when compared to the efficacy of either administration of siNA or the anti-cancer agent alone.

In a preferred embodiment, said siNA targets SEQ ID NO: 58 or SEQ ID NO: 61 (for example, the siNA comprises a sense strand comprising a sequence selected from SEQ ID NO: 162 or 165 respectively) or a variant thereof. In a further alternative embodiment, said siNA comprises a sense strand, wherein the sequence of the sense strand is SEQ ID NO 387 or a variant thereof, and an antisense strand, wherein the sequence of the antisense strand is SEQ ID NO: 388 or a variant thereof. Alternatively, said siNA comprises a sense strand, wherein the sequence of the sense strand is SEQ ID NO 393 or a variant thereof, and an antisense strand, wherein the sequence of the antisense strand is SEQ ID NO: 394 or a variant thereof.

In an alternative embodiment, said siNA targets SEQ ID NO: 267 or 278 or a variant thereof (for example, the siNA comprises a sense strand comprising a sequence selected from SEQ ID NO: 356 or 367). In a further alternative embodiment, said siNA comprises a sense strand, wherein the sequence of the sense strand is SEQ ID NO 399 or a variant thereof, and an antisense strand, wherein the sequence of the antisense strand is SEQ ID NO: 400 or a variant thereof. Alternatively, said siNA comprises a sense strand, wherein the sequence of the sense strand is SEQ ID NO 405 or a variant thereof, and an antisense strand, wherein the sequence of the antisense strand is SEQ ID NO: 406 or a variant thereof.

In one embodiment, the anti-cancer agent is administered prior to, concurrently, or after administration of the siNA.

By "control" is meant herein either a cell or a patient administered no siNA or a cell administered a vehicle, as described herein.

DETAILED DESCRIPTION OF THE INVENTION

The present invention is directed to a method of targeting the LAT1 gene and/or ASCT2 gene by knocking down or inhibiting its expression as a novel strategy for cancer therapy. In particular, and according to a first aspect of the present invention, there is provided the use of a siRNA for inhibiting LAT1 gene and/or ASCT2 gene expression in the manufacture of a medicament for treating or preventing cancer, wherein the siRNA comprises a sense LAT1 or ASCT2 nucleic acid and an antisense LAT1 or ASCT2 nucleic acid. The present invention also provides the use of a vector encoding the siRNA for inhibiting LAT1 and ASCT2 gene expression in the manufacture of a medicament for treating or preventing cancer.

According to a second aspect of the present invention, there is provided a method of treating or preventing cancer comprising administering to an individual an effective amount of a siRNA that inhibits LAT1 and/or ASCT2 gene expression, wherein the siRNA comprises a sense LAT1 or ASCT2 nucleic acid and an antisense LAT1 or ASCT2 nucleic acid. The present invention also provides a method of treating or preventing cancer comprising administering to an individual an effective amount of a vector encoding the siRNA that inhibits LAT1 and ASCT2 gene expression.

Overexpression of the LAT1 transporter, an isoform of system L $Na^+$-independent neutral amino acid transporter, is a highly prevalent observation in various forms of cancer. The present invention is based on the surprising discovery that small interfering RNAs (siRNAs) selective for LAT1 are effective for treating cancer. In particular, bladder, blood, brain, colon, head and neck, kidney, liver, lung, lymph node, mammary gland, metastatic, muscle, ovary, pancreas, prostate, skin, stomach and uterus cancer.

The siRNA or vector encoding the siRNA, or the medicament comprising the siRNA or vector encoding the siRNA, may be administered to an individual by enteral administration (e.g., oral, rectal and intranasal), parenteral administration (e.g., intravascular administration, peri- and intra-tissue administration, subcutaneous injection or deposition, subcutaneous infusion intraocular administration and direct administration at or near the site of a tumour).

According to a third aspect of the present invention there is provided an in vitro method of inhibiting the expression of the LAT1 gene and/or ASCT2 gene in a cell comprising contacting the cell with siNA that inhibits LAT1 and/or ASCT2 gene expression as described herein. In one embodiment, said siRNA comprises a sense LAT1 and/or ASCT2 nucleic acid and an anti-sense LAT1 and/or ASCT2 nucleic acid, wherein the sense LAT1 or ASCT2 nucleic acid is substantially identical to a target sequence contained within LAT1 or AST2 mRNA and the anti-sense LAT1 or ASCT2 nucleic acid is complementary to the sense LAT1 or ASCT2 nucleic acid. The present invention also provides an in vitro method of inhibiting the expression of the LAT1 and/or ASCT2 genes in a cell comprising contacting the cell with a vector encoding a siRNA that inhibits LAT1 and/or ASCT2 gene expression, said siRNA comprises a sense LAT1 and/or ASCT2 nucleic acid and an anti-sense LAT1 and/or ASCT2 nucleic acid, wherein the sense LAT1 or ASCT2 nucleic acid is substantially identical to a target sequence contained within LAT1 or ASCT2 mRNA and the anti-sense LAT1 or ASCT2 nucleic acid is complementary to the sense LAT1 or ASCT2 nucleic acid.

Expression of the gene may be inhibited by introduction of a double stranded ribonucleic acid (dsRNA) molecule into the cell in an amount sufficient to inhibit expression of the LAT1 and/or ASCT2 genes.

The siRNAs used in the invention are believed to cause the RNAi-mediated degradation of LAT1 or ASCT2 mRNA so that the protein product of the LAT1 or ASCT2 gene is not produced or is produced in reduced amounts. The siRNAs used in the invention can be used to alter gene expression in a cell in which expression of LAT1 and/or ASCT2 is upregulated, e.g., as a result of malignant transformation of the cells. Binding of the siRNA to a LAT1 or ASCT mRNA transcript in a cell results in a reduction in LAT1 and ASCT2 production by the cell.

The term "siRNA" is used to mean a double stranded RNA molecule which prevents translation of a target mRNA. Standard techniques of introducing siRNA into the cell are used, including those in which DNA is a template from which RNA is transcribed. The siRNA that inhibits LAT1 or ASCT2 gene expression includes a sense LAT1 or ASCT2 nucleic acid sequence and an antisense LAT1 or ASCT2 nucleic acid sequence. The siRNA may be constructed such that a single transcript has both the sense and complementary antisense sequences from the target gene, e.g., in the form of a hairpin.

The siRNA preferably comprises short double-stranded RNA that is targeted to the target mRNA, i.e., LAT1 mRNA or ASCT2 mRNA. The siRNA comprises a sense RNA strand and a complementary antisense RNA strand annealed together by standard Watson-Crick base-pairing interactions (hereinafter "base-paired"). The sense strand comprises a nucleic acid sequence which is substantially identical to a target sequence contained within the LAT1 mRNA or ASCT2 mRNA.

The terms "sense/antisense sequences" and "sense/antisense strands" are used interchangeable herein to refer to the parts of the siRNA of the present invention that are substantially identical (sense) to the target LAT1 and ASCT2 mRNA sequence or substantially complementary (antisense) to the target LAT1 and ASCT2 mRNA sequence.

As used herein, a nucleic acid sequence "substantially identical" to a target sequence contained within the target mRNA is a nucleic acid sequence which is identical to the target sequence, or which differs from the target sequence by one or more nucleotides. Preferably, the substantially identical sequence is identical to the target sequence or differs from the target sequence by one, two or three nucleotides, more preferably by one or two nucleotides and most preferably by only 1 nucleotide. Sense strands which comprise nucleic acid sequences substantially identical to a target sequence are characterized in that siRNA comprising such a sense strand induces RNAi-mediated degradation of mRNA containing the target sequence. For example, an siRNA of the invention can comprise a sense strand comprising a nucleic acid sequence which differs from a target sequence by one, two, three or more nucleotides, as long as RNAi-mediated degradation of the target mRNA is induced by the siRNA.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. The siRNA can also contain alterations, substitutions or modifications of one or more ribonucleotide bases. For example, the present siRNA can be altered, substituted or modified to contain one or more, preferably 0, 1, 2 or 3, deoxyribonucleotide bases. Preferably, the siRNA does not contain any deoxyribonucleotide bases.

The siRNA can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more, preferably 0, 1, 2 or 3, nucleotides in the siRNA with deoxyribonucleotides.

Degradation can be delayed or avoided by a wide variety of chemical modifications that include alterations in the nucleobases, sugars and the phosphate ester backbone of the siRNAs. All of these chemically modified siRNAs are still able to induce siRNA-mediated gene silencing provided that the modifications were absent in specific regions of the siRNA and included to a limited extent. In general, backbone modifications cause a small loss in binding affinity, but offer nuclease resistance. Phosphorothioate (PS)- or boranophosphate (BS)-modified siRNAs have substantial nuclease resistance. Silencing by siRNA duplexes is also compatible with some types of 2'-sugar modifications: 2'-H, 2'-O-methyl, 2'-O-methoxyethyl, 2'-fluoro (2'-F), locked nucleic acid (LNA) and ethylene-bridge nucleic acid (ENA). Suitable chemical modifications are well known to those skilled in the art.

The siRNA used in the present invention is a double-stranded molecule comprising a sense strand and an antisense strand, wherein the sense strand comprises or consists of a ribonucleotide sequence corresponding to a LAT1 or ASCT2 target sequence, and wherein the antisense strand comprises a ribonucleotide sequence which is complementary to said sense strand, wherein said sense strand and said antisense strand hybridize to each other to form said double-stranded molecule, and wherein said double-stranded molecule, when introduced into a cell expressing the LAT1 and ASCT2 genes, inhibits expression of said genes. As indicated further below, said LAT1 target sequence preferably comprises at least about 10 contiguous, more preferably 15 to 21, and most preferably about 19 to 21 contiguous nucleotides selected from the group consisting of from SEQ ID NOS 4, 6, 10, 13, 22, 34, 58, 61, 81, 83, 87, and 95 to 104. As indicated further below, said ASCT2 target sequence preferably comprises at least about 10 contiguous, more preferably 15 to 21, and most preferably about 19 to 21 contiguous nucleotides selected from the group consisting of from SEQ ID NOS 209, 216, 225, 226, 228, 235-238, 245, 260, 264, 267, 271, 272, 278, 279, 281 to 297.

In one embodiment of the present invention, said sense strand and antisense strand of the siRNA molecule are covalently connected via a linker molecule. Said linker molecule may be a polynucleotide linker or a non-nucleotide linker. Preferably the linker is a loop sequence. The loop sequence is preferably 3 to 23 nucleotide in length. Suitable loop sequences are described at www.ambion.com/techlib/tb/tb_506.html and (Jacque et al., 2002). Preferred loop sequences include:

AUG: (Sui et al., 2002).
CCC, CCACC or CCACACC: (Paul et al., 2002).
UUCG: (Lee et al., 2002).
CTCGAG or AAGCUU: (Biology, 2003).
UUCAAGAGA: (Yu et al., 2002).

The loop sequence can be selected from group consisting of AUG, CCC, UUCG, CCACC, CTCGAG, AAGCUU, CCACACC, and UUCAAGAGA. Preferably the loop sequence is UUCAAGAGA ("ttcaagaga" in DNA).

The siRNA used in the present invention can be obtained using a number of techniques known to those of skill in the art. For example, the siRNA can be chemically synthesized or recombinantly produced using methods known in the art, such as the *Drosophila* in vitro system described in U.S. published application 2002/0086356, the entire disclosure of which is herein incorporated by reference. The siRNA may be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Biospring (Frankfurt, Germany), Proligo (Hamburg, Germany), Dharmacon Research (Lafayette, Colo., USA), Thermo Fisher Scientific (Waltham, Mass. USA), Glen Research (Sterling, Va., USA), ChemGenes (Ashland, Mass., USA) and Sigma-Aldrich (St. Louis, Mo. USA).

The siRNA can also be expressed from recombinant circular or linear DNA vectors using any suitable promoter. Suitable promoters for expressing siRNA from a vector include, for example, the U6 or H1 RNA pol III promoter sequences and the cytomegalovirus promoter. Selection of other suitable promoters is within the skill in the art. The vector can also comprise inducible or regulatable promoters for expression of the siRNA in a particular tissue or in a particular intracellular environment.

The siRNA expressed from a vector can either be isolated from cultured cell expression systems by standard techniques, or can be expressed intracellularly. The vector can be used to deliver the siRNA to cells in vivo, e.g., by intracellularly expressing the siRNA in vivo. siRNA can be expressed from a vector either as two separate, complementary RNA molecules, or as a single RNA molecule with two complementary regions. Selection of vectors suitable for expressing the siRNA, methods for inserting nucleic acid sequences for expressing the siRNA into the vector, and methods of delivering the vector to the cells of interest are well known to those skilled in the art.

The siRNA can also be expressed from a vector intracellularly in vivo. As used herein, the term "vector" means any nucleic acid- and/or viral-based technique used to deliver a desired nucleic acid. Any vector capable of accepting the coding sequences for the siRNA molecule(s) to be expressed can be used, including plasmids, cosmids, naked DNA, optionally condensed with a condensing agent, and viral vectors. Suitable viral vectors include vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate. When the vector is a lentiviral vector it is preferably pseudotyped with surface proteins from vesicular stomatitis virus, rabies virus, Ebola virus or Mokola virus.

Vectors are produced for example by cloning a LAT1 or ASCT2 target sequence into an expression vector so that operatively-linked regulatory sequences flank the LAT1 or ASCT2 sequence in a manner that allows for expression (by transcription of the DNA molecule) of both strands (Lee et al., 2002). An RNA molecule that is antisense to LAT1 mRNA or ASCT2 mRNA is transcribed by a first promoter (e.g., a promoter sequence 3' of the cloned DNA) and an RNA molecule that is the sense strand for the LAT1 mRNA or the ASCT2 mRNA is transcribed by a second promoter (e.g., a promoter sequence 5' of the cloned DNA). The sense and antisense strands hybridize in vivo to generate siRNA constructs for silencing of the LAT1 gene or ASCT2 gene. Alternatively, two vectors are utilized to create the sense and anti-sense strands of a siRNA construct. Cloned LAT1 or ASCT2 can encode a construct having secondary structure, e.g., hairpins, wherein a single transcript has both the sense and complementary antisense sequences from the target gene. Such a transcript encoding a construct having secondary structure, will preferably comprises a single-stranded ribonucleotide sequence (loop sequence) linking said sense strand and said antisense strand.

The siRNA is preferably isolated. As used herein, "isolated" means synthetic, or altered or removed from the natural state through human intervention. For example, a siRNA naturally present in a living animal is not "isolated," but a synthetic siRNA, or a siRNA partially or completely separated from the coexisting materials of its natural state is "isolated." An isolated siRNA can exist in substantially purified form, or can exist in a non-native environment such as, for example, a cell into which the siRNA has been delivered. By way of example, siRNA which are produced inside a cell by natural processes, but which are produced from an "isolated" precursor molecule, are themselves "isolated" molecules. Thus, an isolated dsRNA can be introduced into a target cell, where it is processed by the Dicer protein (or its equivalent) into isolated siRNA.

As used herein, "inhibit" means that the activity of the LAT1 or ASCT2 gene expression product or level of the LAT1 or ASCT2 gene expression product is reduced below that observed in the absence of the siRNA molecule of the invention. The inhibition with a siRNA molecule preferably is significantly below that level observed in the presence of an inactive or attenuated molecule that is unable to mediate an RNAi response. Inhibition of gene expression with the siRNA molecule is preferably significantly greater in the presence of the siRNA molecule than in its absence. Preferably, the siRNA inhibits the level of LAT1 or ASCT2 gene expression by at least 10%, more preferably at least 50% and most preferably at least 75%.

Preferably the siRNA molecule inhibits LAT1 or ASCT2 gene expression so that growth of the cell containing the LAT1 or ASCT2 gene is inhibited. By inhibiting cell growth is meant that the treated cell proliferates at a lower rate or has decreased viability than an untreated cell. Cell growth is measured by proliferation assays known in the art.

As used herein, an "isolated nucleic acid" is a nucleic acid removed from its original environment (e.g., the natural environment if naturally occurring) and thus, synthetically altered from its natural state. In the present invention, isolated nucleic acid includes DNA, RNA, and derivatives thereof. When the isolated nucleic acid is RNA or derivatives thereof, base "t" should be replaced with "u" in the nucleotide sequences.

As used herein, the term "complementary" refers to Watson-Crick or Hoogsteen base pairing between nucleotides units of a polynucleotide, and the term "binding"

means the physical or chemical interaction between two polypeptides or compounds or associated polypeptides or compounds or combinations thereof.

As used herein, the phrase "highly conserved sequence region" means a nucleotide sequence of one or more regions in a target gene does not vary significantly from one generation to the other or from one biological system to the other.

As used herein, the term "complementarity" or "complementary" means that a nucleic acid can form hydrogen bond(s) with another nucleic acid sequence by either traditional Watson-Crick or other non-traditional types of interaction. In reference to the present invention, the binding free energy for a siRNA molecule with its complementary sequence is sufficient to allow the relevant function of the nucleic acid to proceed, e.g., RNAi activity. For example, the degree of complementarity between the sense and antisense strand of the siRNA molecule can be the same or different from the degree of complementarity between the antisense strand of the siRNA and the target RNA sequence.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. Preferably the term "complementarity" or "complementary" means that at least 90%, more preferably at least 95% and most preferably 100% of residues in a first nucleic acid sense can form hydrogen binds with a second nucleic acid sequence.

Complementary nucleic acid sequences hybridize under appropriate conditions to form stable duplexes containing few (one or two) or no mismatches. Furthermore, the sense strand and antisense strand of the siRNA can form a double stranded nucleotide or hairpin loop structure by the hybridization. In a preferred embodiment, such duplexes contain no more than 1 mismatch for every 10 matches. In an especially preferred embodiment, the sense and antisense strands of the duplex are fully complementary, i.e., the duplexes contain no mismatches.

As used herein, the term "cell" is defined using its usual biological sense. The cell can be present in an organism, e.g., mammals such as humans, cows, sheep, apes, monkeys, swine, dogs, and cats. The cell can be eukaryotic (e.g., a mammalian cell). The cell can be of somatic or germ line origin, totipotent or pluripotent, dividing or non-dividing. The cell can also be derived from or can comprise a gamete or embryo, a stem cell, or a fully differentiated cell. Preferably the cell is a bladder, brain, colon, head and neck, kidney, liver, lung, lymph node, mammary gland, muscle, ovary, pancreas, skin or stomach cancer cell.

As used herein, the term "RNA" means a molecule comprising at least one ribonucleotide residue. By "ribonucleotide" is meant a nucleotide with a hydroxyl group at the 2' position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogues of naturally-occurring RNA. Preferably the term "RNA" consists of ribonucleotide residues only.

As used herein, the term "organism" refers to any living entity comprised of at least one cell. A living organism can be as simple as, for example, a single eukaryotic cell or as complex as a mammal, including a human being.

As used herein, the term "subject" means an organism, which is a donor or recipient of explanted cells or the cells themselves. "Subject" also refers to an organism to which the nucleic acid molecules of the invention can be administered. The subject is preferably a mammal, e.g., a human, non-human primate, mouse, rat, dog, cat, horse, or cow. Most preferably the subject is a human.

As used herein, the term "biological sample" refers to any sample containing polynucleotides. The sample may be a tissue or cell sample, or a body fluid containing polynucleotides (e.g., blood, mucus, lymphatic fluid, synovial fluid, cerebrospinal fluid, saliva, amniotic fluid, amniotic cord blood, urine, vaginal fluid and semen). The sample may be a homogenate, lysate, extract, cell culture or tissue culture prepared from a whole organism or a subset of its cells, tissues or component parts, or a fraction or portion thereof. Lastly, the sample may be a medium, such as a nutrient broth or gel in which an organism, or cells of an organism, have been propagated, wherein the sample contains polynucleotides.

The invention relates to methods of inhibiting LAT1 and/or ACST2 gene expression which causes the inhibition of cancer cell growth. In particular, the invention provides a method for inhibiting the growth of a cancerous cell population comprising applying the LAT1 and/or ASCT2 siRNA to said cancerous cell population. Cancer cell growth is inhibited by contacting a cell with a composition of a LAT1 and/or ASCT2 siRNA. LAT1 and ASCT2 are amino acid transporter proteins that are overexpressed in tumors such as bladder, brain, colon, head and neck, kidney, liver, lung, lymph node, mammary gland, muscle, ovary, pancreas, skin and stomach cancer. Growth of the cell expressing LAT1 or ASCT2 can be inhibited by a LAT1 or ASCT2 siRNA. The cell may be further contacted with a transfection-enhancing agent to enhance delivery of the siRNA or siRNA encoding vector to the cell. Depending on the specific method of the present invention, the cell may be provided in vitro, in vivo or ex vivo.

Sequence information regarding the human LAT1 gene (GenBank accession NM_003486) was extracted from the NCBI Entrez nucleotide database. Up to 104 mRNA segments were identified. Sequence information regarding the human ASCT2 gene (GenBank accession NM_001145144) was extracted from the NCBI Entrez nucleotide database. Up to 89 mRNA segments were identified. Methods for designing double stranded RNA having the ability to inhibit gene expression in a target cell are known. See for example, U.S. Pat. No. 6,506,559, and Elbashir et al., 2001, herein incorporated by reference in its entirety.

Selection of siRNA target sites can be performed as follows
1. Beginning with the ATG start codon of the transcript, scan downstream for AA dinucleotide sequences. Record the occurrence of each AA and the 3' adjacent 19 nucleotides as potential siRNA target sites. Tuschal et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with binding of the siRNA endonuclease complex.

2. Compare the potential target sites to the appropriate genome database (human, mouse, rat, etc.) and eliminate from consideration any target sequences with significant homology to other coding sequences. We suggest using BLAST, which can be found on the NCBI server at: www.ncbi.nlm.nih.gov/BLAST/

3. Select qualifying target sequences (i.e., sequences having over 55% GC content) for synthesis.

In one aspect of the invention, the length of the sense nucleic acid is at least 10 nucleotides and may be as long as the naturally-occurring LAT1 transcript. Preferably, the sense nucleic acid is less than 75, 50, or 25 nucleotides in length. It is further preferred that the sense nucleic acid comprises at least 19 nucleotides. Most preferably, the sense nucleic acid is 19-25 nucleotides in length. Examples of LAT1 siRNA sense nucleic acids of the present invention which inhibit LAT1 expression in mammalian cells include oligonucleotides comprising any one of the following target sequences of the LAT1 gene: nucleotides 145-165 (SEQ ID NO: 4), 217-237 (SEQ ID NO: 6), 466-486 (SEQ ID NO: 10), 628-648 (SEQ ID NO: 13), 796-816 (SEQ ID NO: 22), 1243-1263 (SEQ ID NO: 34), 525-545 (SEQ ID NO: 58), 624-644 (SEQ ID NO: 61), 1245-1265 (SEQ ID NO: 81), 1316-1336 (SEQ ID NO: 83), 1410-1430 (SEQ ID NO: 87), 147-165 (SEQ ID NO: 95), 219-237 (SEQ ID NO: 96), 468-486 (SEQ ID NO: 97), 630-648 (SEQ ID NO: 98), 798-816 (SEQ ID NO: 99), 1247-1263 (SEQ ID NO: 100), 527-545 (SEQ ID NO: 101), 1247-1265 (SEQ ID NO: 102), 1318-1336 (SEQ ID NO: 103), 1412-1430 (SEQ ID NO: 104).

One hundred and four sequences, which set forth the sequence for one strand of the double stranded is RNA, were generated for LAT-1. These included the following nucleotide sequences:

| | |
|---|---|
| SEQ ID No 1 | AAGCGGCGCGCGCTAGCGGCG |
| SEQ ID No 2 | AAGGAAGAGGCGCGGGAGAAG |
| SEQ ID No 3 | AAGAGGCGCGGGAGAAGATGC |
| SEQ ID No 4 | AAGATGCTGGCCGCCAAGAGC |
| SEQ ID No 5 | AAGAGCGCGGACGGCTCGGCG |
| SEQ ID No 6 | AACATCACGCTGCTCAACGGC |
| SEQ ID No 7 | AAGGAGGCAGGCTCGCCGGGG |
| SEQ ID No 8 | AAATCGGGCGGCGACTACGCC |
| SEQ ID No 9 | AATCGGGCGGCGACTACGCCT |
| SEQ ID No 10 | AAGCTCTGGATCGAGCTGCTC |
| SEQ ID No 11 | AAGCCGCTCTTCCCCACCTGC |
| SEQ ID No 12 | AAGCTCGTGGCCTGCCTCTGC |
| SEQ ID No 13 | AACTGCTACAGCGTGAAGGCC |
| SEQ ID No 14 | AAGGCCGCCACCCGGGTCCAG |
| SEQ ID No 15 | AAGCTCCTGGCCCTGGCCCTG |
| SEQ ID No 16 | AAGGGTGATGTGTCCAATCTA |
| SEQ ID No 17 | AATCTAGATCCCAACTTCTCA |
| SEQ ID No 18 | AACTTCTCATTTGAAGGCACC |
| SEQ ID No 19 | AAGGCACCAAACTGGATGTGG |
| SEQ ID No 20 | AAACTGGATGTGGGGAACATT |
| SEQ ID No 21 | AACTGGATGTGGGGAACATTG |
| SEQ ID No 22 | AACATTGTGCTGGCATTATAC |
| SEQ ID No 23 | AATTACTTGAATTTCGTCACA |
| SEQ ID No 24 | AATTTCGTCACAGAGGAAATG |
| SEQ ID No 25 | AAATGATCAACCCCTACAGAA |
| SEQ ID No 26 | AATGATCAACCCCTACAGAAA |
| SEQ ID No 27 | AACCCCTACAGAAACCTGCCC |
| SEQ ID No 28 | AAACCTGCCCCTGGCCATCAT |
| SEQ ID No 29 | AACCTGCCCCTGGCCATCATC |
| SEQ ID No 30 | AACCTGGCCTACTTCACCACC |
| SEQ ID No 31 | AACTATCACCTGGGCGTCATG |
| SEQ ID No 32 | AATGGGTCCCTGTTCACATCC |
| SEQ ID No 33 | AAGGCCACCTGCCCTCCATCC |
| SEQ ID No 34 | AAGGACATCTTCTCCGTCATC |
| SEQ ID No 35 | AACTTCTTCAGCTTCTTCAAC |
| SEQ ID No 36 | AACTGGCTCTGCGTGGCCCTG |
| SEQ ID No 37 | AAAGCCTGAGCTTGAGCGGCC |
| SEQ ID No 38 | AAGCCTGAGCTTGAGCGGCCC |
| SEQ ID No 39 | AAGGTGAACCTGGCCCTGCCT |
| SEQ ID No 40 | AACCTGGCCCTGCCTGTGTTC |
| SEQ ID No 41 | AAGACACCCGTGGAGTGTGGC |
| SEQ ID No 42 | AAAAACAAGCCCAAGTGGCTC |
| SEQ ID No 43 | AAACAAGCCCAAGTGGCTCCT |
| SEQ ID No 44 | AACAAGCCCAAGTGGCTCCTC |
| SEQ ID No 45 | AAGCCCAAGTGGCTCCTCCAG |
| SEQ ID No 46 | AAGTGGCTCCTCCAGGGCATC |
| SEQ ID No 47 | AAGCTCATGCAGGTGGTCCCC |
| SEQ ID No 48 | GGCGCCGGCGGCCGAGGAGAA |
| SEQ ID No 49 | CCGGCGGCCGAGGAGAAGGAA |
| SEQ ID No 50 | GGAGAAGATGCTGGCCGCCAA |
| SEQ ID No 51 | GAAGGAAGAGGCGCGGGAGAA |
| SEQ ID No 52 | GGAGAAGATGCTGGCCGCCAA |
| SEQ ID No 53 | GGGCGTGACCCTGCAGCGGAA |
| SEQ ID No 54 | GACGCCCACGGGCGTGCTCAA |
| SEQ ID No 55 | GCTCGGCACCACCATCTCCAA |
| SEQ ID No 56 | CTCGGCACCACCATCTCCAAA |
| SEQ ID No 57 | CTCGCTGCCCGCCTTCCTCAA |

-continued

| SEQ ID No 58 | CTTCGCCACCTACCTGCTCAA |
| --- | --- |
| SEQ ID No 59 | GGTGCCCGAGGAGGCAGCCAA |
| SEQ ID No 60 | GCTGCTGCTCACGGCCGTGAA |
| SEQ ID No 61 | CGTGAACTGCTACAGCGTGAA |
| SEQ ID No 62 | GGATGCCTTTGCCGCCGCCAA |
| SEQ ID No 63 | GGGCTTCGTCCAGATCGGGAA |
| SEQ ID No 64 | CGGGAAGGGTGATGTGTCCAA |
| SEQ ID No 65 | TGTGTCCAATCTAGATCCCAA |
| SEQ ID No 66 | GATCCCAACTTCTCATTTGAA |
| SEQ ID No 67 | CTTCTCATTTGAAGGCACCAA |
| SEQ ID No 68 | TTCTCATTTGAAGGCACCAAA |
| SEQ ID No 69 | ACCAAACTGGATGTGGGGAA |
| SEQ ID No 70 | CTTTGCCTATGGAGGATGGAA |
| SEQ ID No 71 | TGGAGGATGGAATTACTTGAA |
| SEQ ID No 72 | TGAATTTCGTCACAGAGGAAA |
| SEQ ID No 73 | CGTCACAGAGGAAATGATCAA |
| SEQ ID No 74 | AAATGATCAACCCCTACAGAA |
| SEQ ID No 75 | AATGATCAACCCCTACAGAAA |
| SEQ ID No 76 | GCTGGTGTACGTGCTGACCAA |
| SEQ ID No 77 | CGTGGCCGTGGACTTCGGGAA |
| SEQ ID No 78 | GTCCTGCTTCGGCTCCGTCAA |
| SEQ ID No 79 | TTCTTCGTGGGGTCCCGGGAA |
| SEQ ID No 80 | GCTGCTCTACGCCTTCTCCAA |
| SEQ ID No 81 | GGACATCTTCTCCGTCATCAA |
| SEQ ID No 82 | CAACTTCTTCAGCTTCTTCAA |
| SEQ ID No 83 | TGATCTGGCTGCGCCACAGAA |
| SEQ ID No 84 | GATCTGGCTGCGCCACAGAAA |
| SEQ ID No 85 | TGAGCTTGAGCGGCCCATCAA |
| SEQ ID No 86 | TGAGCGGCCCATCAAGGTGAA |
| SEQ ID No 87 | GATCGCCGTCTCCTTCTGGAA |
| SEQ ID No 88 | CTTCTTCGGGGTCTGGTGGAA |
| SEQ ID No 89 | TTCTTCGGGGTCTGGTGGAAA |
| SEQ ID No 90 | TCTTCGGGGTCTGGTGGAAAA |
| SEQ ID No 91 | CTTCGGGGTCTGGTGGAAAAA |
| SEQ ID No 92 | CGGGGTCTGGTGGAAAAACAA |
| SEQ ID No 93 | CTGGTGGAAAAACAAGCCCAA |
| SEQ ID No 94 | CACGACCGTCCTGTGTCAGAA |
| SEQ ID No 95 | AAGATGCTGGCCGCCAAGAGC |
| SEQ ID No 96 | AACATCACGCTGCTCAACGGC |
| SEQ ID No 97 | AAGCTCTGGATCGAGCTGCTC |
| SEQ ID No 98 | AACTGCTACAGCGTGAAGGCC |
| SEQ ID No 99 | AACATTGTGCTGGCATTATAC |
| SEQ ID No 100 | AAGGACATCTTCTCCGTCATC |
| SEQ ID No 101 | CTTCGCCACCTACCTGCTCAA |
| SEQ ID No 102 | GGACATCTTCTCCGTCATCAA |
| SEQ ID No 103 | TGATCTGGCTGCGCCACAGAA |
| SEQ ID No 104 | GATCGCCGTCTCCTTCTGGAA |

The LAT1 gene specificity was confirmed by searching NCBI BlastN database. The siRNAs were chemically synthesized.

All of the forty-two purified siRNA duplexes were complexed with lipofectamine and added to the cells for 12 h in serum-free medium. Thereafter, cells were cultured for 72-96 h in serum-supplemented medium, which was replaced by serum-free medium 24 h before the experiments. A scrambled negative siRNA duplex was used as control.

The LAT1-siRNA is directed to a single target LAT1 gene sequence. Alternatively, the siRNA is directed to multiple target LAT1 gene sequences. For example, the composition contains LAT1-siRNA directed to two, three, four, five or more LAT1 target sequences. By LAT1 target sequence is meant a nucleotide sequence that is identical to a portion of the LAT1 gene. The target sequence can include the 5' untranslated (UT) region, the open reading frame (ORF) or the 3' untranslated region of the human LAT1 gene. Alternatively, the siRNA is a nucleic acid sequence complementary to an upstream or downstream modulator of LAT1 gene expression. Examples of upstream and downstream modulators include, a transcription factor that binds the LAT1 gene promoter, a kinase or phosphatase that interacts with the LAT1 polypeptide, a LAT1 promoter or enhance.

LAT1-siRNA which hybridize to target mRNA decrease or inhibit production of the LAT1 polypeptide product encoded by the LAT1 gene by associating with the normally single-stranded mRNA transcript, thereby interfering with translation and thus, expression of the protein. Exemplary nucleic acid sequence for the production of LAT1-siRNA include the sequences of nucleotides 145-165 (SEQ ID NO: 4), 217-237 (SEQ ID NO: 6), 466-486 (SEQ ID NO: 10), 628-648 (SEQ ID NO: 13), 796-816 (SEQ ID NO: 22), 1243-1263 (SEQ ID NO: 34), 525-545 (SEQ ID NO: 58), 624-644 (SEQ ID NO: 61), 1245-1265 (SEQ ID NO: 81), 1316-1336 (SEQ ID NO: 83), 1410-1430 (SEQ ID NO: 87), 147-165 (SEQ ID NO: 95), 219-237 (SEQ ID NO: 96), 468-486 (SEQ ID NO: 97), 630-648 (SEQ ID NO: 98), 798-816 (SEQ ID NO: 99), 1247-1263 (SEQ ID NO: 100), 527-545 (SEQ ID NO: 101), 1247-1265 (SEQ ID NO: 102), 1318-1336 (SEQ ID NO: 103), 1412-1430 (SEQ ID NO: 104) as the target sequence. In a further embodiment, in order to enhance the inhibition activity of the siRNA, nucleotide "u" can be added to 3' end of the antisense strand of the target sequence. Preferably at least 2, more preferably 2 to 10, and most preferably 2 to 5 u's are added. The added u's form single strand at the 3' end of the antisense strand of the siRNA.

The LAT1-siRNA can be directly introduced into the cells in a form that is capable of binding to the mRNA transcripts. Alternatively, a vector encoding the LAT1-siRNA can be introduced into the cells.

A loop sequence consisting of an arbitrary nucleotide sequence can be located between the sense and antisense sequence in order to form a hairpin loop structure. Thus, the present invention also provides siRNA having the general formula 5'-[A]-[B]-[A']-3', wherein [A] is a ribonucleotide sequence corresponding to a target sequence of the LAT1 gene. Preferably [A] is a sequence selected from the group consisting of nucleotides 145-165 (SEQ ID NO: 4), 217-237 (SEQ ID NO: 6), 466-486 (SEQ ID NO: 10), 628-648 (SEQ ID NO: 13), 796-816 (SEQ ID NO: 22), 1243-1263 (SEQ ID NO: 34), 525-545 (SEQ ID NO: 58), 624-644 (SEQ ID NO: 61), 1245-1265 (SEQ ID NO: 81), 1316-1336 (SEQ ID NO: 83), 1410-1430 (SEQ ID NO: 87), 147-165 (SEQ ID NO: 95), 219-237 (SEQ ID NO: 96), 468-486 (SEQ ID NO: 97), 630-648 (SEQ ID NO: 98), 798-816 (SEQ ID NO: 99), 1247-1263 (SEQ ID NO: 100), 527-545 (SEQ ID NO: 101), 1247-1265 (SEQ ID NO: 102), 1318-1336 (SEQ ID NO: 103), 1412-1430 (SEQ ID NO: 104); [B] is a ribonucleotide sequence consisting of 3 to 23 nucleotides; and [A'] is a ribonucleotide sequence consisting of the complementary sequence of [A]. The region [A] hybridizes to [A'], and then a loop consisting of region [B] is formed. The loop sequence may be preferably 3 to 23 nucleotide in length. Suitable loop sequences are described at www.ambion.com/techlib/tb/tb_506.html. Furthermore, loop sequence consisting of 23 nucleotides also provides active siRNA (Jacque et al., 2002). Preferred loop sequences included:

AUG: (Sui et al., 2002).
CCC, CCACC or CCACACC: (Paul et al., 2002).
UUCG: (Lee et al., 2002).
CTCGAG or AAGCUU: (Biology, 2003).
UUCAAGAGA: (Yu et al., 2002).

The loop sequence can be selected from group consisting of AUG, CCC, UUCG, CCACC, CTCGAG, AAGCUU, CCACACC, and UUCAAGAGA. Preferably the loop sequence is UUCAAGAGA ("ttcaagaga" in DNA).

In a further aspect of the invention, the length of the sense nucleic acid is at least 10 nucleotides and may be as long as the naturally-occurring ASCT2 transcript. Preferably, the sense nucleic acid is less than 75, 50, or 25 nucleotides in length. It is further preferred that the sense nucleic acid comprises at least 19 nucleotides. Most preferably, the sense nucleic acid is 19-25 nucleotides in length. Examples of ASCT2 siRNA sense nucleic acids of the present invention which inhibit ASCT2 expression in mammalian cells include oligonucleotides comprising any one of the following target sequences of the ASCT2 gene: nucleotides 300-320 (SEQ ID NO: 209), 452-472 (SEQ ID NO: 216), 773-793 (SEQ ID NO: 225), 776-796 (SEQ ID NO: 226), 830-850 (SEQ ID NO: 228), 1122-1142 (SEQ ID NO: 235), 1123-1143 (SEQ ID NO: 236), 1124-1144 (SEQ ID NO: 237), 1150-1170 (SEQ ID NO: 238), 769-789 (SEQ ID NO: 260), 994-1014 (SEQ ID NO: 264), 1066-1086 (SEQ ID NO: 267), 1131-1151 (SEQ ID NO: 271), 1154-1174 (SEQ ID NO: 272), 1264-1284 (SEQ ID NO: 278), 1268-1288 (SEQ ID NO: 279), 302-320 (SEQ ID NO: 281), 454-472 (SEQ ID NO: 282), 775-793 (SEQ ID NO: 283), 778-796 (SEQ ID NO: 284), 832-850 (SEQ ID NO: 285), 1124-1142 (SEQ ID NO: 286), 1125-1143 (SEQ ID NO: 287), 1126-1144 (SEQ ID NO: 288), 1152-1170 (SEQ ID NO: 289), 771-789 (SEQ ID NO: 291), 996-1014 (SEQ ID NO: 292), 1068-1086 (SEQ ID NO: 293), 1133-1151 (SEQ ID NO: 294), 1156-1174 (SEQ ID NO: 295), 1266-1284 (SEQ ID NO: 296), 1270-1288 (SEQ ID NO: 297).

Eighty-nine sequences, which set forth the sequence for one strand of the double stranded is RNA, were generated for ASCT2. These included the following nucleotide sequences:

| | |
|---|---|
| SEQ ID No 209 | AAGAGAGGAATATCACCGGAA |
| SEQ ID No 210 | AATATCACCGGAACCAGGGTG |
| SEQ ID No 211 | AACCAGGGTGAAGGTGCCCGT |
| SEQ ID No 212 | AAGGTGCCCGTGGGGCAGGAG |
| SEQ ID No 213 | AACATCCTGGGCTTGGTAGTG |
| SEQ ID No 214 | AAGCTGGGGCCTGAAGGGGAG |
| SEQ ID No 215 | AAGGGGAGCTGCTTATCCGCT |
| SEQ ID No 216 | AACTCCTTCAATGAGGCCACC |
| SEQ ID No 217 | AATGAGGCCACCATGGTTCTG |
| SEQ ID No 218 | AAGATCGTGGAGATGGAGGAT |
| SEQ ID No 219 | AAGTACATTCTGTGCTGCCTG |
| SEQ ID No 220 | AAAAACCCCTACCGCTTCCTG |
| SEQ ID No 221 | AAAACCCCTACCGCTTCCTGT |
| SEQ ID No 222 | AAACCCCTACCGCTTCCTGTG |
| SEQ ID No 223 | AACCCCTACCGCTTCCTGTGG |
| SEQ ID No 224 | AAGTGCGTGGAGGAGAATAAT |
| SEQ ID No 225 | AATAATGGCGTGGCCAAGCAC |
| SEQ ID No 226 | AATGGCGTGGCCAAGCACATC |
| SEQ ID No 227 | AAGCACATCAGCCGTTTCATC |
| SEQ ID No 228 | AACATGGACGGTGCCGCGCTC |
| SEQ ID No 229 | AAAGATCATCACCATCCTGGT |
| SEQ ID No 230 | AAGATCATCACCATCCTGGTC |
| SEQ ID No 231 | AAGCAGTCAACCTCCCGGTCG |
| SEQ ID No 232 | AACCTCCCGGTCGACCATATC |
| SEQ ID No 233 | AATGTAGAAGGTGACGCTCTG |
| SEQ ID No 234 | AAGGTGACGCTCTGGGGGCAG |
| SEQ ID No 235 | AAAATTACGTGGACCGTACGG |
| SEQ ID No 236 | AAATTACGTGGACCGTACGGA |
| SEQ ID No 237 | AATTACGTGGACCGTACGGAG |
| SEQ ID No 238 | AAGCACAGAGCCTGAGTTGAT |
| SEQ ID No 239 | AAGTGAAGAGTGAGCTGCCCC |
| SEQ ID No 240 | AAGAGTGAGCTGCCCCTGGAT |
| SEQ ID No 241 | AAGGAAACCCCCTCCTCAAAC |
| SEQ ID No 242 | AAACCCCCTCCTCAAACACTA |
| SEQ ID No 243 | AAACACTATCGGGGGCCCGCA |
| SEQ ID No 244 | AACACTATCGGGGCCCGCAG |
| SEQ ID No 245 | AAGAGAGGAATATCACCGGAA |
| SEQ ID No 246 | TATCACCGGAACCAGGGTGAA |
| SEQ ID No 247 | GCAGGAGGTGGAGGGGATGAA |
| SEQ ID No 248 | CTTTGGTGTGGCGCTGCGGAA |
| SEQ ID No 249 | CTGCGGAAGCTGGGGCCTGAA |

| | |
|---|---|
| SEQ ID No 250 | GCTGCTTATCCGCTTCTTCAA |
| SEQ ID No 251 | CCGCTTCTTCAACTCCTTCAA |
| SEQ ID No 252 | CATGTTCCTGGTGGCTGGCAA |
| SEQ ID No 253 | ACTCTTTGCCCGCCTTGGCAA |
| SEQ ID No 254 | CTACTTCCTCTTCACCCGCAA |
| SEQ ID No 255 | TACTTCCTCTTCACCCGCAAA |
| SEQ ID No 256 | CTTCCTCTTCACCCGCAAAAA |
| SEQ ID No 257 | CACGCTGCCGCTGATGATGAA |
| SEQ ID No 258 | GATGAAGTGCGTGGAGGAGAA |
| SEQ ID No 259 | GAAGTGCGTGGAGGAGAATAA |
| SEQ ID No 260 | GGAGAATAATGGCGTGGCCAA |
| SEQ ID No 261 | GCCCATCGGCGCCACCGTCAA |
| SEQ ID No 262 | GCAGTCCTTGGACTTCGTAAA |
| SEQ ID No 263 | AGCAGTCCTTGGACTTCGTAA |
| SEQ ID No 264 | CATCATCCTCGAAGCAGTCAA |
| SEQ ID No 265 | ACTCTGGCCATCATCCTCGAA |
| SEQ ID No 266 | TGTACCGTCCTCAATGTAGAA |
| SEQ ID No 267 | CCGGTCCTGTACCGTCCTCAA |
| SEQ ID No 268 | GGGGGCAGGACTCCTCCAAAA |
| SEQ ID No 269 | TGGGGGCAGGACTCCTCCAAA |
| SEQ ID No 270 | CTGGGGGCAGGACTCCTCCAA |
| SEQ ID No 271 | TGGACCGTACGGAGTCGAGAA |
| SEQ ID No 272 | ACAGAGCCTGAGTTGATACAA |
| SEQ ID No 273 | GCCTGAGTTGATACAAGTGAA |
| SEQ ID No 274 | CTGCCAGTCCCCACTGAGGAA |
| SEQ ID No 275 | CAGTCCCCACTGAGGAAGGAA |
| SEQ ID No 276 | GGAAGGAAACCCCCTCCTCAA |
| SEQ ID No 277 | GAAGGAAACCCCCTCCTCAAA |
| SEQ ID No 278 | TGCCACGGTCGCCTCTGAGAA |
| SEQ ID No 279 | ACGGTCGCCTCTGAGAAGGAA |
| SEQ ID No 280 | GAGAAGGAATCAGTCATGTAA |
| SEQ ID No 281 | GAGAGGAATATCACCGGAA |
| SEQ ID No 282 | GCTGGGGCCTGAAGGGGAG |
| SEQ ID No 283 | TAATGGCGTGGCCAAGCAC |
| SEQ ID No 284 | TGGCGTGGCCAAGCACATC |
| SEQ ID No 285 | CATGGACGGTGCCGCGCTC |
| SEQ ID No 286 | AATTACGTGGACCGTACGG |
| SEQ ID No 287 | ATTACGTGGACCGTACGGA |
| SEQ ID No 288 | TTACGTGGACCGTACGGAG |
| SEQ ID No 289 | GCACAGAGCCTGAGTTGAT |
| SEQ ID No 290 | GAGAGGAATATCACCGGAA |
| SEQ ID No 291 | AGAATAATGGCGTGGCCAA |
| SEQ ID No 292 | TCATCCTCGAAGCAGTCAA |
| SEQ ID No 293 | GGTCCTGTACCGTCCTCAA |
| SEQ ID No 294 | GACCGTACGGAGTCGAGAA |
| SEQ ID No 295 | AGAGCCTGAGTTGATACAA |
| SEQ ID No 296 | CCACGGTCGCCTCTGAGAA |
| SEQ ID No 297 | GGTCGCCTCTGAGAAGGAA |

The ASCT2 gene specificity was confirmed by searching NCBI BlastN database. The siRNAs were chemically synthesized.

All of the forty-two purified siRNA duplexes were complexed with lipofectamine and added to the cells for 12 h in serum-free medium. Thereafter, cells were cultured for 72-96 h in serum-supplemented medium, which was replaced by serum-free medium 24 h before the experiments. A scrambled negative siRNA duplex was used as control.

The ASCT2-siRNA is directed to a single target ASCT2 gene sequence. Alternatively, the siRNA is directed to multiple target ASCT2 gene sequences. For example, the composition contains ASCT2-siRNA directed to two, three, four, five or more ASCT2 target sequences. By ASCT2 target sequence is meant a nucleotide sequence that is identical to a portion of the ASCT2 gene. The target sequence can include the 5' untranslated (UT) region, the open reading frame (ORF) or the 3' untranslated region of the human ASCT2 gene. Alternatively, the siRNA is a nucleic acid sequence complementary to an upstream or downstream modulator of ASCT2 gene expression. Examples of upstream and downstream modulators include, a transcription factor that binds the ASCT2 gene promoter, a kinase or phosphatase that interacts with the ASCT2 polypeptide, a ASCT2 promoter or enhance.

ASCT2-siRNA which hybridize to target mRNA decrease or inhibit production of the ASCT2 polypeptide product encoded by the ASCT2 gene by associating with the normally single-stranded mRNA transcript, thereby interfering with translation and thus, expression of the protein. Exemplary nucleic acid sequence for the production of ASCT2-siRNA include the sequences of nucleotides 300-320 (SEQ ID NO: 209), 452-472 (SEQ ID NO: 216), 773-793 (SEQ ID NO: 225), 776-796 (SEQ ID NO: 226), 830-850 (SEQ ID NO: 228), 1122-1142 (SEQ ID NO: 235), 1123-1143 (SEQ ID NO: 236), 1124-1144 (SEQ ID NO: 237), 1150-1170 (SEQ ID NO: 238), 769-789 (SEQ ID NO: 260), 994-1014 (SEQ ID NO: 264), 1066-1086 (SEQ ID NO: 267), 1131-1151 (SEQ ID NO: 271), 1154-1174 (SEQ ID NO: 272), 1264-1284 (SEQ ID NO: 278), 1268-1288 (SEQ ID NO: 279), 302-320 (SEQ ID NO: 281), 454-472 (SEQ ID NO: 282), 775-793 (SEQ ID NO: 283), 778-796 (SEQ ID NO: 284), 832-850 (SEQ ID NO: 285), 1124-1142 (SEQ ID NO: 286), 1125-1143 (SEQ ID NO: 287), 1126-1144 (SEQ ID NO: 288), 1152-1170 (SEQ ID NO: 289), 771-789 (SEQ ID NO: 291), 996-1014 (SEQ ID NO: 292), 1068-1086 (SEQ ID NO: 293), 1133-1151 (SEQ ID NO: 294), 1156-1174 (SEQ ID NO: 295), 1266-1284 (SEQ ID NO: 296), 1270-1288 (SEQ ID NO: 297) as the target sequence. Furthermore, in order to enhance the inhibition activity of the siRNA, nucleotide "u" can be added to 3' end of the antisense strand of the target sequence.

Preferably at least 2, more preferably 2 to 10, and most preferably 2 to 5 u's are added. The added u's form single strand at the 3' end of the antisense strand of the siRNA.

The ASCT2-siRNA can be directly introduced into the cells in a form that is capable of binding to the mRNA transcripts. Alternatively, a vector encoding the ASCT2-siRNA can be introduced into the cells.

A loop sequence consisting of an arbitrary nucleotide sequence can be located between the sense and antisense sequence in order to form a hairpin loop structure. Thus, the present invention also provides siRNA having the general formula 5'-[A]-[B]-[A']-3', wherein [A] is a ribonucleotide sequence corresponding to a target sequence of the ASCT2 gene. Preferably [A] is a sequence selected from the group consisting of nucleotides 300-320 (SEQ ID NO: 209), 452-472 (SEQ ID NO: 216), 773-793 (SEQ ID NO: 225), 776-796 (SEQ ID NO: 226), 830-850 (SEQ ID NO: 228), 1122-1142 (SEQ ID NO: 235), 1123-1143 (SEQ ID NO: 236), 1124-1144 (SEQ ID NO: 237), 1150-1170 (SEQ ID NO: 238), 769-789 (SEQ ID NO: 260), 994-1014 (SEQ ID NO: 264), 1066-1086 (SEQ ID NO: 267), 1131-1151 (SEQ ID NO: 271), 1154-1174 (SEQ ID NO: 272), 1264-1284 (SEQ ID NO: 278), 1268-1288 (SEQ ID NO: 279), 302-320 (SEQ ID NO: 281), 454-472 (SEQ ID NO: 282), 775-793 (SEQ ID NO: 283), 778-796 (SEQ ID NO: 284), 832-850 (SEQ ID NO: 285), 1124-1142 (SEQ ID NO: 286), 1125-1143 (SEQ ID NO: 287), 1126-1144 (SEQ ID NO: 288), 1152-1170 (SEQ ID NO: 289), 771-789 (SEQ ID NO: 291), 996-1014 (SEQ ID NO: 292), 1068-1086 (SEQ ID NO: 293), 1133-1151 (SEQ ID NO: 294), 1156-1174 (SEQ ID NO: 295), 1266-1284 (SEQ ID NO: 296), 1270-1288 (SEQ ID NO: 297); [B] is a ribonucleotide sequence consisting of 3 to 23 nucleotides; and [A'] is a ribonucleotide sequence consisting of the complementary sequence of [A]. The region [A] hybridizes to [A'], and then a loop consisting of region [B] is formed. The loop sequence may be preferably 3 to 23 nucleotide in length. Suitable loop sequences are described at www.ambion.com/techlib/tb/tb_506.html. Furthermore, loop sequence consisting of 23 nucleotides also provides active siRNA (Jacque et al., 2002). Preferred loop sequences included:

AUG: (Sui et al., 2002).
CCC, CCACC or CCACACC: (Paul et al., 2002).
UUCG: (Lee et al., 2002).
CTCGAG or AAGCUU: (Biology, 2003).
UUCAAGAGA: (Yu et al., 2002).

The loop sequence can be selected from group consisting of AUG, CCC, UUCG, CCACC, CTCGAG, AAGCUU, CCACACC, and UUCAAGAGA. Preferably the loop sequence is UUCAAGAGA ("ttcaagaga" in DNA).

The inventors have surprisingly found that siRNAs targeted to certain target sequences of the LAT1 gene or ASCT2 gene are particularly effective at inhibiting sodium-independent [$^{14}$C]-L-leucine uptake or sodium-dependent [$^{14}$C]-L-alanine uptake, respectively, LAT1 or ASCT2 expression, cell growth and growth of tumors overexpressing LAT1 and/or ASCT2 transporters.

In a specific embodiment of the present invention, the sense strand of the LAT1 siRNA used in the present invention comprises or consists of a sequence selected from the group comprising SEQ ID NOS 6, 22, 34, 58 and 61. The siRNA also comprises a corresponding antisense strand. The use of such an siRNA has been found to be particularly effective in inhibiting sodium-independent [$^{14}$C]-L-leucine transport. In a further embodiment, the sense strand of the LAT1 siRNA comprises or consists of at least one sequence selected from the group comprising SEQ ID NO: 110, 126, 138, 162 and 165.

According to a another aspect of the present invention there is provided a siRNA comprising a sense LAT1 nucleic acid and an anti-sense LAT1 nucleic acid, and the sense LAT1 nucleic acid is substantially identical to a target sequence contained within LAT1 mRNA and the anti-sense LAT1 nucleic acid is complementary to the sense LAT1 nucleic acid. The sense and antisense nucleic acids hybridize to each other to form a double-stranded molecule.

The siRNA molecules of the present invention have the property to inhibit expression of the LAT1 gene when introduced into a cell expressing said gene.

The siRNA molecules of the present invention have the property to inhibit cell growth when introduced into a cell expressing LAT1 gene.

The siRNA molecules of the present invention have the property to inhibit tumour growth when introduced into a tumour expressing LAT1 gene.

In a specific embodiment of the present invention, the sense strand of the ASCT2 siRNA used in the present invention comprises or consists of a sequence selected from the group comprising SEQ ID NOS 225, 237, 267 and 278. The siRNA also comprises a corresponding antisense strand. The use of such an siRNA has been found to be particularly effective in inhibiting sodium-independent [$^{14}$C]-L-leucine transport. In a further embodiment, the sense strand of the LAT1 siRNA comprises or consists of at least one sequence selected from the group comprising 314, 326, 356 and 367.

According to a another aspect of the present invention there is provided a siRNA comprising a sense ASCT2 nucleic acid and an anti-sense ASCT2 nucleic acid, and the sense ASCT2 nucleic acid is substantially identical to a target sequence contained within ASCT2 mRNA and the anti-sense ASCT2 nucleic acid is complementary to the sense ASCT2 nucleic acid. The sense and antisense nucleic acids hybridize to each other to form a double-stranded molecule.

The siRNA molecules of the present invention have the property to inhibit expression of the ASCT2 gene when introduced into a cell expressing said gene.

The siRNA molecules of the present invention have the property to inhibit cell growth when introduced into a cell expressing ASCT2 gene.

The siRNA molecules of the present invention have the property to inhibit tumour growth when introduced into a tumour expressing ASCT2 gene.

When combined the siRNA-LAT1 and siRNA-ASCT2 of the present invention have the property to inhibit expression of the LAT1 and ASCT2 genes when introduced into a cell expressing said gene.

When combined the siRNA-LAT1 and siRNA-ASCT2 molecules of the present invention have the property to inhibit cell growth when introduced into a cell expressing the LAT1 and ASCT2 genes.

When combined the siRNA-LAT1 and siRNA-ASCT2 molecules of the present invention have the property to inhibit tumour growth when introduced into a tumour expressing and LAT1 ASCT2 genes.

Another aspect of the invention relates to nucleic acid sequences and vectors encoding the siRNA according to the fourth aspect of the present invention, as well as to compositions comprising them, useful, for example, in the methods of the present invention. Compositions of the present invention may additionally comprise transfection enhancing agents. The nucleic acid sequence may be operably linked to an inducible or regulatable promoter. Suitable vectors are discussed above. Preferably the vector is an adeno-associated viral vector.

The composition of the present invention may additionally comprise a pharmaceutical agent for treating cancer, wherein the agent is different from the siRNA. Preferably the pharmaceutical agent is selected from the group consisting of abarelix, amifostine, aminoglutethimide, anastrozole, bevacizumab, bicalutamide, bleomycin, bortezomib, busulfan, capecitabine, carboplatin, carmustine, cetuximab, chlorambucil, cispatlin, cladribine, cyclophosphamide, cytarabine, dacarbazine, dactinomycin, daunorubicin, docetaxel, doxorubicin, erlotinib, 4'-epidoxorubicin, epirubicin, estramustine, etoposide, floxuridine, fludarabine, 5-fluorouracil, flutamide, gefitinib, gemcitabine, goserelin, hexamethylmelamine, hydroxyurea, ifosfamide, imatinib, irinotecan, leuprolide, megestrol, melphalan, 6-mercatopurine, methotrexate, mitomycin, mitotane, mitoxantrone, oxaliplatin, paclitaxel, pentostatin, prednisone, procarbazine, rituximab, satraplatin, tamoxifen, temozolomide, teniposide, 6-thioguanine, thiotepa, topotecan, toremifen, trastuzumab, triptorelin, valrubicin, vinblastine, vincristine and vinolrebine.

Non-viral delivery siRNA systems involve the creation of nucleic acid transfection reagents. Nucleic acid transfection reagents have two basic properties. First, they must interact in some manner with the nucleic acid cargo. Most often this involves electrostatic forces, which allow the formation of nucleic acid complexes. Formation of a complex ensures that the nucleic acid and transfection reagents are presented simultaneously to the cell membrane. Complexes can be divided into three classes, based on the nature of the delivery reagent: lipoplexes; polyplexes; and lipopolyplexes. Lipoplexes are formed by the interaction of anionic nucleic acids with cationic lipids, polyplexes by interaction with cationic polymers. Lipopolyplex reagents can combine the action of cationic lipids and polymers to deliver nucleic acids. Addition of histone, poly-L-lysine and protamine to some formulations of cationic lipids results in levels of delivery that are higher than either lipid or polymer alone. The combined formulations might also be less toxic. The biocompatible systems most relevant to this purpose are non-viral biodegradable nanocapsules designed especially according to the physical chemistry of nucleic acids. They have an aqueous core surrounded by a biodegradable polymeric envelope, which provides protection and transport of the siRNA into the cytosol and allow the siRNA to function efficiently in vivo.

The present invention also provides a cell containing the siRNA according to the fourth aspect of the present invention or the vector of the present invention. Preferably the cell is a mammalian cell, more preferably a human cell. It is further preferred that the cell is an isolated cell.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification, including reference to sequence database identifiers, are incorporated herein by reference in their entirety. Unless otherwise specified, when reference to sequence database identifiers is made, the version number is 1.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described. The invention is further described in the following non-limiting examples.

The following examples further illustrate the present invention in detail but are not to be construed to limit the scope thereof.

DESCRIPTION OF THE DRAWINGS

FIG. 1. Relative abundance of LAT1 protein and ASCT2 protein in human liver carcinoma SK-HEP-1 cells, human bladder carcinoma T24 cells, human fibrosarcoma HT-1080 cells and human colon cancer HTC-116 cells by western blot (relative to GAPDH).

FIG. 6. 5' DNA sense, 5' sense siRNA and 3' antisense siRNA-LAT1 against nucleotide SEQ ID NO: 58/162/411, 58/387/388, 58/389/390, 58/389/412, 61/165/396, 61/391/392, 61/393/394 and 61/395/396.

FIG. 7. 5' DNA sense, 5' sense siRNA and 3' antisense siRNA-ASCT2 against nucleotide SEQ ID NO: 267/356/

402, 267/397/398, 267/399/400, 267/401/402, 278/367/408, 278/403/404, 278/405/406 and 278/407/408.

FIG. 8. [$^{14}$C]-L-leucine (0.25 µM) (A) and [$^{14}$C]-L-alanine (0.25 µM) (B) uptake at initial rate of uptake (1 min) in human fibrosarcoma HT-1080 cells treated for 6 h with 5 nM anti-LAT1 against nucleotide SEQ ID NO: 58/162/411, 58/387/388, 61/165/396, 61/391/392 and and one commercially available siRNA (SI31011000 from QIAGEN) 5 nM siRNA-ASCT2 against nucleotide SEQ ID NO: 267/356/402, 267/397/398, 278/367/408, 278/403/404 and one commercially available siRNA (SI00097930, from QIAGEN) using 0.4% Lipofectamine 2000 as the transfecting agent at 48 h. Significantly different from corresponding control values (*p<0.01) and values for SEQ ID NO: 267/397/398 ($ p<0.05).

Figure 9:
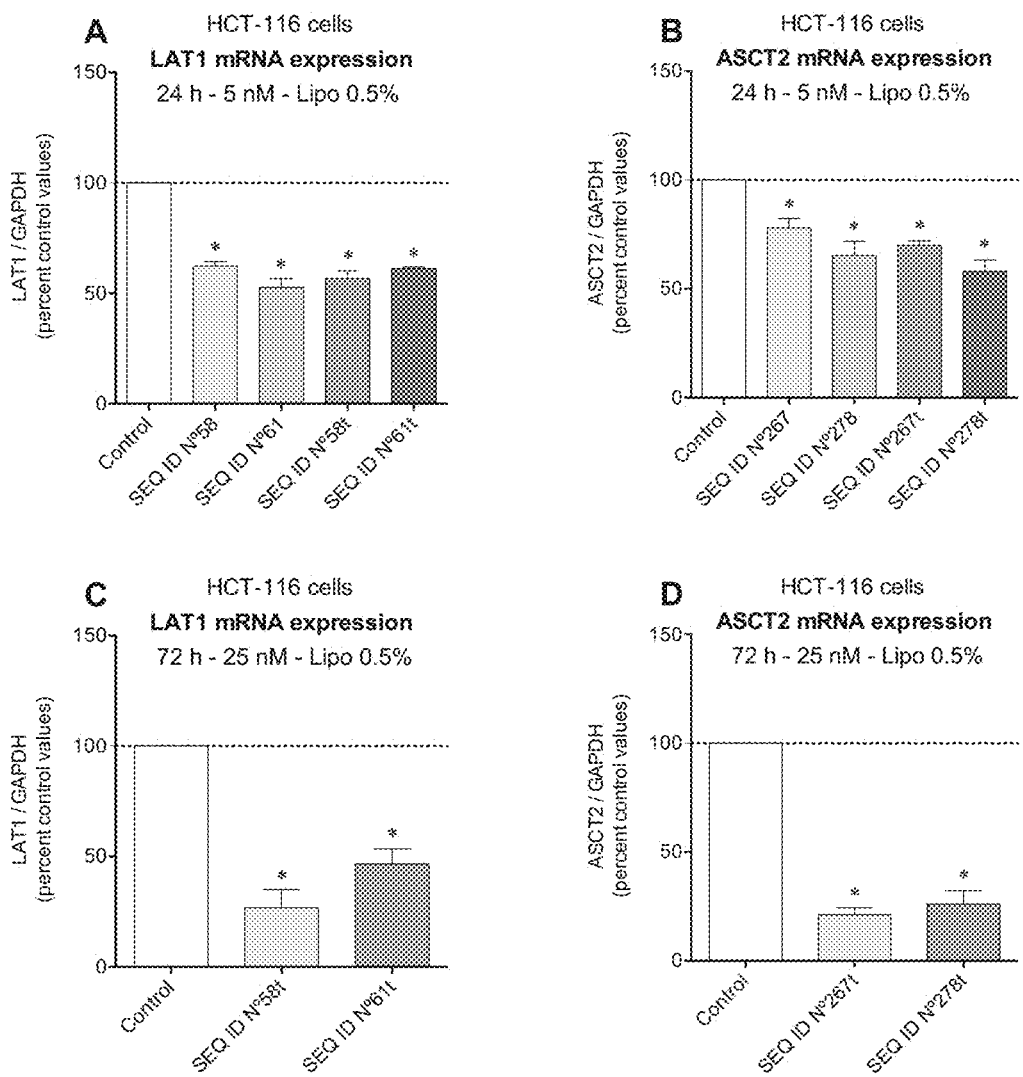

FIG. 9. LAT1 mRNA (A and C) and ASCT2 mRNA (B and D) relative abundance in human colon cancer HTC-116 cells treated for 6 h with 5 or 25 nM siRNA-LAT1 against nucleotide SEQ ID NO: 58/162/411, 61/165/396, 58/387/388 and 61/391/392 and ASCT2 mRNA relative abundance in human colon cancer HTC-116 cells treated for 6 h with 5 or 25 nM siRNA-ASCT2 against nucleotide SEQ ID NO: 267/356/402, 278/367/408, 267/397/398 and 278/403/404 using 0.5% Lipofectamine 2000 as the transfecting agent at 24 h (A and B) or 72 h (C and D). Significantly different from corresponding control values (*p<0.01).

FIG. 10. LAT1 mRNA relative abundance in human colon cancer HTC-116 cells treated for 6 h with (A) 5, 25 and 45 nM siRNA-LAT1 against nucleotide SEQ ID NO: 58/387/388, using (B) 0.5% Lipofectamine 2000®, Lipofectamine RNAiMAX® or Injectin® as the transfecting agents at 72 h. Significantly different from corresponding control values (p<0.01, *p<0.02; ****p<0.001) and corresponding values with Injectin® (# p<0.05).

Figure 11:
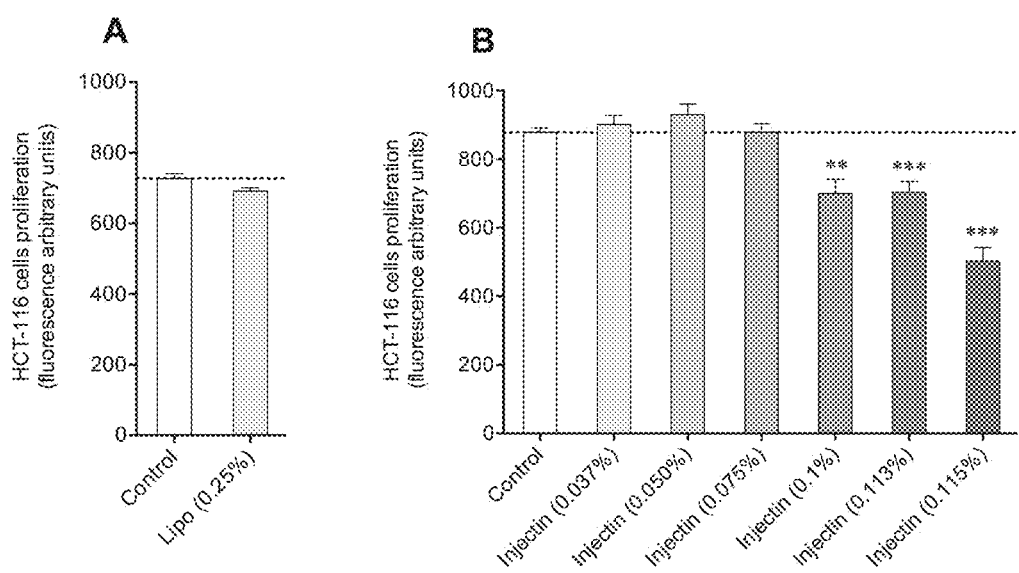

FIG. 11. Effect of transfecting agents Lipofectamine 2000® or Injectin® upon human colon cancer HTC-116 cell density after 72 h exposure. Significantly different from corresponding control values (p<0.01, *p<0.02).

Figure 12:
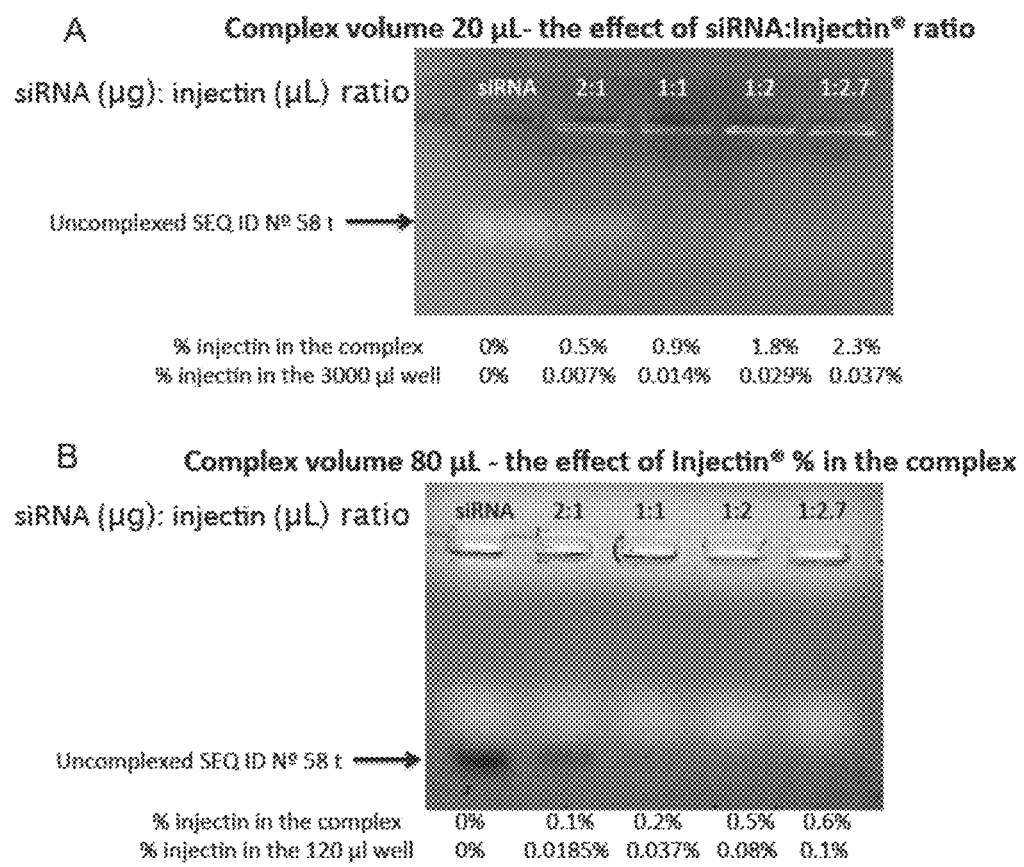

FIG. 12. siRNA complexation analysis by agarose gel electrophoresis in the siRNA:Injectin® complexes at (A) 20 µL and (B) 80 µL complex volumes. In panel A, electrophoresis of siRNA:Injectin® complexes revealed that siRNA is fully complexed when the siRNA:Injectin® ratio is 1:1 and the percentage of Injectin® in the complex mixture is higher than 0.9%. In panel B, siRNA complexation is not effective when the siRNA:Injectin® ratio 1:1 is maintained but the amount of Injectin® in the complex mixture is equal or lower than 0.2%.

Figure 13:
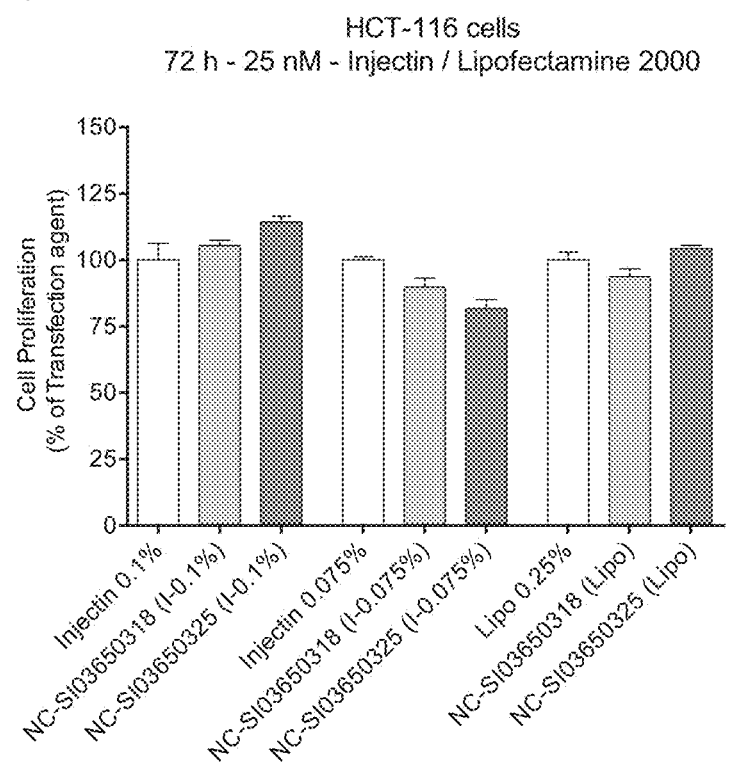

FIG. 13. Effects of negative control siRNA commercial (from QIAGEN) sequences NC-SI03650318 and NC-SI03650325 upon proliferation human colon cancer HTC-116 cells at 72 h exposure times using Injectin® (0.075 and 0.1%) or Lipofectamine 2000® (0.25%) as the transfecting agent.

Figure 14:
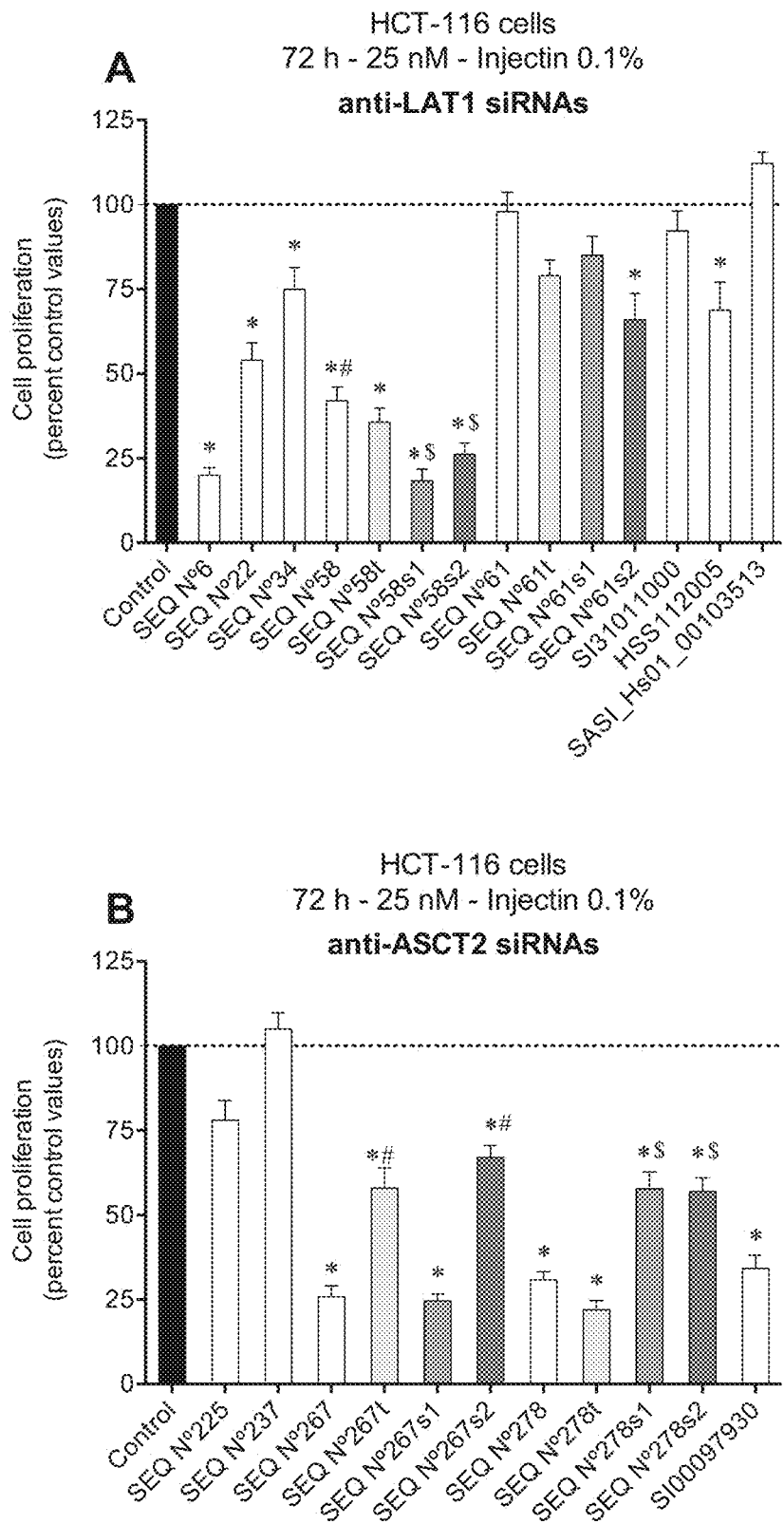

FIG. 14. Effects of (A) siRNA-LAT1 against nucleotide SEQ ID NO: 6, 22, 34, 58/162/411, 58/387/388, 58/389/390, 58/389/412, 61/165/396, 61/391/392, 61/393/394, 61/395/396 and three commercially available siRNAs (SI31011000, HSS112005 and SASI_Hs01_00103513 respectively from QIAGEN, Thermofisher Scientific and Sigma-Aldrich) and (B) siRNA-ASCT2 against nucleotide SEQ ID NO: 225, 237, 267/356/402, 267/397/398, 267/399/400, 267/401/402, 278/367/408, 278/403/404, 278/405/406, 278/407/408 and one commercially available siRNA (SI00097930, from QIAGEN), respectively, upon proliferation of human colon cancer HTC-116 cells at 72 h exposure times using 0.1% Injectin® as the transfecting agent. In panel A, values were significantly different from corresponding control values (*p<0.01), values for SEQ ID NO: 34 (# p<0.05) and values for SEQ ID NO: 58 ($ p<0.05). In panel B, values were significantly different from corresponding control values (*p<0.01), values for SEQ ID NO: 267 (# p<0.05) and values for SEQ ID NO: 278 ($ p<0.05).

Figure 15:
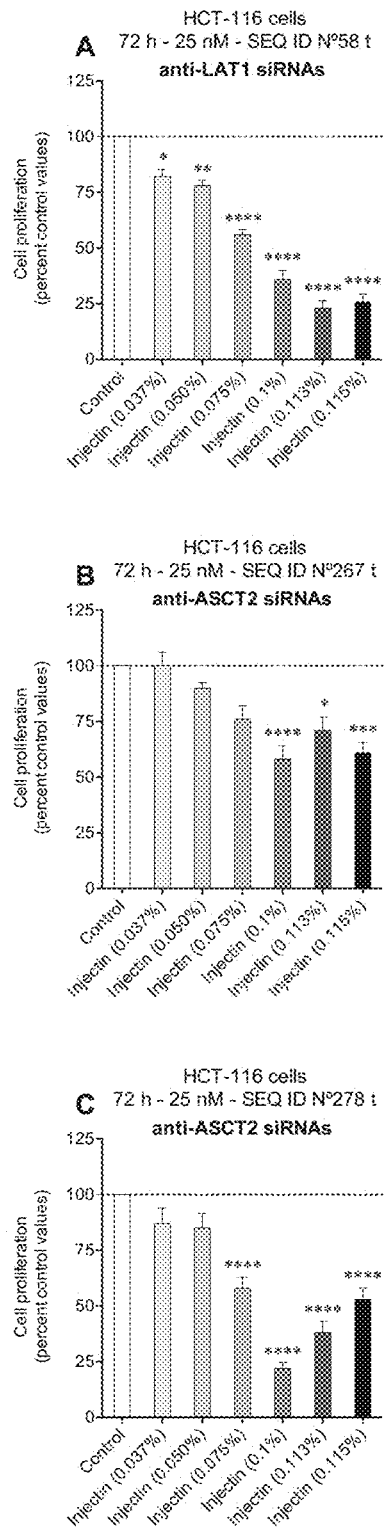

FIG. 15. Effects of siRNA-LAT1 against nucleotide SEQ ID NO: 58/387/388 and siRNA-ASCT2 against nucleotide SEQ ID NO: 267/397/398 and 278/403/404 upon proliferation human colon cancer HTC-116 cells at 72 h exposure times using increasing concentrations (0.037% to 0.15%) of Injectin® as the transfecting agent. Significantly different from corresponding control values (*p<0.05, p<0.01, *p<0.02; ****p<0.001) and corresponding values with Injectin® (# p<0.05).

Figure 16:
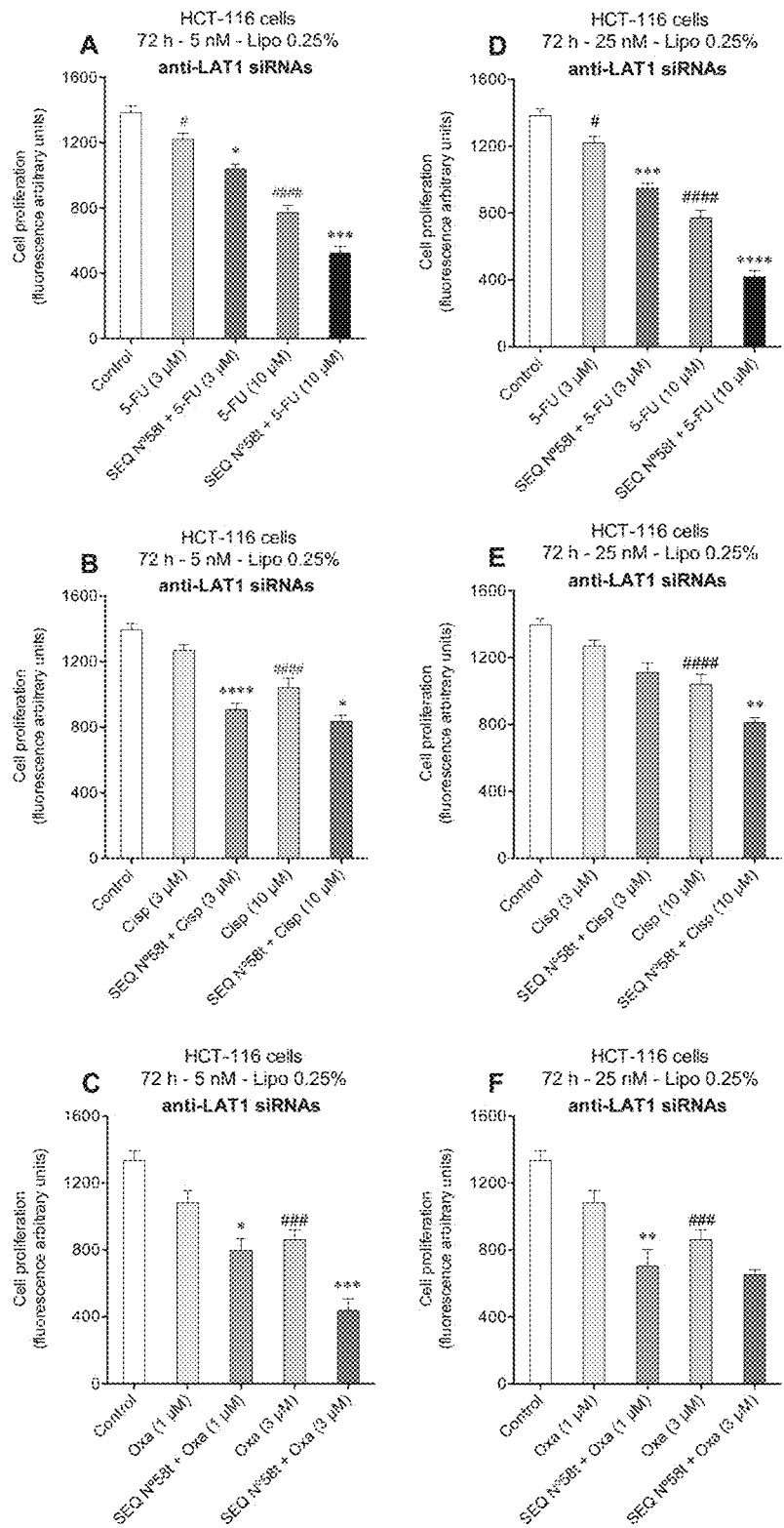

FIG. 16. Effects of 5-fluoruracil (5-FU; 3 and 10 µM), cisplatin (Cisp; 3 and 10 µM) and oxaliplatin (Oxa; 1 and 3 µM) alone or in combination with siRNA-LAT1 against nucleotide SEQ ID NO: 58/387/388 (5 and 25 nM) upon proliferation of human colon cancer HTC-116 cells at 72 h exposure times using increasing concentrations using 0.25% Lipofectamine 2000 as the transfecting agent. Significantly different from corresponding control values (# p<0.05, ####p<0.001) and corresponding values with the antineoplastic cytotoxic agent 5-FU, Cisp or Oxa (*p<0.05 p<0.01, *p<0.02, ****p<0.001).

FIG. 17. Effects of 5-fluoruracil (5-FU; 10 µM) alone or in combination with anti-LAT1 SEQ ID NOS 58/387/388 and 61/391/392 (25 nM) upon proliferation of human colon cancer HTC-116 cells at 72 h exposure times using 0.037% Injectin® as the transfecting agent. Significantly different from corresponding control values (#### p<0.001) and corresponding values with the antineoplastic cytotoxic agent 5-FU (p<0.01, *p<0.001).

FIG. 18. Effects of anti-LAT1 SEQ ID NOS 58/387/388 and 61/391/392 (25 nM) and anti-ASCT2 SEQ ID NOS 267/397/398 and 278/403/404 alone or in combination upon proliferation of human colon cancer HTC-116 cells at 72 h exposure times using Injectin® as the transfecting agent. Significantly different from corresponding control values (*p<0.05p<0.01, *p<0.02, ****p<0.001).

Figure 19:
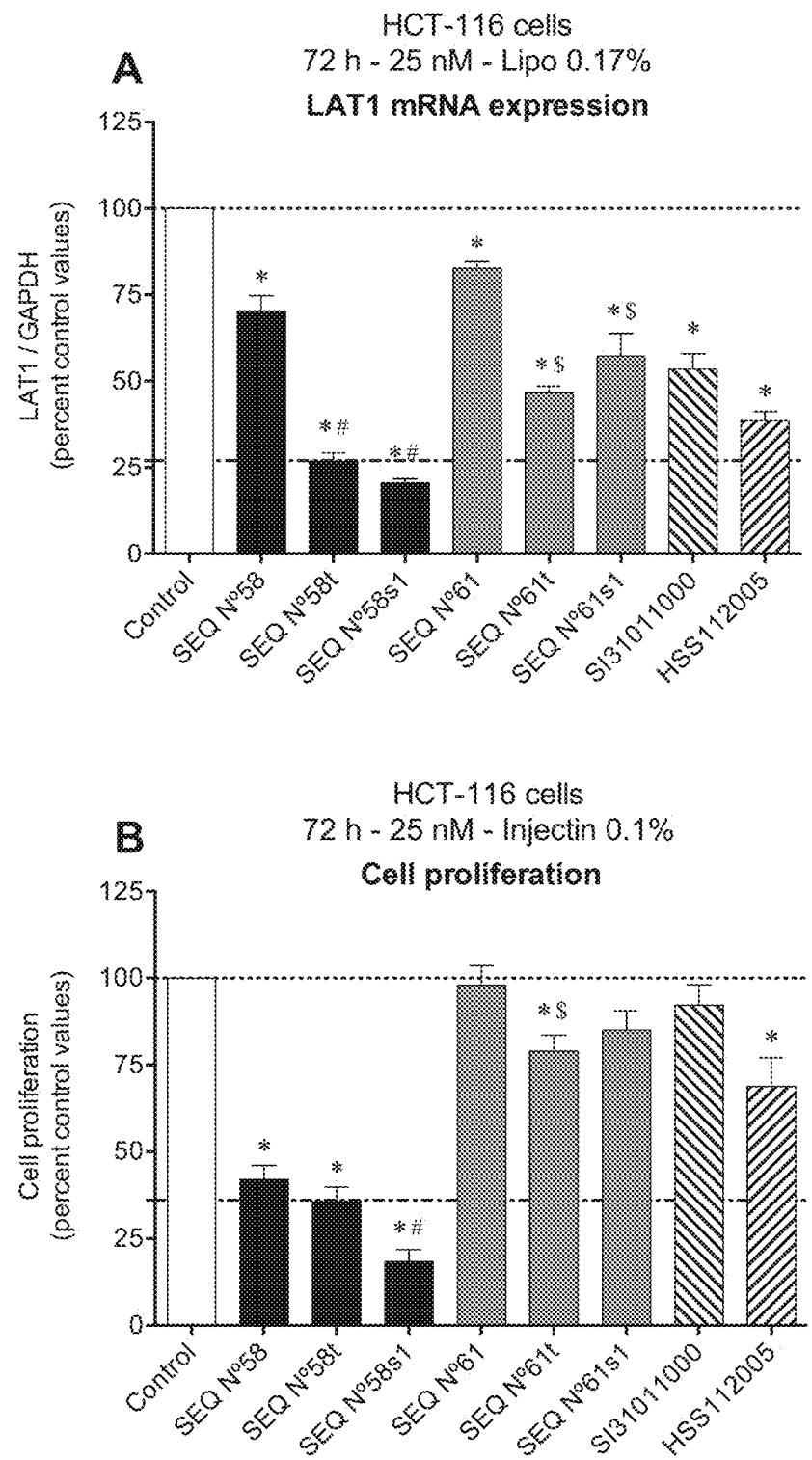

FIG. 19. Effects of anti-LAT1 SEQ ID NOS 58/162/411, 58/387/388, 58/389/390, 61/165/396, 61/391/392, 61/393/394 and two commercially available siRNAs (SI31011000 and HSS112005, respectively from QIAGEN and Thermofisher Scientific) upon (A) LAT1 mRNA relative abundance and (B) upon proliferation of human colon cancer HTC-116 cells at 72 h exposure times using 0.17% Lipofectamine 2000® or 0.1% Injectin® as the transfecting agent. Significantly different from corresponding control values (*p<0.01), values for SEQ ID NO: 58 (#p<0.05) and values for SEQ ID NO: 61 ($ p<0.05).

Figure 20:
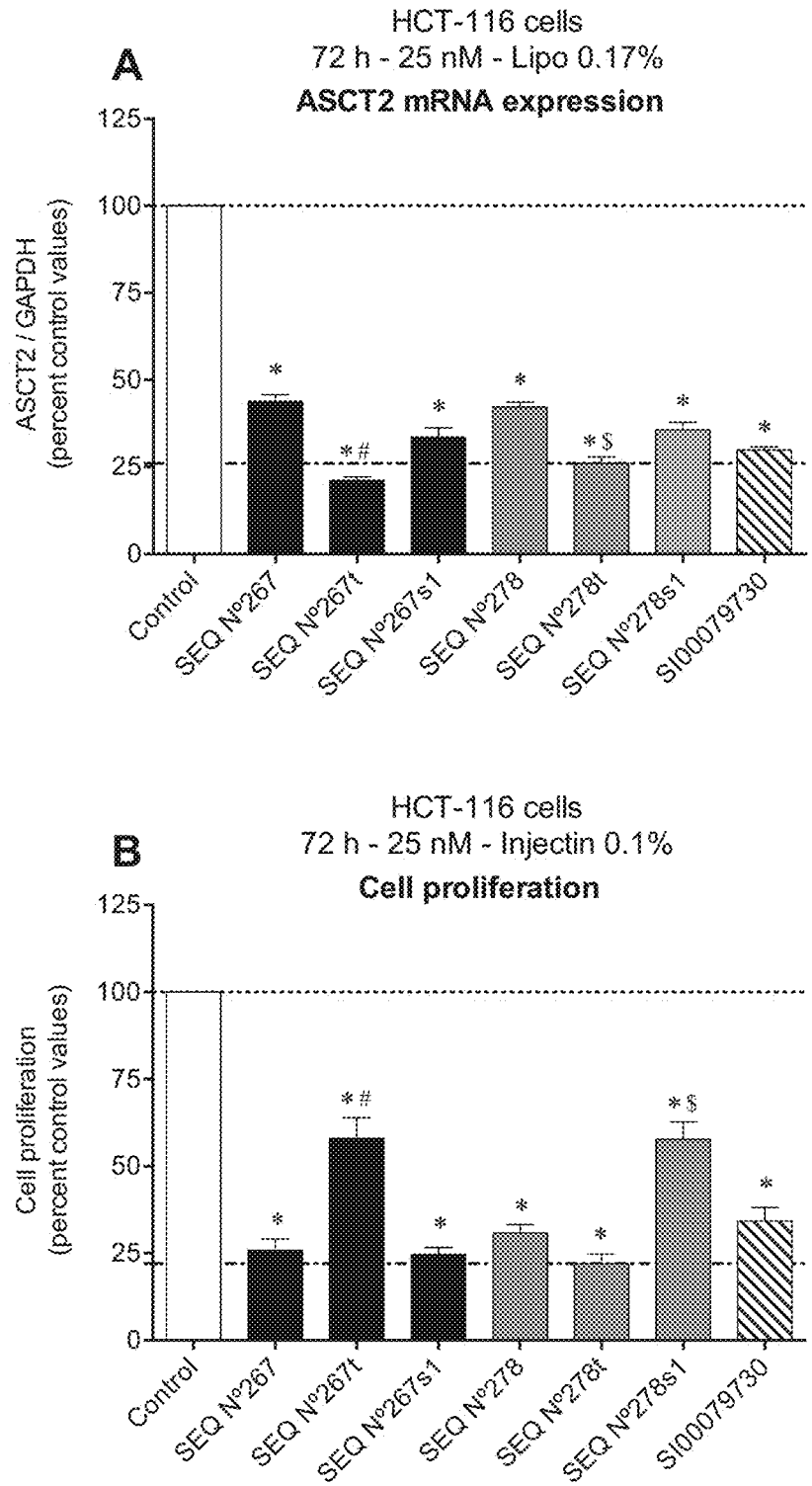

FIG. 20. Effects of anti-ASCT2 SEQ ID NOS 267/356/402, 267/397/398, 267/399/400, 278/367/408, 278/403/404, 278/405/406 and one commercially available siRNA (SI00097930, from QIAGEN) upon (A) ASCT2 mRNA relative abundance and (B) upon proliferation of human colon cancer HTC-116 cells at 72 h exposure times using 0.17% Lipofectamine 2000® or 0.1% Injectin® as the transfecting agent. Significantly different from corresponding control values (*p<0.01), values for SEQ ID NO: 267 (# p<0.05) and values for SEQ ID NO: 278 ($ p<0.05).

Figure 21:
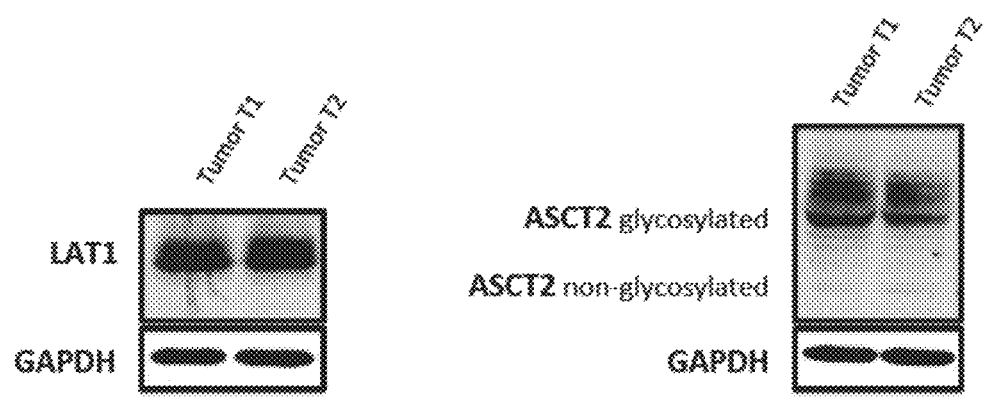

FIG. 21. Representative western blot of LAT1 and ASCT2 proteins in the xenograft tumour model developed in immune deficient mice injected subcutaneously with human colon cancer HTC-116 cells.

Figure 22:
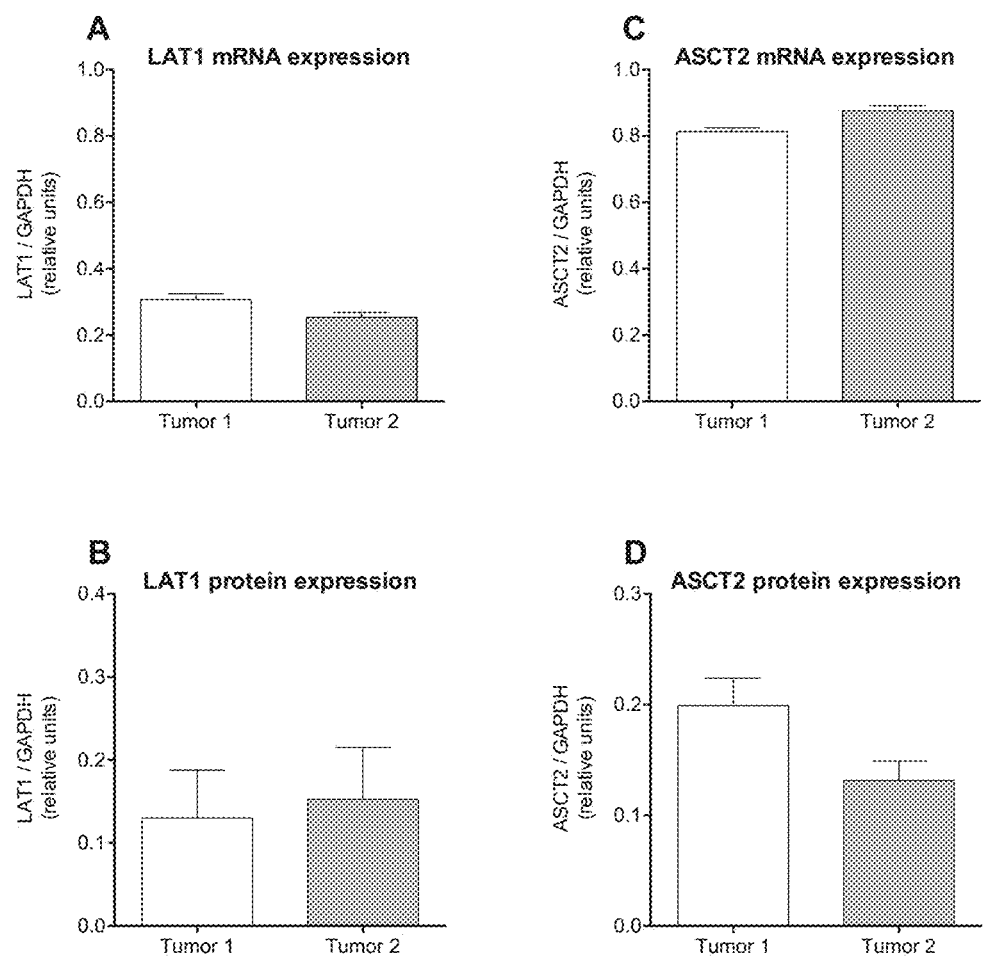

FIG. 22. Relative abundance of LAT1 mRNA and ASCT2 mRNA by RT-PCR (relative to GAPDH) and relative abundance of LAT1 protein and ASCT2 protein by western blot (relative to GAPDH) in the xenograft tumour model developed in immune deficient mice injected subcutaneously with human colon cancer HTC-116 cells.

Figure 23:
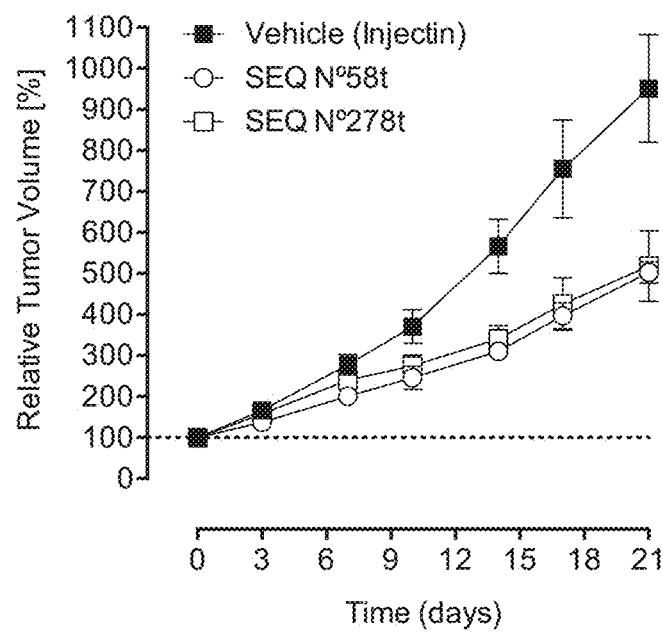

FIG. 23. Relative tumour volume in the xenograft tumour model developed in immune deficient mice injected subcutaneously with human colon cancer HTC-116 cells and treated every other day with intratumoral injections (50 µL) of vehicle (Injectin®) or anti-LAT1 SEQ ID NO: 58/387/388 (10 µg) and anti-ASCT2 SEQ ID NO: 278/403/404 (10 µg). The reduction in relative tumor volume induced by SEQ ID NO: 58/387/388 and SEQ ID NO: 278/403/404 was statistically significant with p values of 0.0018 and 0.0051, respectively.

FIG. 24. Table of LAT1 preferred target sequences.

FIG. 25. Table of ASCT2 preferred target sequences.

FIGS. 26A-D. Table of LAT 1 target sequences and siRNA. Figure discloses 5' anti-sense sequences as SEQ ID NOS 413-516, respectively, in order of appearance.

FIGS. 27A-C. Table of ASCT2 target sequences and siRNA. Figure discloses 5' anti-sense sequences as SEQ ID NOS 517-605, respectively, in order of appearance.

MATERIALS AND METHODS

Cell Culture

SK-HEP-1, T24, HT-1080 and HCT-116 cell lines were maintained in a humidified atmosphere of 5% $CO_2$ at 37° C. SK-HEP-1 cells were grown in RPMI-1640 (Sigma, St. Louis, Mo.) supplemented with 20% fetal bovine serum (FBS) (Gibco, UK), 100 U/mL penicillin G, 0.25 µg/mL amphotericin B, 100 µg/mL streptomycin (Gibco, UK), 25 mM sodium bicarbonate (Merck, Germany) and 25 mM N-2-hydroxyethylpiperazine-N'-2-ethanosulfonic acid (HEPES) (Sigma, St. Louis, Mo.). T24 and HT-1080 cells were grown, respectively, in Dulbecco's Modified Eagle's Medium (DMEM)—high glucose (Sigma, St. Louis, Mo.) and DMEM—low glucose (Sigma, St. Louis, Mo.), supplemented with 10% FBS (Gibco, UK), 100 U/mL penicillin G, 0.25 µg/mL amphotericin B, 100 µg/mL streptomycin (Gibco, UK), 25 mM sodium bicarbonate (Merck, Germany) and 25 mM HEPES (Sigma, St. Louis, Mo.). HCT-116 cells were grown in McCoy's 5A (Sigma, St. Louis, Mo.) supplemented with 10% FBS (Gibco, UK), 100 U/mL penicillin G, 0.25 µg/mL amphotericin B, 100 µg/mL streptomycin (Gibco, UK), 25 mM sodium bicarbonate (Merck, Germany) and 25 mM HEPES (Sigma, St. Louis, Mo.). For all cell lines the medium was changed every 2 days, and cells reached confluence 3-4 days after initial seeding. For subculturing, cells were dissociated with 0.25% trypsin-ethylenediaminetetraacetic acid (EDTA) (Sigma, St. Louis, Mo.), split 1:15 or 1:20 and subcultured in a 21-cm$^2$ growth area (Sarstedt, Germany).

LAT1 and ASCT2 Protein Expression

Cells were rinsed twice with cold phosphate-buffered saline (PBS) and incubated with 100 µL RIPA lysis buffer (154 mM NaCl, 65.2 mM TRIZMA base, 1 mM EDTA, 1% NP-40 (IGEPAL), 6 mM sodium deoxycholate) containing protease inhibitors: 1 mM PMSF, 1 µg/mL leupeptine and 1 µg/mL aprotinin; and phosphatase inhibitors: 1 mM $Na_3VO_4$ and 1 mM NaF. Cells were scraped and briefly sonicated. Equal amounts of total protein (30 µg) were separated on a 10% SDS-polyacrylamide gel and electrotransferred to a nitrocellulose membrane in Tris-Glycine transfer buffer containing 20% methanol. The transblot sheets were blocked in 5% non-fat dry milk in Tris-buffered saline (TBS) for 60 min and then incubated overnight, at 4° C., with the following antibodies: rabbit anti-LAT1 (1:1000; Cell Signalling); rabbit anti-ASCT2 (1:1000; Cell Signalling); or mouse monoclonal anti-GAPDH (1:20,000; Santa Cruz Biotechnology Inc.), diluted in 2.5% non-fat dry milk in TBS-Tween 20 (0.1% vol/vol). The immunoblots were subsequently washed and incubated with fluorescently-labelled goat anti-rabbit (1:20,000; IRDye™ 800, Rockland) or fluorescently-labelled goat anti-mouse secondary antibody (1:20,000; AlexaFluor 680, Molecular Probes) for 60 min at room temperature (RT) and protected from light. Membranes were washed and imaged by scanning at both 700 nm and 800 nm with an Odyssey Infrared Imaging System (LI-COR Biosciences).

LAT1 and ASCT2 Gene Expression

Total RNA was isolated and purified using the SV Total RNA Isolation System (Promega, USA) according to manufacturer's instructions. RNA quality and concentration were verified in the NanoDrop ND1000 Spectrophotometer (Thermo Scientific, USA), and RNA integrity and genomic DNA contamination were evaluated by agarose gel electrophoresis. Total RNA (1 µg) was converted into cDNA using the Maxima Scientific First Strand cDNA Synthesis Kit for RT-qPCR (Thermo Scientific, USA), according to instructions. The following protocol was used: $1^{st}$ step, 10 min at 25° C.; $2^{nd}$ step, 15 min at 50° C.; $3^{rd}$ step, 5 min at 85° C. cDNA was used for qPCR analysis using Maxima SYBR Green qPCR Master Mix (Thermo Scientific, USA) in the StepOnePlus instrument (Applied Biosystems, USA). QuantiTect Primer Assay for LAT1 and ASCT2 and for the endogenous control gene GAPDH (Quiagen, Germany) were used. The qPCR reaction was performed in 96-well PCR plates (Sarstedt, Germany) as follows: one cycle of 10 min at 95° C., followed by 40 PCR cycles at 95° C. 15 s and 60° C. 60 s. A melting curve was made immediately after the qPCR, to demonstrate the specificity of the amplification. No template controls were always evaluated for each target gene. Quantification cycle (Cq) values were generated automatically by the StepOnePlus 2.3 Software and the ratio of the target gene was expressed in comparison to the endogenous control gene GAPDH. Real-time PCR efficiencies were found to be between 90% and 110%.

LAT1 Activity

Cells were plated in 24-well plates (Sarstedt, Germany) and grown until confluence was reached. On the day of the experiment, cell culture medium was aspirated and cells were preincubated for 15 min in Hanks' medium (NaCl 140 mM, KCl 5 mM, $MgSO_4.7H_2O$ 0.8 mM, $K_2HPO_4$ 0.33 mM, $KH_2PO_4$ 0.44 mM, $MgCl_2.6H_2O$ 1 mM, $CaCl_2$) 0.025 mM, Tris-HCl 9.75 mM, pH 7.4). Uptake was initiated by addition of Hanks' medium with 0.25 µM [$^{14}C$]-L-leucine in the absence and in the presence of 3 mM unlabeled L-leucine. During preincubation and incubation cells were continuously shaken and maintained at 37° C. Uptake was terminated after 1 min by rapid removal of uptake solution by means of a vacuum pump connected to a Pasteur pipette, followed by a rapid wash with Hanks' medium. Subsequently, cells were solubilized in 0.1% vol/vol Triton X-100 (dissolved in 5 mM Tris-HCl, pH 7.4), and radioactivity was measured by liquid scintillation counting.

ASCT2 Activity

Cells were plated in 24-well plates (Sarstedt, Germany) and grown until confluence was reached. On the day of the experiment, Cell culture medium was aspirated and cells were preincubated for 15 min in Hanks' medium (ChCl 140 mM, KCl 5 mM, $MgSO_4.7H_2O$ 0.8 mM, $K_2HPO_4$ 0.33 mM, $KH_2PO_4$ 0.44 mM, $MgCl_2 \cdot 6H_2O$ 1 mM, $CaCl_2$) 0.025 mM, Tris-HCl 9.75 mM, pH 7.4). Uptake was initiated by the addition of Hanks' medium with 0.25 µM [$^{14}$C]-L-alanine in the absence and in the presence of 3 mM unlabeled L-alanin. During preincubation and incubation cells were continuously shaken and maintained at 37° C. Uptake was terminated after 1 min by rapid removal of uptake solution by means of a vacuum pump connected to a Pasteur pipette, followed by a rapid wash with Hanks' medium. Subsequently, cells were solubilized in 0.1% vol/vol Triton X-100 (dissolved in 5 mM Tris-HCl, pH 7.4), and radioactivity was measured by liquid scintillation counting.

LAT1 Gene Silencing

Cells were plated in 24-well (Sarstedt, Germany) or 6-well plates (Sarstedt, Germany) or 96-well plates with black walls clear bottom (BD Biosciences, USA) and incubated 24 h under normal growth conditions. siRNAs against LAT1 and transfection agent were diluted at desired concentrations and mixed according to transfection agent manufacturer's instructions. The mixture was incubated 20 min at RT for siRNA-complex formation, after which it was added to the cells and incubated at 37° C., 5% $CO_2$. After the incubation period, serum and antibiotic was restored and cells were further incubated at normal conditions for the desired time points until evaluation of LAT1 activity or LAT1 expression (immunoblotting and RT-qPCR).

ASCT2 Gene Silencing

Cells were plated in 24-well (Sarstedt, Germany) or 6-well plates (Sarstedt, Germany) or 96-well plates with black walls clear bottom (BD Biosciences, USA) and incubated 24 h under normal growth conditions. siRNAs against ASCT2 and transfection agent were diluted at desired concentrations and mixed according to transfection agent manufacturer's instructions. The mixture was incubated 20 min at RT for siRNA-complex formation, after which it was added to the cells and incubated at 37° C., 5% $CO_2$. After the incubation period, serum and antibiotic was restored and cells were further incubated at normal conditions for the desired time points until evaluation of ASCT2 activity or ASCT2 expression (immunoblotting and RT-qPCR).

Cell Proliferation Assay

Cell proliferation was measured using calcein-AM (Thermo Fisher Scientific, USA). The membrane permeant calcein-AM, a nonfluorescent dye, is taken up and converted by intracellular esterases to membrane impermeant calcein, which emits green fluorescence. Cells were plated in 96-well plates with black walls clear bottom (BD Biosciences, USA) and incubated 24 h under normal growth conditions. Cells were incubated with test items at 37° C., 5% C02. After the incubation period, serum and antibiotic was restored and cells were further incubated at normal conditions during 72 h. After treatment with test substances or vehicle, cells were washed twice with Hanks' medium and loaded with 2 µM calcein-AM in Hanks' medium, at at 37° C. for 30 min. Fluorescence was measured at 485 nm excitation and 530 nm emission wavelengths in a microplate spectrofluorometer (Gemini EM, Molecular Devices). Nine consecutive fluorescence measurements are performed per well, to allow fluorescence readings in the whole area of the well, which was then considered for the calculation of mean fluorescence per well. To determine minimum staining for calcein (calceinmin), eight wells were treated with ethanol 30 min before calcein-AM addition. The percent cell number is calculated as [($calcein_{sample}$)/($calcein_{control}$)]×100.

Animals and Tumour Implantation

Human colon cancer HTC-116 cells grown in tissue culture and $10^7$ cells per mouse were injected into the hind flank of female NMRI nu/nu mice. Once tumours have developed and tumour volumes reached randomisation criteria, therapy will commence by every other day daily, intra-tumoral injections. A vehicle treated group was included in the study as control. Female immunodeficient NMRI nu/nu mice from Charles River were used. The animals were delivered at the age of 4-6 weeks and are used for implantation after at least 1 week of quarantine. All animals interventions were performed in accordance with the European Directive number 86/609, and the rules of the "Guide for the Care and Use of Laboratory Animals", 7th edition, 1996, Institute for Laboratory Animal Research (ILAR), Washington, D.C. Only animals with unobjectionable health were selected to enter testing procedures. During the experiments, animals were monitored at least daily. Each cage was labelled with a record card indicating animal source, gender, and the delivery date. Animals were numbered during tumour implantation or at the initiation of a dose finding experiment.

The tumour volume was determined by a two-dimensional measurement with callipers on the day of randomization (Day 0) and then twice weekly. Tumour volumes were calculated according to the following equation:

$$\text{Tumour Vol } [mm^3] = a\,[mm] \times b^2\,[mm^2] \times 0.5$$

where "a" is the largest diameter and "b" is the perpendicular diameter of the tumour representing an idealized ellipsoid.

The relative volume of an individual tumour on day X ($RTV_x$) was calculated by dividing the absolute volume [$mm^3$] of the respective tumour on day X ($T_x$) by the absolute volume of the same tumour on the day of randomization, i. e. on day 0 ($T_0$), multiplied by 100, as shown by the following equation:

$$RTV_x[\%] = \frac{T_x}{T_0} \times 100$$

RTVs were used for growth characterization and compound activity rating as follows:

| Rating | | $RTV_x$ [%] |
| --- | --- | --- |
| CR | Complete remission | ≤10 |
| PR | Partial remission | >10; ≤50 |
| MR | Minor remission | >50; ≤75 |
| NC | No change | >75; ≤125 |
| P | Progression | >125 |

Group median and range (alternatively geometric mean+/−SEM) of RTVs were calculated, considering only the tumours of animals that were alive on the day in question (for median). Group median (geometric mean) RTVs were used for drawing tumour growth curves and for treatment evaluation.

Tumour inhibition on a particular day ($T/C_x$) was calculated from the median RTV of a test group and the median RTV of a control group multiplied by 100, as shown by the following equation:

$$T/C_x[\%] = \frac{\text{median } RTV_x \text{ treated group}}{\text{median } RTV_x \text{ control group}} \times 100$$

The optimum/minimum/best T/C [%] value recorded for a particular group during an experiment represents the maximum anti-tumour activity for the respective treatment and is rated as follows:

| Rating | | T/C [%] |
|---|---|---|
| − | Inactive | ≥65 |
| +/− | Borderline activity | ≥50; ≤65 |
| + | Moderate activity | ≥25; ≤50 |
| ++ | High activity | ≥10; ≤25 |
| +++ | Very high activity | ≥5; ≤10 |
| ++++ | Complete remission | <5 |

Tumour volume doubling/quadrupling time (DT/QT) is defined as the time interval (in days) required for a group to reach a median RTV of 200%/400% of the initial tumour volume. Growth delay is defined as the difference in days between the tumour volume doubling and quadrupling times of a test group and the respective control group.

Non-Viral Delivery siRNA Systems

1. Liposomes carrying therapeutic siRNA-LAT1 agents are capable of passing through the membrane of the target cell to deliver cargo. A large number of lipids can be used for the synthesis of liposomes used for the delivery of siRNAs. Neutral lipids that can be complexed with siRNA-LAT1 include DOPE (1,2-dioleoyl-sn-glycerol-3-phosphoethanolamine), egg PC (phosphatidylcholine), DOPC (1,2-dioleoyl-sn-glycero-3-phosphatidylcholine and DPPE (1,2-dipalmitoyl-sn-glycero-3-phosphoethanolamine).

2. Cationic lipids that can be complexed with siRNA-LAT1 include DOTAP (1,2-dioley-3-trimetylammonium propane), CDAN (N(1)-cholesteryloxycarbonyl-3,7-diazanonane-1,9-diamine)/DOPE, DC-Chol (3β-[N—(N',N'-dimethylaminoethane)carbamoyl] cholesterol)/DOPE, DOTAP/DOPE, cationic lipid RPR209120 (2-(3-[Bis-(3-amino-propyl)-amino]-propylamino)-N-ditetradecylcarbamoylme-thyl-acetamide). Galactosylated (Gal-C4-Chol/DOPE) liposomes/siRNA-LAT1 complex can also induce gene silencing.

3. Cationic polymers can also be used in siRNA-LAT1 or siRNA-ASCT2 delivery. These materials combine with anionic siRNA-LAT1 or siRNA-ASCT2 to form a siRNA-LAT1-polymer complex or siRNA-ASCT2-polymer complex that can interact with the negatively charged cell surfaces through the cationic portion of the complex. Among the available polymers, polyethyleneimine (PEI) has the ability to bind strongly to negatively charged siRNA-LAT1 or siRNA-ASCT2. Biodegradable polymers such as poly(L-lysine) (PLL) are known for their lower toxicity and higher biocompatibility than PEI. A derivative of PLL, poly[a-(4-aminobutyl)-L-glycolic acid] exhibits higher transfection efficiency and lower immunogenicity and cytotoxicity than the original PLL polymer and can be used with siRNA-LAT1 or siRNA-ASCT2.

4. Cationized gelatin microspheres can be prepared by chemically cross-linking gelatin in the water-in-oil emulsion state. To impregnate siRNA-LAT1 or siRNA-ASCT2 expression plasmid DNA into cationized gelatin microspheres, PBS containing siRNA-LAT1 expression plasmid DNA can be dropped onto freeze-dried cationized gelatin microspheres and then kept for 24 h at 4° C.

5. Nanoparticles can be produced based on modified ionic gelation of tripolyphosphate (TPP) with chitosan. Two different types of chitosan (chitosan hydrochloride and glutamate) and each type with two different molecular weights can be used. Nanoparticles can be spontaneously obtained upon the addition of a TPP aqueous solution to chitosan solution under constant magnetic stirring at room temperature. The particles can then be incubated at room temperature for before use or further analysis. Nanoparticles are collected by centrifugation. The supernatants are discarded and nanoparticles are resuspended in filtered distilled water. For the association of siRNA-LAT1 or siRNA-ASCT2 with the chitosan-TPP nanoparticles (chitosan-TPP-siRNA-LAT1 or chitosan-TPP-siRNA-ASCT2), siRNA-LAT1 or siRNA-ASCT2 in double distilled water is added to the TPP solution before adding this drop-wise to the chitosan solution under constant magnetic stirring at room temperature. The particles are then incubated at room temperature before use or further analysis.

6. Chitosan (114 kDa) was dissolved in sodium acetate buffer to obtain a 0.2-1 mg/ml working solution range. Twenty microliters of siRNA-LAT1 or siRNA-ASCT2 (20-250 µm range) was added to 1 ml of filtered chitosan while stirring and left for 1 h. To calculate specific N:P ratios (defined as the molar ratio of chitosan amino groups/RNA phosphate groups) a mass per phosphate of 325 Da was used for RNA and mass per charge of 167.88 for chitosan (84% deacetylation).

7. The siRNA-LAT1 or siRNA-ASCT2 can be encapsulated in stable nucleic acid lipid particles (SNALP) and administered by intravenous injection. The SNALP formulation contained the lipids 3-N-[(ω-methoxypoly(ethylene glycol)$_{2000}$)carbamoyl]-1,2-dimyristyloxy-propylamine (PEG-DMA), 1,2-dilinoleyloxy-N,N-dimethyl-3-qminopropanone (DLinDMA), 1,2-distearoyl-sn-glycero-3-phosphocholine (DSPC) and cholesterol.

8. The siRNA-LAT1 or siRNA-ASCT2 can be encapsulated in Injectin In Vivo SiRNa Delivery Reagent (BioCell-Challenge SAS, Toulon, France) and administered by intravenous injection. The Injection formulation contained the following mixture: 10 µg of siRNA in 10 µL of glucose containing buffer, 40 µL with a sterile RNase-free water, 10 µL of Injectin reagent. The mixture should be mix by pipetting up and down and incubated 15 minutes at room temperature before injection.

Example 1

LAT1 and ASCT2 Immunoblotting in Human Cancer Cells

The presence of LAT1 protein and ASCT2 was studied by means of immunoblotting using an antibodies raised against LAT1 and ASCT2. As shown in FIG. 1, the antibody raised against LAT1 and ASCT2 recognized the presence of LAT1 and ASCT2 in all cancer cell lines.

Example 2

LAT1 and ASCT2 Gene Expression in Human Cancer Cells

Figure 2:
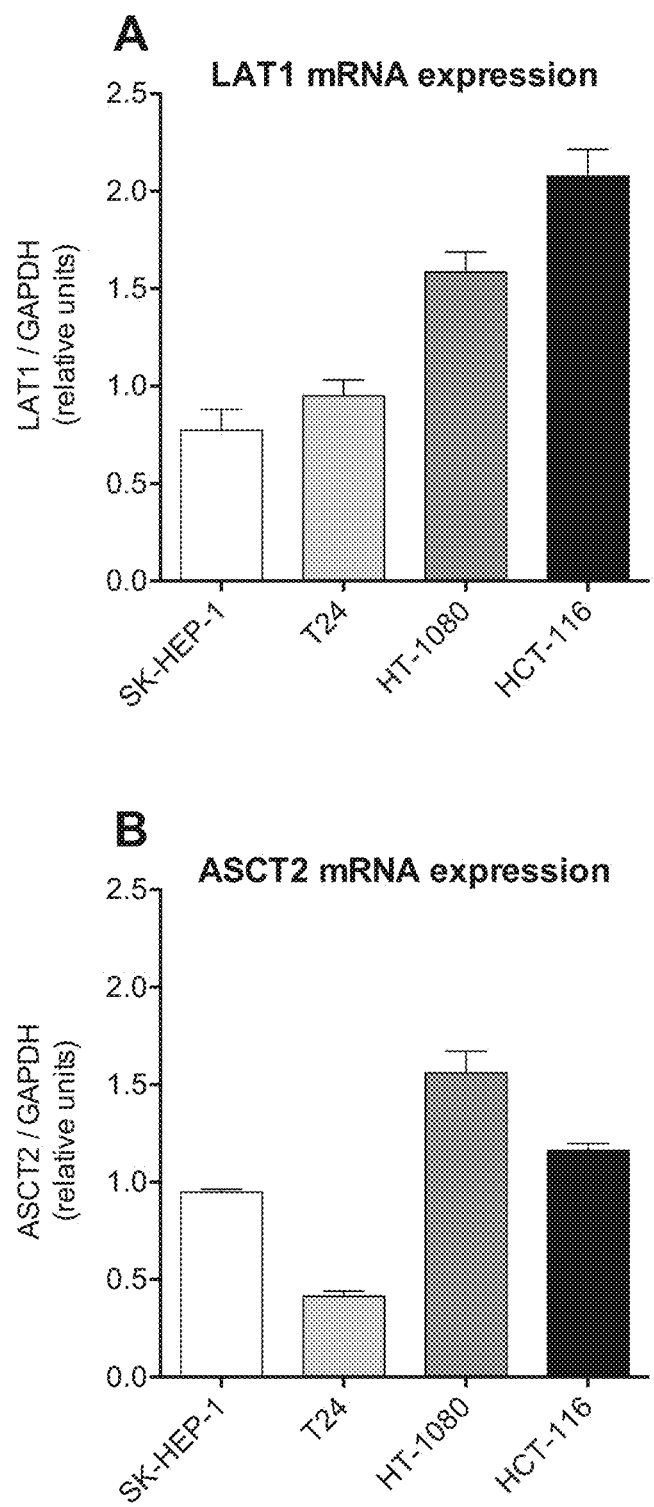
FIG. 2. Relative abundance of LAT1 mRNA and ASCT2 mRNA in in human liver carcinoma SK-HEP-1 cells, human bladder carcinoma T24 cells, human fibrosarcoma HT-1080 cells and human colon cancer HTC-116 cells by RT-PCR (relative to GAPDH).
Figure 3:
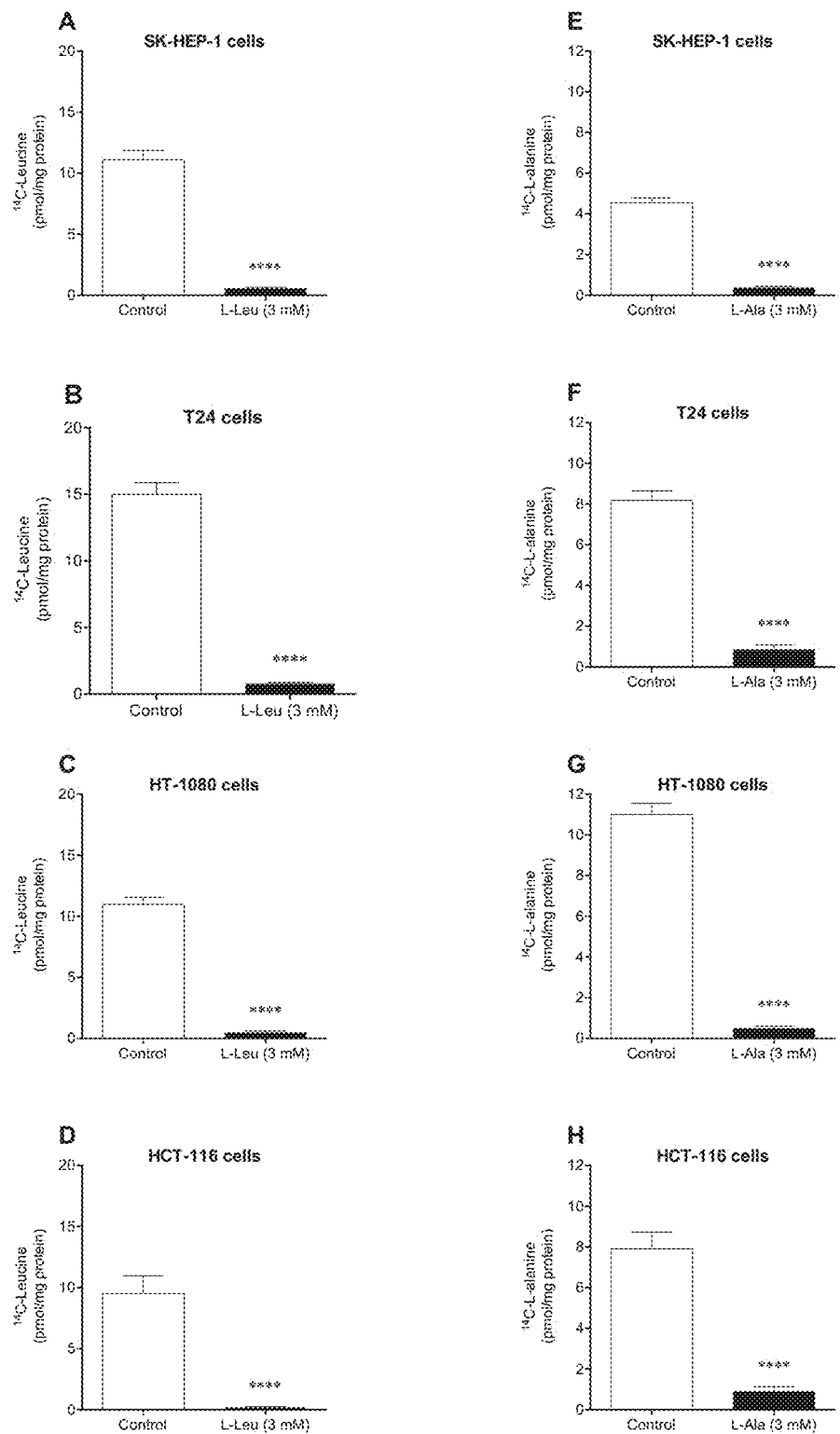
FIG. 3. Transport of $^{14}$C-L-leucine through LAT1 (sensitive to unlabelled L-leucine) and the transport of $^{14}$C-L-alanine through ASCT2 (sensitive to unlabelled L-alanine). Significantly different from corresponding control values (****$p<0.001$).

The presence of LAT1 and ASCT2 mRNA was studied by means of Real-time PCR using primers against ASCT2. As shown in FIG. 2, LAT1 and ASCT2 gene expression relative to the house keeping gene GADPH was found in all cancer cell lines.

Example 3

[$^4$C]-L-Leucine and [$^{14}$C]-L-Alanine Uptake

Sodium-independent [$^{14}$C]-L-leucine (0.25 µM) uptake at initial rate of uptake (1 min) in epithelial carcinoma cells was significantly (P<0.001) reduced by 3 mM unlabelled L-leucine as shown in FIGS. 3A-3D. Sodium-dependent [$^{14}$C]-L-alanine (0.25 μM) uptake at initial rate of uptake (1 min) in epithelial carcinoma cells was significantly (P<0.01) reduced by 3 mM unlabelled L-alanine, as shown in FIGS. 3E-3H.

Example 4

LAT1 and ASCT2 Gene Expression in Human Cancer Cells

Figure 4:
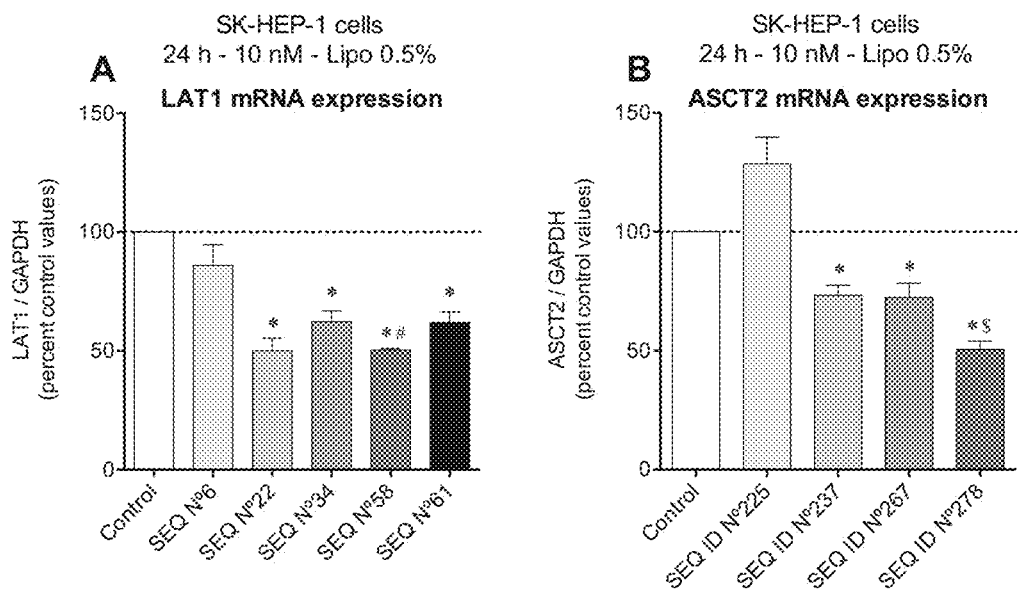
FIG. 4. LAT1 mRNA relative abundance in liver carcinoma SK-HEP-1 cells treated for 24 h with 10 nM siRNA-LAT1 (A) against nucleotide SEQ ID NO: 6, 22, 34, 58 and 61 and (B) ASCT2 mRNA relative abundance in liver carcinoma SK-HEP-1 cells treated for 6 h with 10 nM siRNA-ASCT2 against nucleotide SEQ ID NO: 225, 237, 267 and 278 on ASCT2 mRNA levels in human cancer cells (SK-HEP-1) using 0.5% Lipofectamine 2000 as the transfecting agent at 24 h. Significantly different from corresponding control values (*$p<0.01$) and values for SEQ ID NO: 34 (# $p<0.05$).

As shown in FIG. 4A, treatment for 6 h of cells with the siRNA-LAT1 against nucleotide SEQ ID NOS 6, 22, 34, 58 and 61 (for example, an siRNA comprising or consisting of SEQ ID NO: 110, 126, 138, 162 and 165 respectively) decreased LAT1 mRNA relative abundance in liver carcinoma SK-HEP-1 cells at 24 h. The effects siRNA-LAT1 against nucleotide SEQ ID NO: 58 were significantly greater (p<0.05) than those with SEQ ID NO: 34. As shown in FIG. 4B, treatment for 6 h of cells with the siRNA-ASCT2 against nucleotide SEQ ID NOS 225, 237, 267 and 278 (for example, an siRNA comprising or consisting of SEQ ID NO: 314, 326, 356 and 367 decreased ASCT2 mRNA relative abundance in liver carcinoma SK-HEP-1 cells at 24 h. The effects siRNA-ASCT2 against nucleotide SEQ ID NO: 278 were significantly greater (p<0.05) than those with SEQ ID NO: 267.

Example 5

[$^{14}$C]-L-Leucine and [$^{14}$C]-L-Alanine Uptake

Figure 5:
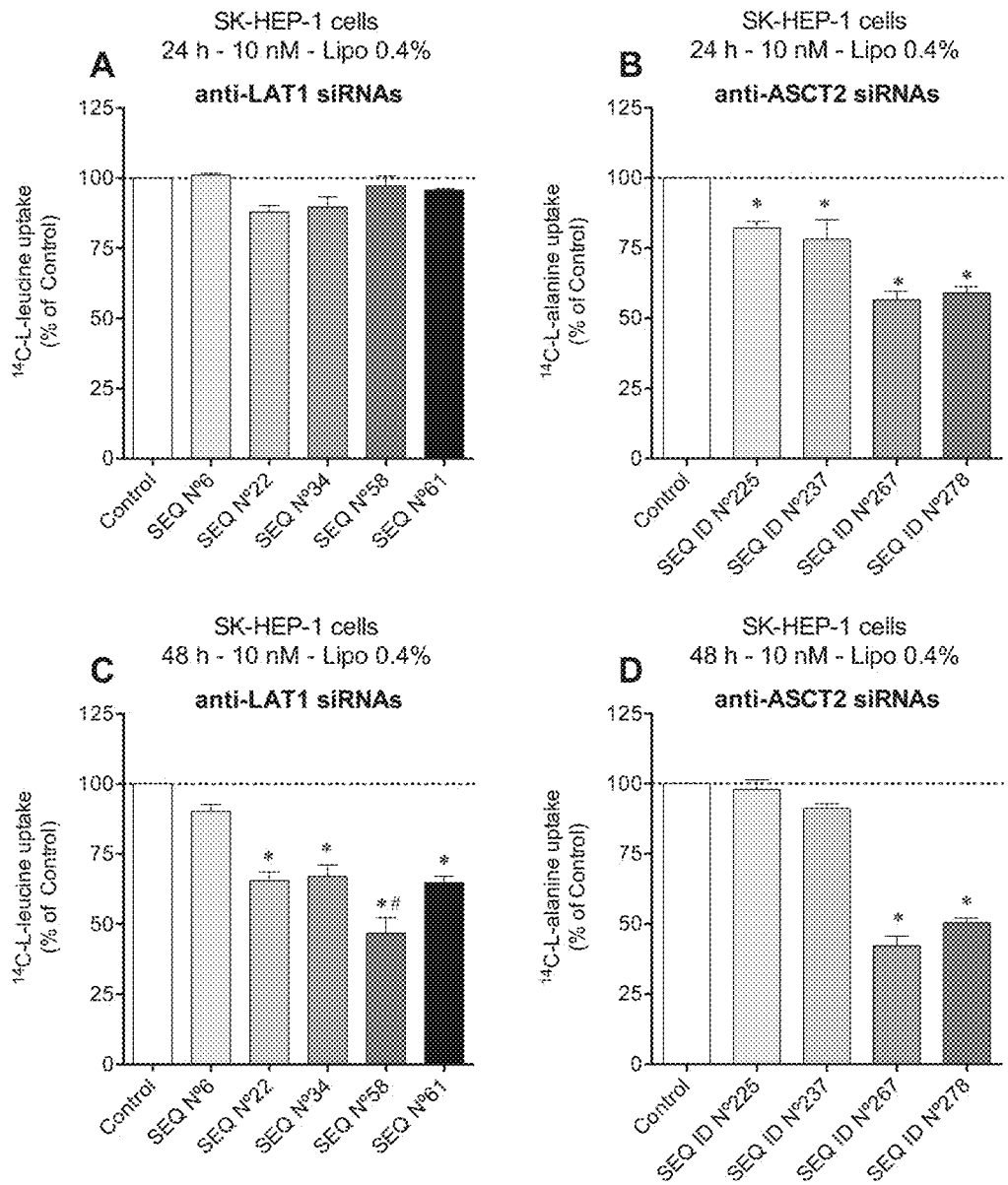
FIG. 5. [$^{14}$C]-L-leucine (0.25 µM) (A and C) and [$^{14}$C]-L-alanine (0.25 µM) (B and D) uptake at initial rate of uptake (1 min) in liver carcinoma SK-HEP-1 cells treated for 6 h with 10 nM siRNA-LAT1 (A and C) against nucleotide SEQ ID NO: 6, 22, 34, 58 and 61 anti-LAT1 against nucleotide SEQ ID NOS 6, 22, 34, 58 and 61 (A and C) and SEQ ID NO: 6, 22, 34, 58 and 61 on and 10 nM siRNA-ASCT2 against nucleotide SEQ ID NO: 225, 237, 267 and 278 using 0.4% Lipofectamine 2000 as the transfecting agent at 24 h (A and B) or 48 h (C and D). Significantly different from corresponding control values (*$p<0.01$), values for SEQ ID NO: 34 (# $p<0.05$) and values for SEQ ID NO: 267 ($ $p<0.05$).

As shown in FIGS. 5A and 5C, treatment for 6 h of cells with the siRNA-LAT1 against nucleotide SEQ ID NOS 6, 22, 34, 58 and 61 (for example, an siRNA comprising or consisting of SEQ ID NO: 110, 126, 138, 162 and 165 respectively) decreased [$^{14}$C]-L-leucine (0.25 μM) uptake at initial rate of uptake (1 min) in liver carcinoma SK-HEP-1 cells at 24 h and 48 h. The effects siRNA-LAT1 against nucleotide SEQ ID NO: 58 were significantly greater (p<0.05) than those with SEQ ID NO: 34. As shown in FIGS. 5B and 5D, treatment for 6 h of cells with the siRNA-ASCT2 against nucleotide SEQ ID NOS 225, 237, 267 and 278 (for example, an siRNA comprising or consisting of SEQ ID NO: 314, 326, 356 and 367 for 24 h [$^{14}$C]-L-leucine (0.25 μM) uptake at initial rate of uptake (1 min) in liver carcinoma SK-HEP-1 cells at 24 h and 48 h.

Example 6

Modifications of siRNA-LA T1 and siRNA-ASCT2 siRNA-LAT1 against nucleotide SEQ ID NOS 58 and 61 (for example, an siRNA comprising or consisting of SEQ ID NO: 162 and 165 respectively) are shown in FIG. 6. (5' DNA sense, 5' sense siRNA and 3' antisense siRNA-LAT1 against nucleotide SEQ ID NOS 58/162/411, 58/387/388, 58/389/390, 58/389/412, 61/165/396, 61/391/392, 61/393/394 and 61/395/396). siRNA-ASCT2 against nucleotide SEQ ID NOS 267 and 278 (for example, an siRNA comprising or consisting of SEQ ID NO: 356 and 367 respectively) are shown in FIG. 7. 5' DNA sense, 5' sense siRNA and 3' antisense siRNA-ASCT2 against nucleotide SEQ ID NOS 267/356/402, 267/397/398, 267/399/400, 267/401/402, 278/367/408, 278/403/404, 278/405/406 and 278/407/408

Example 7

[$^{14}$C]-L-Leucine and [$^{14}$C]-L-Alanine Uptake

As shown in FIG. 8A, treatment for 6 h of cells with the siRNA-LAT1 against nucleotide SEQ ID NOS 58/162/411, 61/165/396, 58/387/388, 61/391/392 as described herein and the commercially available SI31011000 decreased [$^{14}$C]-L-leucine (0.25 μM) uptake at initial rate of uptake (1 min) in fibrosarcoma HT-1080 cells at 48 h. As shown in FIG. 8B, treatment for 6 h of cells with the siRNA-ASCT2 against nucleotide SEQ ID NOS 267/356/402, 278/367/408, 267/397/398 and 278/403/404 (for example, an siRNA comprising or consisting of SEQ ID NO: 356, 367 or an siRNA comprising or consisting of SEQ ID NO: 399 as the sense strand and SEQ ID NO: 400 as the antisense strand or SEQ ID NO: 405 as the sense strand and SEQ ID NO: 406 as the antisense strand respectively) and the commercially available SI00097930 decreased [$^{14}$C]-L-alanine (0.25 μM) uptake at initial rate of uptake (1 min) in fibrosarcoma HT-1080 cells at 48 h. The effects siRNA-ASCT2 against nucleotide SEQ ID NO: 278/403/404 were significantly greater (p<0.05) than those with SEQ ID NO: 267/397/398.

Example 8

LAT1 and ASCT2 Gene Expression in Human Cancer Cells

As shown in FIGS. 9A and 9C, treatment for 6 h of cells with the siRNA-LAT1 against nucleotide SEQ ID NOS 58/162/411, 61/165/396, 58/387/388 and 61/391/392 (for example, an siRNA comprising or consisting of SEQ ID NO: 162, 165, or an siRNA comprising or consisting of SEQ ID NO: 387 as the sense strand and SEQ ID NO: 388 as the antisense strand or SEQ ID NO: 393 as the sense strand and SEQ ID NO: 394 as the antisense strand respectively) decreased LAT1 mRNA relative abundance in human colon cancer HTC-116 cells at 24 h or 48 h. As shown in FIGS. 9B and 9C, treatment for 6 h of cells with the siRNA-ASCT2 against nucleotide SEQ ID NOS 267/356/402, 278/367/408, 267/397/398 and 278/403/404 (for example, an siRNA comprising or consisting of SEQ ID NO: 356, 367, or an siRNA comprising or consisting of SEQ ID NO: 399 as the sense strand and SEQ ID NO: 400 as the antisense strand or SEQ ID NO: 405 as the sense strand and SEQ ID NO: 406 as the antisense strand respectively) decreased ASCT2 mRNA relative abundance in human colon cancer HTC-116 cells at 24 h or 48 h.

Example 9

LAT1 Gene Expression in Human Cancer Cells

As shown in FIGS. 10A and 10B, treatment for 6 h of cells with the siRNA-LAT1 against nucleotide SEQ ID NO: 58/387/388 (for example, an siRNA comprising or consisting of SEQ ID NO: 387 as the sense strand and SEQ ID NO: 388 as the antisense strand) decreased LAT1 mRNA relative abundance in human colon cancer HTC-116 cells in a concentration dependent manner and when using 0.5% Lipofectamine 2000®, Lipofectamine RNAiMAX® or Injectin® as the transfecting agents at 72 h.

Example 10

Cell Proliferation of Human Colon Cancer HTC-116 Cells, Transfection Agents and Negative Controls As shown in FIG. 11A, treatment for 6 h of human colon cancer HTC-116 cells with 0.5% Lipofectamine 2000® for 72 h did not affect cell proliferation. By contrast, treatment of human colon cancer HTC-116 cells with Injectin® did affect cell proliferation at 72 h in a statistically significant manner at 0.1%, 0.113 and 0.115%, as shown in FIG. 11B. Injectin is a lipid based siRNA transfection agent. Manufacture instructions recommend the use of 1 μg of siRNA per μL of Injectin® reagent (ratio 1:1) where the volume of Injectin reagent corresponds to 20% of the total complex mixture. For in vivo assays, siRNA:Injectin® complexes were prepared exactly as recommended by the producer. For in vitro assays, the siRNA concentration used was downscaled and therefore the maintenance of 20% of Injectin® in the total siRNA:Injectin® complex mixture was unviable. For such a reason, siRNA complexation efficacy and siRNA:Injectin® transfection efficiency were evaluated using different percentages of Injectin® in the complex mixture. Electrophoresis of siRNA:Injectin® complexes revealed that siRNA is fully complexed when the siRNA:Injectin® ratio is 1:1 and the percentage of Injectin® in the complex mixture is higher than 0.9% (FIG. 12A). However, siRNA complexation is not effective when the siRNA:Injectin® ratio 1:1 is maintained but the amount of Injectin® in the complex mixture is equal or lower than 0.2% (FIG. 12B). This data suggests that when the percentage of Injectin® in the complex is lower than 0.2% the recommended 1 μg of siRNA per μL of Injectin® ratio is no longer effective. Therefore, the amount of Injectin® per μg of siRNA needs to be increased in order to obtain a more efficient siRNA:Injectin® complex. Similarly, an increase in the amount of Injectin® in the complex mixture enhances the effect of siRNA sequences upon cell proliferation (FIG. 15), as evidence of the enhanced transfection efficiency of siRNA:Injectin® complexes with higher amounts of Injectin® in the siRNA transfection mixture. As shown in FIG. 13, negative control siRNA commercial (from QIAGEN) sequences NC-SI03650318 and NC-SI03650325 did not significantly affect the proliferation human colon cancer HTC-116 cells at 72 h exposure times using Injectin® (0.075 and 0.1%) or lipofectamine 2000 (0.25%) as the transfecting agent.

Example 11

Cell Proliferation of Human Colon Cancer HTC-116 Cells

As shown in FIG. 14A, treatment for 6 h of cells with the siRNA-LAT1 against nucleotide SEQ ID NOS 6, 22, 34, 58/162/411, 58/387/388, 58/389/390, 58/389/412, 61/165/396, 61/391/392, 61/393/394, 61/395/396 as described herein, and three commercially available siRNAs (SI31011000, HSS112005 and SASI_Hs01_00103513 respectively from QIAGEN, Thermofisher Scientific and Sigma-Aldrich) decreased cell proliferation at 72 h exposure times using 0.1% Injectin® as the transfecting agent. The effects siRNA-LAT1 against nucleotide SEQ ID NO: 58 were significantly greater (p<0.05) than those with SEQ ID NO: 34 and the effects of siRNA-LAT1 against nucleotide SEQ ID NOS 58/389/390 and 58/389/412 were significantly greater (p<0.05) than those with SEQ ID NO: 58. As shown in FIG. 14B, treatment for 6 h of cells with the siRNA-ASCT2 against nucleotide SEQ ID NOS 267/356/402, 267/397/398, 267/399/400, 267/401/402, 278/367/408, 278/403/404, 278/405/406, 278/407/408 as described herein, and one commercially available siRNA (SI00097930 from QIAGEN) decreased cell proliferation at 72 h exposure times using 0.1% Injectin® as the transfecting agent. The effects siRNA-ASCT2 against nucleotide SEQ ID NO: 267/397/398 and SEQ ID NO: 267/401/402 were significantly greater (p<0.05) than those with SEQ ID NO: 267/356/402 and the effects of siRNA-ASCT2 against nucleotide SEQ ID NO: 278/405/406 and SEQ ID NO: 278/407/408 were significantly greater (p<0.05) than those with SEQ ID NO: 278/367/408.

Treatment for 6 h of cells with the siRNA-LAT1 against nucleotide SEQ ID NO: 58/387/388 (for example, an siRNA comprising or consisting of SEQ ID NO: 387 as the sense strand and SEQ ID NO: 388 as the antisense strand), as shown in FIG. 15A, and siRNA-ASCT2 against nucleotide SEQ ID NOS 267/397/398 and 278/403/404 (for example, an siRNA comprising or consisting of SEQ ID NO: 399 as the sense strand and SEQ ID NO: 400 as the antisense strand or SEQ ID NO: 405 as the sense strand and SEQ ID NO: 406 as the antisense strand respectively), as shown in FIGS. 15B and 15C respectively, decreased cell proliferation at 72 h exposure times that was greater the higher the concentration Injectin® in the siRNA:Injectin® complexes. This was particularly evident with siRNA-LAT1 against nucleotide SEQ ID NO: 58/387/388 and siRNA-ASCT2 against nucleotide SEQ ID NO: 278/403/404.

Example 12

Cell Proliferation of Human Colon Cancer HTC-116 Cells in the Presence of Cytotoxic Antineoplastic Agents As shown in FIG. 16, the effects of the cytotoxic antineoplastic agents 5-fluorouracil (5-FU; 3 and 10 μM), cisplatin (Cisp; 3 and 10 μM) and oxaliplatin (Oxa; 1 and 3 μM) alone upon proliferation of human colon cancer HTC-116 cells at 72 h exposure times were all significantly enhanced in combination with the siRNA-LAT1 against nucleotide SEQ ID NO: 58/387/388, as described herein, in a concentration dependent manner. As shown in FIG. 17A, the effects of the cytotoxic antineoplastic agents 5-fluorouracil (5-FU; 10 μM) alone upon proliferation of human colon cancer HTC-116 cells at 72 h exposure times was enhanced by the siRNA-LAT1 against nucleotide SEQ ID NO: 58/387/388 as defined herein, but not by the siRNA-LAT1 against nucleotide SEQ ID NO: 61/391/392, as described herein. Similarly, as shown in FIG. 17B, the enhancement of effects by he cytotoxic antineoplastic agents 5-fluorouracil (5-FU; 10 μM) by the siRNA-ASCT2 against nucleotide SEQ ID NO: 278/403/404, as described herein, was more marked than that by the siRNA-ASCT2 against nucleotide SEQ ID NO: 267/397/398, as described herein.

Example 13

Cell Proliferation of Human Colon Cancer HTC-116 Cells in the Presence Anti-LA T1 and Anti-ASCT2 siRNAs As shown in FIG. 18A, the significant decrease upon proliferation of human colon cancer HTC-116 cells at 72 h exposure times by the siRNA-LAT1 against nucleotide SEQ ID NO: 58/387/388, as described herein, was enhanced by the siRNA-ASCT2 against nucleotide SEQ ID NO: 278/403/404, as described herein, at non-efficacious conditions (0.037% Injectin®). Similarly, as shown in FIG. 18B, the significant effects upon proliferation of human colon cancer HTC-116 cells at 72 h exposure times by the siRNA-LAT1 against nucleotide SEQ ID NO: 58/387/388, as described herein, was enhanced by the siRNA-ASCT2 against nucleotide SEQ ID NO: 267/397/398, as described herein, at non-efficacious conditions (0.037% Injectin®).

Example 14

LAT1 and ASCT2 Gene Expression and Cell Proliferation of Human Colon Cancer HTC-116 Cells in the Presence Anti-LAT1 and Anti-ASCT2 siRNAs As shown in FIG. 19A, treatment of cells with the siRNA-LAT1 against nucleotide SEQ ID NOS 58/162/411, 58/387/388, 58/389/390, 61/165/396, 61/391/392, 61/393/394 as described herein, and two commercially available siRNAs (SI31011000 and HSS112005, respectively from QIAGEN and Thermofisher Scientific) for 6 h significantly decreased LAT1 mRNA relative abundance in human colon cancer HTC-116 cells though evidently with siRNA-LAT1 against nucleotide SEQ ID NOS 58/387/388 and 58/389/390. As shown in FIG. 19B, treatment of cells with the siRNA-LAT1 against nucleotide SEQ ID NOS 58/162/411, 58/387/388, 58/389/390, 61/165/396, 61/391/392, 61/393/394, as described herein, and two commercially available siRNAs (SI31011000 and HSS112005, respectively from QIAGEN and Thermofisher Scientific) for 6 h significantly decreased proliferation of human colon cancer HTC-116 cells at 72 h, though evidently with siRNA-LAT1 against nucleotide SEQ ID NOS 58/162/411, 58/387/388 and 58/389/390.

As shown in FIG. 20A, treatment of cells with the siRNA-ASCT2 against nucleotide SEQ ID NOS 267/356/402, 267/397/398, 267/399/400, 278/367/408, 278/403/404, 278/405/406, as described herein, and one commercially available siRNAs (SI00097930 from QIAGEN) for 6 h significantly decreased ASCT2 mRNA relative abundance in human colon cancer HTC-116 cells though evidently with siRNA-LAT1 against nucleotide SEQ ID NOS 267/397/398 and 278/403/404. As shown in FIG. 20B, treatment of cells with the siRNA-ASCT2 against nucleotide SEQ ID NOS 267/356/402, 267/397/398, 267/399/400, 278/367/408, 278/403/404, 278/405/406, as described herein, and one commercially available siRNAs (SI00097930 from QIAGEN) for 6 h significantly decreased proliferation of human colon cancer HTC-116 cells at 72 h, though evidently with siRNA-ASCT2 against nucleotide SEQ ID NO: 278/403/404.

Example 1

LAT1 and ASCT2 Immunoblotting in the Xenograft Tumour Model

The presence of LAT1 protein and ASCT2 was studied by means of immunoblotting using an antibodies raised against LAT1 and ASCT2. As shown in FIG. 21, the antibody raised against LAT1 and ASCT2 recognized the presence of LAT1 and ASCT2 in both tumours (T1 and T2) derived from human colon cancer HTC-116 cells.

Example 16

LAT1 and ASCT2 Gene Expression in Human Cancer Cells

The presence of LAT1 and ASCT2 mRNA was studied by means of Real-time PCR using primers against LAT1 and ASCT2. As shown in FIG. 22, LAT1 and ASCT2 gene expression relative to the house keeping gene GADPH was found in both tumours (T1 and T2) derived from human colon cancer HTC-116 cells.

Example 17

Tumour Growth

As shown in FIG. 23, the relative tumour volume in the xenograft tumour model developed in immune deficient mice injected subcutaneously with human colon cancer HTC-116 cells and treated every other day with intratumoral injections (50 µL) of vehicle (Injectin®) or the siRNA-LAT1 against nucleotide SEQ ID NO: 58/387/388 (10 µg) and the siRNA-ASCT2 against nucleotide SEQ ID NO: 278/403/404 (10 µg), as described herein. The reduction in relative tumour volume by the siRNA-LAT1 against nucleotide SEQ ID NO: 58/387/388 (10 µg) and the siRNA-ASCT2 against nucleotide SEQ ID NO: 278/403/404 was statistically significant with p values of 0.0018 and 0.0051, respectively.

CONCLUSION

The treatment of cancer cells expressing LAT1 and/or ASCT2 transporter with siRNA-LAT1 and/or siRNA-ASCT2 leads to a decrease in LAT1 and/or ASCT2 protein and a decrease in $[^{14}C]$-L-leucine uptake and $[^{14}C]$-L-alanine uptake, which is accompanied by a decrease in cell proliferation. The decrease in cell viability and proliferation of cancer cells induced by the siRNA-LAT1 and/or the siRNA-ASCT2 is accompanied by apoptosis and a decrease in tumour growth and metastasis potential, as evidenced in nude mice subcutaneous tumours of human colon cancer HTC-116 cells.

Additional aspects of the invention will be apparent to those skilled in the art, or may be learned from the practice of the invention. The objects and advantages of the invention may be realized and attained by means of the instrumentalities and combinations particularly pointed out in the appended claims.

REFERENCES

Baggetto L G (1992). Deviant energetic metabolism of glycolytic cancer cells. *Biochimie* 74 959-974.

Barel M, Meibom K, Dubail I, Botella J, Charbit A (2012). *Francisella tularensis* regulates the expression of the amino acid transporter SLCIA5 in infected THP-1 human monocytes. *Cell Microbiol* 14: 1769-1783.

Betsunoh H, Fukuda T, Anzai N, Nishihara D, Mizuno T, Yuki H, et al. (2013). Increased expression of system large amino acid transporter (LAT)-1 mRNA is associated with invasive potential and unfavorable prognosis of human clear cell renal cell carcinoma. *BMC Cancer* 13: 509-519.

Biology EoNC (2003). Whither RNAi? *Nature Cell Biology* 5: 489-490.

Broer S, Broer A, Hamprecht B (1997). Expression of the surface antigen 4F2hc affects system-L-like neutral-amino-acid-transport activity in mammalian cells. *Biochem J* 324 535-541.

Brummelkamp T R, Bernards R, Agami R (2002). A system for stable expression of short interfering RNAs in mammalian cells. *Science* 296: 550-553.

Bryan C F, Perez J C, Julie E S, Sofia B C, Barrie P B (2004). Inducible antisense RNA targeting amino acid transporter ATB0/ASCT2 elicits apoptosis in human hepatoma cells. *American Journal of Physiology—Gastrointestinal and Liver Physiology*.

Christensen H N (1990). Role of amino acid transport and countertransport in nutrition and metabolism. *Physiol Rev* 70 43-77.

Chuntao T, Shixin L, Qingxia F, Weijie Z, Shunchang J, Xiao Z, et al. (2015). Prognostic Significance of Tumor-infiltrating CD8+ or CD3+T Lymphocytes and Interleukin-2 Expression in Radically Resected Non-small Cell Lung Cancer. *Chinese Medical Journal* 128: 105-110.

Corbet C, Ragelle H, Pourcelle V, Vanvarenberg K, Marchand-Brynaert J, Preat V, et al. (2016). Delivery of siRNA targeting tumor metabolism using non-covalent PEGylated chitosan nanoparticles: Identification of an optimal combination of ligand structure, linker and grafting method. *J Control Release* 223: 53-63.

Davis M E (2009). The first targeted delivery of siRNA in humans via a self-assembling, cyclodextrin polymer-based nanoparticle: from concept to clinic. *Mol Pharm* 6: 659-668.

Denoyer D, Kirby L, Waldeck K, Roselt P, Neels O C, Bourdier T, et al. (2012). Preclinical characterization of 18F-D-FPHCys, a new amino acid-based PET tracer. *Eur J Nucl Med Mol Imaging* 39: 703-712.

Dickens D, Webb S D, Antonyuk S, Giannoudis A, Owen A, Radisch S, et al. (2013). Transport of gabapentin by LAT1 (SLC7A5). *Biochem Pharmacol* 85: 1672-1683.

Ebara T, Kaira K, Saito J, Shioya M, Asao T, Takahashi T, et al. (2010). L-type amino-acid transporter 1 expression predicts the response to preoperative hyperthermo-chemoradiotherapy for advanced rectal cancer. *Anticancer Res* 30: 4223-4227.

Elbashir S M, Harborth J, Lendeckel W, Yalcin A, Weber K, Tuschl T (2001). Duplexes of 21-nucleotide RNAs mediate RNA interference in cultured mammalian cells. *Nature* 411: 494-498.

Eltz S, Comperat E, Cussenot O, Roupret M (2008). Molecular and histological markers in urothelial carcinomas of the upper urinary tract. *BJU Int* 102: 532-535.

Emer C, Helen I, Deirdre W, Mark W, Kate D, Laura S M, et al. (2013). Prognostic Significance of Deregulated Dicer Expression in Breast Cancer. *PLoS ONE* 8: e83724.

Feral C C, Nishiya N, Fenczik C A, Stuhlmann H, Slepak M, Ginsberg M H (2005). CD98hc (SLC3A2) mediates integrin signalling. *Proc Natl Acad Sci USA* 102: 355-360.

Fire A, Xu S, Montgomery M K, Kostas S A, Driver S E, Mello C C (1998). Potent and specific genetic interference by double-stranded RNA in Caenorhabditis elegans. *Nature* 391: 806-811.

Fuchs B C, Bode B P (2005). Amino acid transporters ASCT2 and LAT1 in cancer: partners in crime? *Semin Cancer Biol* 15: 254-266.

Fuchs B C, Perez J C, Suetterlin J E, Chaudhry S B, Bode B P (2004). Inducible antisense RNA targeting amino acid transporter ATB0/ASCT2 elicits apoptosis in human hepatoma cells. *Am J Physiol Gastrointest Liver Physiol* 286: G467-478.

Fukumoto S, Hanazono K, Komatsu T, Iwano H, Kadosawa T, Uchide T (2013). L-type amino acid transporter 1 (LAT1) expression in canine mammary gland tumors. *J Vet Med Sci* 75: 431-437.

Furugen A, Ishiguro Y, Kobayashi M, Narumi K, Nishimura A, Hirano T, et al. (2016). Involvement of I-type amino acid transporter 1 in the transport of gabapentin into human placental choriocarcinoma cells. *Reprod Toxicol* 67: 48-55.

Furuya M, Horiguchi J, Nakajima H, Kanai Y, Oyama T (2012). Correlation of L-type amino acid transporter 1 and CD98 expression with triple negative breast cancer prognosis. *Cancer Sci* 103: 382-389.

Gaccioli F, Aye I L, Roos S, Lager S, Ramirez V I, Kanai Y, et al. (2015). Expression and functional characterisation of System L amino acid transporters in the human term placenta. *Reprod Biol Endocrinol* 13: 57.

Ge N J, Shi Z Y, Yu X H, Huang X J, Wu Y S, Chen Y Y, et al. (2015). Genetic Variants in ASCT2 Gene are Associated with the Prognosis of Transarterial Chemoembolisation-Treated Early-Stage Hepatocelluar Carcinoma. *Asian Pac J Cancer Prev* 16: 4103-4107.

Habermeier A, Graf J, Sandhofer B F, Boissel J P, Roesch F, Closs E I (2015). System L amino acid transporter LAT1 accumulates O-(2-fluoroethyl)-L-tyrosine (FET). *Amino Acids* 47: 335-344.

Hannon G J (2002). RNA interference. *Nature* 418: 244-251.

Harborth J, Elbashir S M, Bechert K, Tuschl T, Weber K (2001). Identification of essential genes in cultured mammalian cells using small interfering RNAs. *J Cell Sci* 114: 4557-4565.

Hassanein M, Hoeksema M D, Shiota M, Qian J, Harris B K, Chen H, et al. (2013). SLC1A5 mediates glutamine transport required for lung cancer cell growth and survival. *Clin Cancer Res* 19: 560-570.

Hassanein M, Qian J, Hoeksema M D, Wang J, Jacobovitz M, Ji X, et al. (2015). Targeting SLC1a5-mediated glutamine dependence in non-small cell lung cancer. *Int J Cancer* 137: 1587-1597.

Hayashi K, Jutabha P, Endou H, Anzai N (2012). c-Myc is crucial for the expression of LAT1 in MIA Paca-2 human pancreatic cancer cells. *Oncology reports* 28: 862-866.

Hayashi K, Jutabha P, Endou H, Sagara H, Anzai N (2013). LAT1 is a critical transporter of essential amino acids for immune reactions in activated human T cells. *J Immunol* 191: 4080-4085.

Honjo H, Kaira K, Miyazaki T, Yokobori T, Kanai Y, Nagamori S, et al. (2016). Clinicopathological significance of LAT1 and ASCT2 in patients with surgically resected esophageal squamous cell carcinoma. *J Surg Oncol* 113: 381-389.

Ichinoe M, Yanagisawa N, Mikami T, Hana K, Nakada N, Endou H, et al. (2015). L-type amino acid transporter 1 (LAT1) expression in lymph node metastasis of gastric carcinoma: Its correlation with size of metastatic lesion and Ki-67 labeling. Pathology, research and practice "in press".

Ichinoe M, Mikami T, Yoshida T, Igawa I, Tsuruta T, Nakada N, et al. (2011). High expression of L-type amino-acid transporter 1 (LAT1) in gastric carcinomas: comparison with non-cancerous lesions. *Pathol Int* 61: 281-289.

Imai H, Kaira K, Oriuchi N, Yanagitani N, Sunaga N, Ishizuka T, et al. (2009). L-type amino acid transporter 1 expression is a prognostic marker in patients with surgically resected stage I non-small cell lung cancer. *Histopathology* 54: 804-813.

Isoda A, Kaira K, Iwashina M, Oriuchi N, Tominaga H, Nagamori S, et al. (2014). Expression of L-type amino acid transporter 1 (LAT1) as a prognostic and therapeutic indicator in multiple myeloma. *Cancer Sci* 105: 1496-1502.

Jacque J-M, Triques K, Stevenson M (2002). Modulation of HIV-1 replication by RNA interference. *Nature* 418: 435-438.

Kaira K, Sunose Y, Oriuchi N, Kanai Y, Takeyoshi I (2014). CD98 is a promising prognostic biomarker in biliary tract cancer. *Hepatobiliary Pancreat Dis Int* 13: 654-657.

Kaira K, Arakawa K, Shimizu K, Oriuchi N, Nagamori S, Kanai Y, et al. (2015a). Relationship between CD147 and expression of amino acid transporters (LAT1 and ASCT2) in patients with pancreatic cancer. *Am J Transl Res* 7: 356-363.

Kaira K, Nakagawa K, Ohde Y, Okumura T, Takahashi T, Murakami H, et al. (2012a). Depolarized MUC1 expression is closely associated with hypoxic markers and poor outcome in resected non-small cell lung cancer. *Int J Surg Pathol* 20: 223-232.

Kaira K, Toyoda M, Shino M, Sakakura K, Takahashi K, Tominaga H, et al. (2013). Clinicopathological significance of L-type amino acid transporter 1 (LAT1) expression in patients with adenoid cystic carcinoma. *Pathol Oncol Res* 19: 649-656.

Kaira K, Sunose Y, Arakawa K, Sunaga N, Shimizu K, Tominaga H, et al. (2015b). Clinicopathological significance of ASC amino acid transporter-2 expression in pancreatic ductal carcinoma. *Histopathology* 66: 234-243.

Kaira K, Oriuchi N, Imai H, Shimizu K, Yanagitani N, Sunaga N, et al. (2009a). L-type amino acid transporter 1 (LAT1) is frequently expressed in thymic carcinomas but is absent in thymomas. *J Surg Oncol* 99: 433-438.

Kaira K, Oriuchi N, Imai H, Shimizu K, Yanagitani N, Sunaga N, et al. (2009b). Prognostic significance of L-type amino acid transporter 1 (LAT1) and 4F2 heavy chain (CD98) expression in early stage squamous cell carcinoma of the lung. *Cancer Sci* 100: 248-254.

Kaira K, Takahashi T, Murakami H, Shukuya T, Kenmotsu H, Naito T, et al. (2011a). Relationship 50 between LAT1 expression and response to platinum-based chemotherapy in non-small cell lung cancer patients with postoperative recurrence. *Anticancer Res* 31: 3775-3782.

Kaira K, Oriuchi N, Imai H, Shimizu K, Yanagitani N, Sunaga N, et al. (2008a). I-type amino acid transporter 1 and CD98 expression in primary and metastatic sites of human neoplasms. *Cancer Sci* 99: 2380-2386.

Kaira K, Oriuchi N, Imai H, Shimizu K, Yanagitani N, Sunaga N, et al. (2008b). Prognostic significance of L-type amino acid transporter 1 expression in resectable stage I-III nonsmall cell lung cancer. *Br J Cancer* 98: 742-748.

Kaira K, Oriuchi N, Imai H, Shimizu K, Yanagitani N, Sunaga N, et al. (2009c). CD98 expression is associated with poor prognosis in resected non-small-cell lung cancer with lymph node metastases. *Ann Surg Oncol* 16: 3473-3481.

Kaira K, Oriuchi N, Shimizu K, Imai H, Tominaga H, Yanagitani N, et al. (2010a). Comparison of L-type amino acid transporter 1 expression and L-[3-18F]-alpha-methyl tyrosine uptake in outcome of non-small cell lung cancer. *Nucl Med Biol* 37: 911-916.

Kaira K, Oriuchi N, Imai H, Shimizu K, Yanagitani N, Sunaga N, et al. (2010b). Prognostic significance of L-type amino acid transporter 1 (LAT1) and 4F2 heavy chain (CD98) expression in surgically resectable stage III non-small cell lung cancer. *Exp Ther Med* 1: 799-808.

Kaira K, Oriuchi N, Imai H, Shimizu K, Yanagitani N, Sunaga N, et al. (2008c). Expression of L-type amino acid transporter 1 (LAT1) in neuroendocrine tumors of the lung. *Pathol Res Pract* 204: 553-561.

Kaira K, Oriuchi N, Shimizu K, Ishikita T, Higuchi T, Imai H, et al. (2009d). Correlation of angiogenesis with 18F-FMT and 18F-FDG uptake in non-small cell lung cancer. *Cancer Sci* 100: 753-758.

Kaira K, Oriuchi N, Takahashi T, Nakagawa K, Ohde Y, Okumura T, et al. (2011b). LAT1 expression is closely associated with hypoxic markers and mTOR in resected non-small cell lung cancer. *Am J Transl Res* 3: 468-478.

Kaira K, Oriuchi N, Takahashi T, Nakagawa K, Ohde Y, Okumura T, et al. (2011c). L-type amino acid transporter 1 (LAT1) expression in malignant pleural mesothelioma. *Anticancer Res* 31: 4075-4082.

Kaira K, Oriuchi N, Otani Y, Shimizu K, Tanaka S, Imai H, et al. (2007). Fluorine-18-alpha-methyltyrosine positron emission tomography for diagnosis and staging of lung cancer: a clinicopathologic study. *Clin Cancer Res* 13: 6369-6378.

Kaira K, Sunose Y, Arakawa K, Ogawa T, Sunaga N, Shimizu K, et al. (2012b). Prognostic significance of L-type amino-acid transporter 1 expression in surgically resected pancreatic cancer. *Br J Cancer* 107: 632-638.

Kanai Y, Endou H (2001). Heterodimeric amino acid transporters: molecular biology and pathological and pharmacological relevance. *Curr Drug Metab* 2: 339-354.

Kanai Y, Segawa H, Miyamoto K, Uchino H, Takeda E, Endou H (1998). Expression cloning and characterization of a transporter for large neutral amino acids activated by the heavy chain of 4F2 antigen (CD98). *J Biol Chem* 273: 23629-23632.

Kaneko S, Ando A, Okuda-Ashitaka E, Maeda M, Furuta K, Suzuki M, et al. (2007). Ornithine transport via cationic amino acid transporter-1 is involved in ornithine cytotoxicity in retinal pigment epithelial cells. *Invest Ophthalmol Vis Sci* 48: 464-471.

Kaoru K, Toshiaki K, Tomohiko Y, Yuichi T, Takahiro H, Koji N, et al. (2011). Positive Relationship between L-type Amino Acid Transporter 1 Expression and Liver Metastasis in T3 Colorectal Cancer. *The Showa University Journal of Medical Sciences* 23: 145-151.

Keyaerts M, Lahoutte T, Neyns B, Caveliers V, Vanhove C, Everaert H, et al. (2007). 123I-2-iodo-tyrosine, a new tumour imaging agent: human biodistribution, dosimetry and initial clinical evaluation in glioma patients. *Eur J Nucl Med Mol Imaging* 34: 994-1002.

Kim C H, Park K J, Park J R, Kanai Y, Endou H, Park J C, et al. (2006a). The RNA interference of amino acid transporter LAT1 inhibits the growth of K B human oral cancer cells. *Anticancer Res* 26: 2943-2948.

Kim C S, Cho S H, Chun H S, Lee S Y, Endou H, Kanai Y, et al. (2008). BCH, an inhibitor of system L amino acid transporters, induces apoptosis in cancer cells. *Biological & pharmaceutical bulletin* 31: 1096-1100.

Kim D K, Ahn S G, Park J C, Kanai Y, Endou H, Yoon J H (2004a). Expression of L-type amino acid transporter 1 (LAT1) and 4F2 heavy chain (4F2hc) in oral squamous cell carcinoma and its precursor lesions. *Anticancer Res* 24: 1671-1675.

Kim H M, Lee Y K, Koo J S (2016). Expression of glutamine metabolism-related proteins in thyroid cancer. *Oncotarget*.

Kim H M, Kim do H, Jung W H, Koo J S (2014). Metabolic phenotypes in primary unknown metastatic carcinoma. *J Transl Med* 12: 2.

Kim K D, Ahn S G, Park J C, Kanai Y, Endou H, Yoon J H (2004b). Expression of L-type amino acid transporter 1 (LAT1) and 4F2 heavy chain (4F2hc) in oral squamous cell carcinoma and its precursor lesions. *Anticancer Res* 24: 1671-1675.

Kim K D, Kanai Y, Choi H W, Tangtrongsup S, Chairoungdua A, Babu E, et al. (2002). Characterization of the system L amino acid transporter in T24 human bladder carcinoma cells. *Biochim Biophys Acta* 1565: 112-121.

Kim S, Jung W H, Koo J S (2013). The expression of glutamine-metabolism-related proteins in breast phyllodes tumors. *Tumour Biol* 34: 2683-2689.

Kim S G, Kim H H, Kim H K, Kim C H, Chun H S, Kanai Y, et al. (2006b). Differential expression and functional characterization of system L amino acid transporters in human normal osteoblast cells and osteogenic sarcoma cells. *Anticancer Res* 26: 1989-1996.

Koo J S, Yoon J S (2015). Expression of metabolism-related proteins in lacrimal gland adenoid cystic carcinoma. *Am J Clin Pathol* 143: 584-592.

Kudo Y, Boyd C A (2004). RNA interference-induced reduction in CD98 expression suppresses cell fusion during syncytialization of human placental BeWo cells. *FEBS Lett* 577 473-477.

Kuhne A, Tzvetkov M V, Hagos Y, Lage H, Burckhardt G, Brockmoller J (2009). Influx and efflux transport as determinants of melphalan cytotoxicity: Resistance to melphalan in MDR1 overexpressing tumor cell lines. *Biochem Pharmacol* 78: 45-53.

Kuhne A, Kaiser R, Schirmer M, Heider U, Muhlke S, Niere W, et al. (2007). Genetic polymorphisms in the amino acid transporters LAT1 and LAT2 in relation to the pharmacokinetics and side effects of melphalan. *Pharmacogenetics and genomics* 17: 505-517.

Kyoichi K (2010). Prognostic significance of L-type amino acid transporter 1 (LAT1) and 4F2 heavy chain (CD98) expression in surgically resectable stage III non-small cell lung cancer. *Experimental and Therapeutic Medicine* 1: 799-808.

Kyoichi K, Yutaka S, Kazuhisa A, Noriaki S, Kimihiro S, Hideyuki T, et al. (2015). Clinicopathological significance of ASC amino acid transporter-2 expression in pancreatic ductal carcinoma. *Histopathology.*

Kyoichi K, Noboru O, Hisao I, Kimihiro S, Noriko Y, Noriaki S, et al. (2008). Expression of L-type amino acid transporter 1 (LAT1) in neuroendocrine tumors of the lung. *Pathology, research and practice:* 553-561.

Lee N S, Dohjima T, Bauer G, Li H, Li M-J, Ehsani A, et al. (2001). Expression of small interfering RNAs targeted against HIV-1 rev transcripts in human cells. *Nature Biotechnology* 19: 500-505.

Lee N S, Dohjima T, Bauer G, Li H, Li M-J, Ehsani A, et al. (2002). Expression of small interfering RNAs targeted against HIV-1 rev transcripts in human cells. *Nature Biotechnology* 20: 500-505.

Lee N Y, Kim Y, Ryu H, Kang Y S (2017). The alteration of serine transporter activity in a cell line model of amyotrophic lateral sclerosis (ALS). *Biochem Biophys Res Commun* 483: 135-141.

Li J, Qiang J, Chen S F, Wang X, Fu J, Chen Y (2013). The impact of L-type amino acid transporter 1 (LAT1) in human hepatocellular carcinoma. *Tumour Biol* 34: 2977-2981.

Li R, Younes M, Frolov A, Wheeler T M, Scardino P, Ohori M, et al. (2003). Expression of neutral amino acid transporter ASCT2 in human prostate. *Anticancer Res* 23: 3413-3418.

Li S, Whorton A R (2005). Identification of stereoselective transporters for S-nitroso-L-cysteine: role of LAT1 and LAT2 in biological activity of S-nitrosothiols. *J Biol Chem* 280: 20102-20110.

Liang Z, Cho H T, Williams L, Zhu A, Liang K, Huang K, et al. (2011). Potential Biomarker of L-type Amino Acid Transporter 1 in Breast Cancer Progression. *Nucl Med Mol Imaging* 45: 93-102.

Liu W, Chen H, Wong N, Haynes W, Baker C M, Wang X (2017). Pseudohypoxia induced by miR-126 deactivation promotes migration and therapeutic resistance in renal cell carcinoma. *Cancer Lett* 394: 65-75.

Liu Y, Yang L, An H, Chang Y, Zhang W, Zhu Y, et a. (2015). High expression of Solute Carrier Family 1, member 5 (SLC1A5) is associated with poor prognosis in clear-cell renal cell carcinoma. *Sci Rep* 5: 16954.

Masashi N, Satoru K, Kyoichi K, Hiroki T, Yuichi Y, Norio H, et al. (2014). Expression of amino acid transporters (LAT1, ASCT2 and xCT) as clinical significance in hepatocellular carcinoma. *Hepatology Research:* 1-9.

Mazurek S, Eigenbrodt (2003). The tumor metabolome. *Anticancer Res* 23: 1149-1154.

Medina M A, Marquez J, Nunez de Castro I (1992a). Interchange of amino acids between tumor and host. *Biochem Med Metabol Biol* 48: 1-7.

Medina M A, Sanchez-Jimenez F, Marquez J, Rodriguez Quesada A, Nunez de Castro I (1992b). Relevance of glutamine metabolism to tumor cell growth. *Mol Cell Biochem* 113 1-15.

Miko E, Margitai Z, Czimmerer Z, Varkonyi I, Dezso B, Lanyi A, et al. (2011). miR-126 inhibits proliferation of small cell lung cancer cells by targeting SLC7A5. *FEBS Lett* 585: 1191-1196.

Miyagishi M, Taira K (2002). U6 promoter-driven siRNAs with four uridine 3' overhangs efficiently suppress targeted gene expression in mammalian cells. *Nature Biotechnology* 19: 497-500.

Nakanishi K, Ogata S, Matsuo H, Kanai Y, Endou H, Hiroi S, et al. (2007). Expression of LAT1 predicts risk of progression of transitional cell carcinoma of the upper urinary tract. *Virchows Arch* 451: 681-690.

Nawashiro H, Otani N, Shinomiya N, Fukui S, Ooigawa H, Shima K, et al. (2006). L-type amino acid transporter 1 as a potential molecular target in human astrocytic tumors. *Int J Cancer* 119: 484-492.

Nicklin P, Bergman P, Zhang B, Triantafellow E, Wang H, Nyfeler B, et al. (2009). Bidirectional transport of amino acids regulates mTOR and autophagy. *Cell* 136: 521-534.

Nikkuni O, Kaira K, Toyoda M, Shino M, Sakakura K, Takahashi K, et al. (2015). Expression of Amino Acid Transporters (LAT1 and ASCT2) in Patients with Stage III/IV Laryngeal Squamous Cell Carcinoma. *Pathol Oncol Res* 21: 1175-1181.

Nobusawa A, Kim M, Kaira K, Miyashita G, Negishi A, Oriuchi N, et al. (2013). Diagnostic usefulness of (1)(8) F-FAMT PET and L-type amino acid transporter 1 (LAT1) expression in oral squamous cell carcinoma. *Eur J Nucl Med Mol Imaging* 40: 1692-1700.

Ohkame H, Masuda H, Ishii Y, Kanai Y (2001). Expression of L-type amino acid transporter 1 (LAT1) and 4F2 heavy chain (4F2hc) in liver tumor lesions of rat models. *J Surg Oncol* 78: 265-271; discussion 271-262.

Ohkawa M, Ohno Y, Masuko K, Takeuchi A, Suda K, Kubo A, et al. (2011). Oncogenicity of L-type amino-acid transporter 1 (LAT1) revealed by targeted gene disruption in chicken DT40 cells: LAT1 is a promising molecular target for human cancer therapy. *Biochem Biophys Res Commun* 406: 649-655.

Okubo S, Zhen H N, Kawai N, Nishiyama Y, Haba R, Tamiya T (2010). Correlation of L-methyl-11C-methionine (MET) uptake with L-type amino acid transporter 1 in human gliomas. *J Neurooncol* 99: 217-225.

Okudaira H, Shikano N, Nishii R, Miyagi T, Yoshimoto M, Kobayashi M, et al. (2011). Putative transport mechanism and intracellular fate of trans-1-amino-3-18F-fluorocyclobutanecarboxylic acid in human prostate cancer. *J Nucl Med* 52: 822-829.

Paddison P J, Caudy A A, Bernstein E, Hannon G J, Conklin D S S (2002). hort hairpin RNAs (shRNAs) induce sequence-specific silencing in mammalian cells. *Genes Dev* 16: 948-958.

Paul C P, Good P D, Winer I, Engelke D R (2002). Effective Expression of Small Interfering RNA in human cells. *Nature Biotechnology* 19: 505-508.

Pinho M J, Serrao M P, Jose P A, Soares-da-Silva P (2007a). Overexpression of non-functional LAT1/4F2hc in renal proximal tubular epithelial cells from the spontaneous hypertensive rat. *Cell Physiol Biochem* 20: 535-548.

Pinho M J, Pinto V, Serrao M P, Jose P A, Soares-da-Silva P (2007b). Underexpression of the Na+-dependent neutral amino acid transporter ASCT2 in the spontaneously hypertensive rat kidney. *Am J Physiol Regul Integr Comp Physiol* 293: R538-R547.

Polet F, Martherus R, Corbet C, Pinto A, Feron O (2016). Inhibition of glucose metabolism prevents glycosylation of the glutamine transporter ASCT2 and promotes compensatory LAT1 upregulation in leukemia cells. *Oncotarget* 7: 46371-46383.

Ren P, Yue M, Xiao D, Xiu R, Gan L, Liu H, et al. (2015). ATF4 and N-Myc coordinate glutamine metabolism in MYCN-amplified neuroblastoma cells through ASCT2 activation. *J Pathol* 235: 90-100.

Sakata T, Ferdous G, Tsuruta T, Satoh T, Baba S, Muto T, et al. (2009). L-type amino-acid transporter 1 as a novel biomarker for high-grade malignancy in prostate cancer. *Pathol Int* 59: 7-18.

Sang J, Lim Y P, Panzica M, Finch P, Thompson N L (1995). TA1, a highly conserved oncofetal complementary DNA from rat hepatoma, encodes an integral membrane protein associated with liver development, carcinogenesis, and cell activation. *Cancer Res* 55: 1152-1159.

Segawa A, Nagamori S, Kanai Y, Masawa N, Oyama T (2013). L-type amino acid transporter 1 expression is highly correlated with Gleason score in prostate cancer. *Mol Clin Oncol* 1: 274-280.

Shennan D B, Thomson J (2008). Inhibition of system L (LAT1/CD98hc) reduces the growth of cultured human breast cancer cells. *Oncology reports* 20: 885-889.

Shennan D B, Thomson J, Gow I F, Travers M T, Barber M C (2004). L-leucine transport in human breast cancer cells (MCF-7 and MDA-MB-231): kinetics, regulation by estrogen and molecular identity of the transporter. *Biochim Biophys Acta* 1664: 206-216.

Shimizu K, Kaira K, Tomizawa Y, Sunaga N, Kawashima O, Oriuchi N, et al. (2014). ASC amino-acid transporter 2 (ASCT2) as a novel prognostic marker in non-small cell lung cancer. *Br J Cancer* 110: 2030-2039.

Stockhammer F, Plotkin M, Amthauer H, van Landeghem F K, Woiciechowsky C (2008). Correlation of F-18-fluoroethyl-tyrosin uptake with vascular and cell density in non-contrast-enhancing gliomas. *J Neurooncol* 88: 205-210.

Storey B T, Fugere C, Lesieur-Brooks A, Vaslet C, Thompson N L (2005). Adenoviral modulation of the tumor-associated system L amino acid transporter, LAT1, alters amino acid transport, cell growth and 4F2/CD98 expression with cell-type specific effects in cultured hepatic cells. *Int J Cancer* 117: 387-397.

Straka E, Ellinger I, Balthasar C, Scheinast M, Schatz J, Szattler T, et al. (2016). Mercury toxicokinetics of the healthy human term placenta involve amino acid transporters and ABC transporters. *Toxicology* 340: 34-42.

Sui G, Soohoo C, Affar E B, Gay F, Shi Y, Forrester W C, et al. (2002). A DNA vector-based RNAi technology to suppress gene expression in mammalian cells. *Proc Natl Acad Sci USA* 99: 5515-5520.

Suzuki S, Kaira K, Ohshima Y, Ishioka N S, Sohda M, Yokobori T, et al. (2014). Biological significance of fluorine-18-alpha-methyltyrosine (FAMT) uptake on PET in patients with oesophageal cancer. *Br J Cancer* 110: 1985-1991.

Takeuchi K, Ogata S, Nakanishi K, Ozeki Y, Hiroi S, Tominaga S, et al. (2010). LAT1 expression in non-small-cell lung carcinomas: analyses by semiquantitative reverse transcription-PCR (237 cases) and immunohistochemistry (295 cases). *Lung Cancer* 68: 58-65.

Tamai S, Masuda H, Ishii Y, Suzuki S, Kanai Y, Endou H (2001). Expression of L-type amino acid transporter 1 in a rat model of liver metastasis: positive correlation with tumor size. *Cancer Detect Prev* 25: 439-445.

Tomblin J K, Arthur S, Primerano D A, Chaudhry A R, Fan J, Denvir J, et al. (2016). Aryl hydrocarbon receptor (AHR) regulation of L-Type Amino Acid Transporter 1 (LAT-1) expression in MCF-7 and MDA-MB-231 breast cancer cells. *Biochem Pharmacol* 106: 94-103.

Toyoda M, Kaira K, Ohshima Y, Ishioka N S, Shino M, Sakakura K, et al. (2014a). Prognostic significance of amino-acid transporter expression (LAT1, ASCT2, and xCT) in surgically resected tongue cancer. *Br J Cancer* 110: 2506-2513.

Toyoda M, Kaira K, Shino M, Sakakura K, Takahashi K, Takayasu Y, et al. (2014b). CD98 as a novel prognostic indicator for patients with stage III/IV hypopharyngeal squamous cell carcinoma. *Head Neck*: 1-6.

Wang Q, Bailey C G, Ng C, Tiffen J, Thoeng A, Minhas V, et al. (2011). Androgen receptor and nutrient signaling pathways coordinate the demand for increased amino acid transport during prostate cancer progression. *Cancer Res* 71: 7525-7536.

Wang Q, Beaumont K A, Otte N J, Font J, Bailey C G, van Geldermalsen M, et al. (2014). Targeting glutamine transport to suppress melanoma cell growth. *Int J Cancer* 135: 1060-1071.

Wang Q, Hardie R A, Hoy A J, van Geldermalsen M, Gao D, Fazli L, et al. (2015). Targeting ASCT2-mediated glutamine uptake blocks prostate cancer growth and tumour development. *J Pathol*.

Watanabe J, Yokoyama Y, Futagami M, Mizunuma H, Yoshioka H, Washiya K, et al. (2014). L-type amino acid transporter 1 expression increases in well-differentiated but decreases in poorly differentiated endometrial endometrioid adenocarcinoma and shows an inverse correlation with p53 expression. *Int J Gynecol Cancer* 24: 659-663.

Wei L, Tominaga H, Ohgaki R, Wiriyasermkul P, Hagiwara K, Okuda S, et al. (2016). Specific transport of 3-fluoro-1-alpha-methyl-tyrosine by LAT1 explains its specificity to malignant tumors in imaging. *Cancer Sci* 107: 347-352.

Wieland H, Ullrich S, Lang F, Neumeister B (2005). Intracellular multiplication of *Legionella pneumophila* depends on host cell amino acid transporter SLC1A5. *Mol Microbiol* 55: 1528-1537.

Witte D, Ali N, Carlson N, Younes M (2002). Overexpression of the neutral amino acid transporter ASCT2 in human colorectal adenocarcinoma. *Anticancer Res* 22: 2555-2557.

Wongthai P, Hagiwara K, Miyoshi Y, Wiriyasermkul P, Wei L, Ohgaki R, et al. (2015). Boronophenylalanine, a boron delivery agent for boron neutron capture therapy, is transported by ATB0,+, LAT1 and LAT2. *Cancer Sci* 106: 279-286.

Xia H, Mao Q, Paulson H L, Davidson B L (2002). siRNA-mediated gene silencing in vitro and in vivo. *Nat Biotechnol* 20: 1006-1010.

Xia L, Coon J S t, Su E, Pearson E K, Ping Y, Ishikawa H, et al. (2010). LAT1 regulates growth of uterine leiomyoma smooth muscle cells. *Reprod Sci* 17: 791-797.

Xu M, Sakamoto S, Matsushima J, Kimura T, Ueda T, Mizokami A, et al. (2016). Up-Regulation of LAT1 during Antiandrogen Therapy Contributes to Progression in Prostate Cancer Cells. *J Urol* 195: 1588-1597.

Yagita H, Masuko T, Hashimoto Y (1986). Inhibition of tumor cell growth in vitro by murine monoclonal antibodies that recognize a proliferation-associated cell surface antigen system in rats and humans. *Cancer Res* 46: 1478-1484.

Yamauchi K, Sakurai H, Kimura T, Wiriyasermkul P, Nagamori S, Kanai Y, et al. (2009). System L amino acid transporter inhibitor enhances anti-tumor activity of cisplatin in a head and neck squamous cell carcinoma cell line. *Cancer Lett* 276: 95-101.

Yanagida O, Kanai Y, Chairoungdua A, Kim D K, Segawa H, Nii T, et al. (2001). Human L-type amino acid transporter 1 (LAT1): characterization of function and expression in tumor cell lines. *Biochim Biophys Acta* 1514: 291-302.

Yanagisawa N, Ichinoe M, Mikami T, Nakada N, Hana K, Koizumi W, et al. (2012). High expression of L-type amino acid transporter 1 (LAT1) predicts poor prognosis in pancreatic ductal adenocarcinomas. *J Clin Pathol* 65: 1019-1023.

Yanagisawa N, Hana K, Nakada N, Ichinoe M, Koizumi W, Endou H, et al. (2014). High expression of L-type amino acid transporter 1 as a prognostic marker in bile duct adenocarcinomas. *Cancer Med* 3: 1246-1255.

Yanagisawa N, Satoh T, Hana K, Ichinoe M, Nakada N, Endou H, et al. (2015). L-amino acid transporter 1 may be a prognostic marker for local progression of prostatic cancer under expectant management. *Cancer Biomark* 15: 365-374.

Yin Z, Jiang H, Syversen T, Rocha J B, Farina M, Aschner M (2008). The methylmercury-L-cysteine conjugate is a substrate for the L-type large neutral amino acid transporter. *J Neurochem* 107: 1083-1090.

Yoon J H, Kim I J, Kim H, Kim H J, Jeong M J, Ahn S G, et al. (2005). Amino acid transport system L is differently expressed in human normal oral keratinocytes and human oral cancer cells. *Cancer Lett* 222: 237-245.

Youland R S, Kitange G J, Peterson T E, Pafundi D H, Ramiscal J A, Pokorny J L, et al. (2013). The role of LAT1 in (18)F-DOPA uptake in malignant gliomas. *J Neurooncol* 111: 11-18.

Yu J Y, DeRuiter S L, Turner D L (2002). RNA interference by expression of short-interfering RNAs and hairpin RNAs in mammalian cells. *Proc. Natl. Acad. Sci. USA* 99: 6047-6052.

Zhou X, Zheng W, Nagana Gowda G A, Raftery D, Donkin S S, Bequette B, et al. (2016). 1,25-Dihydroxyvitamin D inhibits glutamine metabolism in Harvey-ras transformed MCF10A human breast epithelial cell. *J Steroid Biochem Mol Biol* 163: 147-156.

---

The invention claimed is:

1. An siNA (short interfering nucleic acid) molecule that can reduce expression of a LAT1 gene in a cell, wherein said molecule comprises a nucleic acid sequence selected from SEQ ID NO: 152, 153, 159, 162 and 184, or a nucleic acid sequence that differs from one of SEQ ID NO: 152, 153, 159, 162 and 184 by no more than one nucleotide, or said molecule comprises a nucleic acid sequence that is perfectly complementary to the full length of a sequence selected from SEQ ID NO: 152, 153, 159, 162 and 184, or is a variant thereof that differs from the perfectly complementary nucleic acid sequence by no more than 1 nucleotide.

2. An siNA molecule of claim 1, wherein said molecule is between 19 and 25 base pairs in length.

3. An siNA molecule of claim 1, wherein the siNA is selected from dsRNA, siRNA or shRNA.

4. An siNA molecule of claim 3, wherein the siNA is siRNA.

5. An siNA molecule of claim 1, wherein the siNA comprises 5' and/or 3' overhangs.

6. An siNA of claim 1, wherein the siNA comprises at least one chemical modification.

7. A pharmaceutical composition comprising at least one siNA of claim 1 and a pharmaceutically acceptable carrier.

8. A nucleic acid construct or vector comprising a nucleic acid sequence encoding an siNA of claim 1.

9. An siNA molecule, where said molecule comprises a sense sequence with a nucleic acid sequence selected from SEQ ID Nos 387 and 389 or a nucleic acid sequence that differs from one of SEQ ID Nos 387 and 389 by no more than one nucleotide, and an antisense sequence with a nucleic acid sequence selected from SEQ ID Nos 388, 390, and 412 or a nucleic acid sequence that differs from one of SEQ ID Nos 388, 390, and 412 by no more than one nucleotide.

* * * * *